(12) United States Patent
Mulligan et al.

(10) Patent No.: US 11,406,269 B2
(45) Date of Patent: *Aug. 9, 2022

(54) RAPID DETECTION OF BLEEDING FOLLOWING INJURY

(71) Applicants: Flashback Technologies, Inc., Boulder, CO (US); The Regents of the University of Colorado, Denver, CO (US)

(72) Inventors: Isobel Jane Mulligan, Niwot, CO (US); Gregory Zlatko Grudic, Niwot, CO (US); Steven L. Moulton, Littleton, CO (US)

(*) Notice: Subject to any disclaimer, the term of this patent is extended or adjusted under 35 U.S.C. 154(b) by 294 days.

This patent is subject to a terminal disclaimer.

(21) Appl. No.: 15/620,701

(22) Filed: Jun. 12, 2017

(65) Prior Publication Data
US 2017/0281020 A1  Oct. 5, 2017

Related U.S. Application Data

(63) Continuation-in-part of application No. 15/261,661, filed on Sep. 9, 2016, and a continuation-in-part of
(Continued)

(51) Int. Cl.
*A61B 5/02* (2006.01)
*A61B 5/00* (2006.01)
(Continued)

(52) U.S. Cl.
CPC ........ *A61B 5/02042* (2013.01); *A61B 5/0205* (2013.01); *A61B 5/02028* (2013.01);
(Continued)

(58) Field of Classification Search
CPC .............. A61B 5/02028; A61B 5/7275; A61B 5/02042; A61B 5/4875; A61M 5/168
See application file for complete search history.

(56) References Cited

U.S. PATENT DOCUMENTS 4,930,517 A  6/1990 Cohen et al.
5,074,310 A  12/1991 Mick
(Continued)

FOREIGN PATENT DOCUMENTS

CA  2871608  2/2021
EP  2356579  5/2015
(Continued)

OTHER PUBLICATIONS

U.S. Appl. No. 14/885,888, Final Office Action dated Jul. 27, 2017, 29 pages.
(Continued)

*Primary Examiner* — Tse W Chen
*Assistant Examiner* — Michael A Catina
(74) *Attorney, Agent, or Firm* — Capitol Patent & Trademark Law Firm, PLLC

(57) ABSTRACT

Novel tools and techniques are provided for assessing, predicting and/or estimating a probability that a patient is bleeding, in some cases, noninvasively. In various embodiments, tools and techniques are provided for implementing rapid detection of bleeding of the patient or implementing assessment, prediction, or estimation of a probability of bleeding of the patient following injury, in some instances, in real-time before, during, and after fluid resuscitation. According to some embodiments, one or more sensors might monitor physiological data of the patient before, during, and after resuscitation following injury. A computer system might receive and analyze the physiological data, and might estimate a probability that the patient is bleeding, based at least in part on the analyzed physiological data. An indication of at least one of an assessment, prediction, or estimate of a probability that the patient is bleeding may then be displayed on a display device.

33 Claims, 27 Drawing Sheets

Related U.S. Application Data application No. 14/885,888, filed on Oct. 16, 2015, and a continuation-in-part of application No. 14/885,891, filed on Oct. 16, 2015, said application No. 14/885,888 is a continuation-in-part of application No. 14/542,426, filed on Nov. 14, 2014, and a continuation-in-part of application No. 14/542,423, filed on Nov. 14, 2014, which is a continuation-in-part of application No. 14/535,171, filed on Nov. 6, 2014, which is a continuation-in-part of application No. 13/554,483, filed on Jul. 20, 2012, now Pat. No. 9,757,041, which is a continuation-in-part of application No. 13/041,006, filed on Mar. 4, 2011, which is a continuation-in-part of application No. 13/028,140, filed on Feb. 15, 2011, now Pat. No. 8,512,260, which is a continuation-in-part of application No. PCT/US2009/062119, filed on Oct. 26, 2009.

(60) Provisional application No. 62/349,516, filed on Jun. 13, 2016, provisional application No. 62/216,187, filed on Sep. 9, 2015, provisional application No. 62/064,809, filed on Oct. 16, 2014, provisional application No. 62/064,816, filed on Oct. 16, 2014, provisional application No. 61/905,727, filed on Nov. 18, 2013, provisional application No. 61/904,436, filed on Nov. 14, 2013, provisional application No. 61/900,980, filed on Nov. 6, 2013, provisional application No. 61/614,426, filed on Mar. 22, 2012, provisional application No. 61/510,792, filed on Jul. 22, 2011, provisional application No. 61/310,583, filed on Mar. 4, 2010, provisional application No. 61/305,110, filed on Feb. 16, 2010, provisional application No. 61/252,978, filed on Oct. 19, 2009, provisional application No. 61/166,499, filed on Apr. 3, 2009, provisional application No. 61/166,486, filed on Apr. 3, 2009, provisional application No. 61/166,472, filed on Apr. 3, 2009, provisional application No. 61/109,490, filed on Oct. 29, 2008.

(51) Int. Cl.

| | | |
|---|---|---|
| *A61B 5/0205* | (2006.01) | |
| *G16H 50/20* | (2018.01) | |
| *G16H 50/50* | (2018.01) | |
| *G16H 40/63* | (2018.01) | |
| *G16H 50/30* | (2018.01) | |
| *G16H 50/70* | (2018.01) | |
| *A61B 5/0215* | (2006.01) | |
| *A61B 5/03* | (2006.01) | |
| *A61B 5/08* | (2006.01) | |
| *A61B 5/1455* | (2006.01) | |
| *A61B 5/145* | (2006.01) | |
| *A61B 8/08* | (2006.01) | |
| *A61B 7/04* | (2006.01) | |
| *A61M 1/16* | (2006.01) | |
| *A61B 5/029* | (2006.01) | |
| *A61B 5/024* | (2006.01) | |
| *A61B 5/022* | (2006.01) | |
| *G16H 20/17* | (2018.01) | |
| *A61B 5/318* | (2021.01) | |
| *A61B 5/369* | (2021.01) | |
| *A61B 5/398* | (2021.01) | |

(52) U.S. Cl.
CPC .......... *A61B 5/4848* (2013.01); *A61B 5/4875* (2013.01); *A61B 5/7275* (2013.01); *G16H 40/63* (2018.01); *G16H 50/20* (2018.01); *G16H 50/30* (2018.01); *G16H 50/50* (2018.01); *G16H 50/70* (2018.01); *A61B 5/002* (2013.01); *A61B 5/0075* (2013.01); *A61B 5/029* (2013.01); *A61B 5/02152* (2013.01); *A61B 5/02241* (2013.01); *A61B 5/02416* (2013.01); *A61B 5/031* (2013.01); *A61B 5/0809* (2013.01); *A61B 5/14532* (2013.01); *A61B 5/14546* (2013.01); *A61B 5/14551* (2013.01); *A61B 5/318* (2021.01); *A61B 5/369* (2021.01); *A61B 5/398* (2021.01); *A61B 5/4836* (2013.01); *A61B 5/6826* (2013.01); *A61B 5/7246* (2013.01); *A61B 5/7267* (2013.01); *A61B 5/742* (2013.01); *A61B 7/04* (2013.01); *A61B 8/488* (2013.01); *A61B 2562/0219* (2013.01); *A61M 1/1613* (2014.02); *G16H 20/17* (2018.01)

(56) References Cited

U.S. PATENT DOCUMENTS

| | | | |
|---|---|---|---|
| 5,619,990 A | * | 4/1997 | Kanai .............. G16H 50/30 600/300 |
| 5,853,364 A | | 12/1998 | Baker, Jr. et al. |
| 5,865,168 A | | 2/1999 | Isaza |
| 5,967,981 A | | 10/1999 | Watrous |
| 5,984,893 A | | 11/1999 | Ward |
| 6,083,172 A | | 7/2000 | Baker, Jr. et al. |
| 6,094,592 A | | 7/2000 | Yorkey et al. |
| 6,206,830 B1 | | 3/2001 | Diab et al. |
| 6,248,080 B1 | | 6/2001 | Miesel |
| 6,338,713 B1 | | 1/2002 | Chamoun et al. |
| 6,371,921 B1 | | 4/2002 | Caro et al. |
| 6,398,728 B1 | | 6/2002 | Bardy |
| 6,409,675 B1 | | 6/2002 | Turcott |
| 6,411,833 B1 | | 6/2002 | Baker, Jr. et al. |
| 6,553,991 B1 | | 4/2003 | Isaza |
| 6,556,852 B1 | | 4/2003 | Schulze |
| 6,557,553 B1 | | 5/2003 | Borrello |
| 6,558,336 B2 | | 5/2003 | Collins |
| 6,589,189 B2 | | 7/2003 | Meyerson et al. |
| 6,591,122 B2 | | 7/2003 | Schmitt |
| 6,606,509 B2 | | 8/2003 | Schmitt |
| 6,675,031 B1 | | 1/2004 | Porges et al. |
| 6,721,584 B2 | | 4/2004 | Baker, Jr. et al. |
| 6,739,337 B2 | | 5/2004 | Isaza |
| 6,852,083 B2 | | 2/2005 | Caro et al. |
| 7,160,250 B2 | | 1/2007 | Lemaire |
| 7,231,245 B2 | | 6/2007 | Greenwald et al. |
| 7,285,100 B2 | | 10/2007 | Lemaire |
| 7,455,643 B1 | | 11/2008 | Li et al. |
| 7,547,283 B2 | | 6/2009 | Mourad et al. |
| 7,496,393 B2 | | 11/2009 | Diab et al. |
| 7,647,185 B2 | | 1/2010 | Tarassenko et al. |
| 7,654,964 B1 | | 2/2010 | Kroll et al. |
| 7,668,579 B2 | | 2/2010 | Lynn |
| 7,678,507 B2 | | 3/2010 | Berkow et al. |
| 7,720,516 B2 | | 5/2010 | Chin et al. |
| 7,865,224 B2 | | 1/2011 | Baker, Jr. et al. |
| 7,873,497 B2 | | 1/2011 | Weber et al. |
| 7,887,502 B2 | | 2/2011 | Ross et al. |
| 7,931,559 B2 | | 4/2011 | Baker, Jr. et al. |
| 7,957,780 B2 | | 6/2011 | Lamego et al. |
| 7,976,472 B2 | | 7/2011 | Kiani |
| 8,019,400 B2 | | 9/2011 | Diab et al. |
| 8,463,346 B2 | | 6/2013 | Kuhn et al. |
| 8,512,260 B2 | | 8/2013 | Grudic et al. |
| 8,641,635 B2 | | 2/2014 | Melker et al. |
| 9,603,534 B2 | | 3/2017 | Gabbay et al. |
| 9,757,041 B2 | | 9/2017 | Grudic et al. |
| 10,226,194 B2 | | 3/2019 | Grudic et al. |
| 2001/0027335 A1 | | 10/2001 | Meyerson et al. |
| 2003/0060690 A1 | | 3/2003 | Jelliffe et al. |
| 2003/0125612 A1 | | 7/2003 | Fox et al. |
| 2003/0130570 A1 | | 7/2003 | Krivitski et al. |

(56) References Cited

U.S. PATENT DOCUMENTS

| | | |
|---|---|---|
| 2003/0176931 A1 | 9/2003 | Pednault et al. |
| 2003/0200189 A1 | 10/2003 | Meng et al. |
| 2003/0212678 A1 | 11/2003 | Bloom et al. |
| 2004/0215244 A1 | 10/2004 | Marcovecchio et al. |
| 2004/0242972 A1 | 12/2004 | Adak et al. |
| 2004/0267145 A1 | 12/2004 | David et al. |
| 2005/0015009 A1 | 1/2005 | Mourad et al. |
| 2005/0209516 A1 | 9/2005 | Fraden |
| 2005/0228298 A1 | 10/2005 | Banet et al. |
| 2006/0058691 A1 | 3/2006 | Kiani |
| 2006/0106743 A1 | 5/2006 | Horvitz |
| 2006/0161403 A1 | 7/2006 | Jiang et al. |
| 2006/0166176 A1 | 7/2006 | Lakin et al. |
| 2006/0178585 A1 | 8/2006 | Sharrock |
| 2006/0195041 A1 | 8/2006 | Lynn et al. |
| 2006/0253016 A1 | 11/2006 | Baker, Jr. et al. |
| 2007/0015972 A1 | 1/2007 | Wang et al. |
| 2007/0032732 A1 | 2/2007 | Shelley et al. |
| 2007/0099239 A1 | 5/2007 | Tabibiazar et al. |
| 2007/0112275 A1 | 5/2007 | Cooke et al. |
| 2007/0213619 A1 | 9/2007 | Linder |
| 2008/0039731 A1 | 2/2008 | McCombie et al. |
| 2008/0045845 A1 | 2/2008 | Pfeiffer et al. |
| 2008/0067132 A1 | 3/2008 | Ross et al. |
| 2008/0077023 A1 | 3/2008 | Campbell et al. |
| 2008/0097173 A1 | 4/2008 | Soyemi et al. |
| 2008/0133434 A1 | 6/2008 | Asar et al. |
| 2008/0146890 A1 | 6/2008 | LeBoeuf et al. |
| 2008/0146892 A1 | 6/2008 | LeBoeuf et al. |
| 2008/0154814 A1 | 6/2008 | Chaudhury et al. |
| 2008/0234607 A1 | 9/2008 | Hunter-Jones et al. |
| 2008/0294217 A1 | 11/2008 | Lian et al. |
| 2009/0005703 A1 | 1/2009 | Fasciano |
| 2009/0036754 A1 | 2/2009 | Pons et al. |
| 2009/0069647 A1 | 3/2009 | McNames et al. |
| 2009/0112106 A1 | 3/2009 | Zhang |
| 2009/0143656 A1 | 6/2009 | Manwaring et al. |
| 2009/0149724 A1 | 6/2009 | Mark et al. |
| 2009/0149751 A1 | 6/2009 | Mourad et al. |
| 2009/0204162 A1 | 8/2009 | Addison et al. |
| 2009/0264776 A1 | 10/2009 | Vardy |
| 2009/0272678 A1 | 11/2009 | Sornmo et al. |
| 2009/0281434 A1* | 11/2009 | Messerges ............... A61B 5/02 600/485 |
| 2009/0287105 A1 | 11/2009 | Hirsch |
| 2009/0292198 A1 | 11/2009 | Kleiven et al. |
| 2009/0043222 A1 | 12/2009 | Chetham |
| 2010/0016739 A1 | 1/2010 | Shelley et al. |
| 2010/0041962 A1 | 2/2010 | Causevic et al. |
| 2010/0081942 A1* | 4/2010 | Huiku .................... G16H 40/60 600/483 |
| 2010/0094158 A1 | 4/2010 | Solem et al. |
| 2010/0160795 A1 | 6/2010 | Banet et al. |
| 2010/0191128 A1 | 7/2010 | Shelley et al. |
| 2010/0204589 A1 | 8/2010 | Swoboda et al. |
| 2010/0249559 A1 | 9/2010 | Lovejoy |
| 2011/0077532 A1* | 3/2011 | Kim ...................... A61B 5/0205 600/485 |
| 2011/0112799 A1 | 5/2011 | Weber et al. |
| 2011/0152651 A1 | 6/2011 | Berkow |
| 2011/0160549 A1 | 6/2011 | Saroka et al. |
| 2011/0172545 A1 | 7/2011 | Grudic et al. |
| 2011/0201962 A1 | 8/2011 | Grudic et al. |
| 2011/0282169 A1 | 8/2011 | Grudic et al. |
| 2011/0237914 A1 | 9/2011 | Lamego et al. |
| 2012/0123232 A1 | 5/2012 | Najarian et al. |
| 2012/0136224 A1 | 5/2012 | Najarian et al. |
| 2012/0184840 A1 | 7/2012 | Najarian et al. |
| 2012/0245439 A1 | 9/2012 | Andre' et al. |
| 2012/0269420 A1 | 10/2012 | Najarian et al. |
| 2012/0296219 A1* | 11/2012 | Chon ................. A61B 5/02042 600/479 |
| 2012/0330117 A1 | 12/2012 | Grudic et al. |
| 2013/0041268 A1 | 2/2013 | Rimoldi et al. |
| 2013/0218056 A1 | 8/2013 | Aelen et al. |
| 2013/0245397 A1 | 9/2013 | Grudic et al. |
| 2013/0261468 A1 | 10/2013 | Semler et al. |
| 2013/0343585 A1 | 12/2013 | Bennett et al. |
| 2014/0073938 A1 | 3/2014 | Rodriguez-Llorente et al. |
| 2014/0107437 A1 | 4/2014 | Pinsky |
| 2014/0236053 A1 | 8/2014 | Walker et al. |
| 2015/0065826 A1 | 3/2015 | Mulligan et al. |
| 2015/0073723 A1 | 3/2015 | Mulligan et al. |
| 2015/0141769 A1 | 5/2015 | Mulligan et al. |
| 2016/0015284 A1 | 1/2016 | Grudic et al. |
| 2016/0038042 A1 | 2/2016 | Mulligan et al. |
| 2016/0038043 A1 | 2/2016 | Mulligan et al. |
| 2016/0162786 A1 | 6/2016 | Grudic et al. |
| 2016/0374625 A1 | 12/2016 | Mulligan et al. |
| 2017/0007139 A9 | 1/2017 | Grudic et al. |
| 2017/0215016 A1 | 7/2017 | Dohmen et al. |
| 2017/0258329 A1 | 9/2017 | Marsh |
| 2017/0303799 A1 | 10/2017 | Grudic et al. |
| 2017/0347177 A1 | 11/2017 | Masaki |
| 2018/0214028 A1 | 8/2018 | Zhang et al. |
| 2020/0205734 A1 | 7/2020 | Mulligan et al. |
| 2020/0205747 A1 | 7/2020 | Mulligan et al. |

FOREIGN PATENT DOCUMENTS

| | | |
|---|---|---|
| EP | 3468457 | 4/2019 |
| WO | WO 2003-077854 A2 | 9/2003 |
| WO | WO 2003-091421 A3 | 11/2003 |
| WO | WO-2005-055825 A1 | 6/2005 |
| WO | WO-2005-112756 A1 | 12/2005 |
| WO | WO 2007-011565 A1 | 1/2007 |
| WO | WO 2007-098957 A1 | 9/2007 |
| WO | WO 2007-117570 A2 | 10/2007 |
| WO | WO 2007-149533 A2 | 12/2007 |
| WO | WO 2010-009735 A2 | 1/2010 |
| WO | WO 2010-053743 A1 | 5/2010 |
| WO | WO 2010-117572 A2 | 10/2010 |
| WO | WO 2011-002904 A2 | 1/2011 |
| WO | WO 2011-050066 A2 | 4/2011 |
| WO | WO 2011-103102 A1 | 8/2011 |
| WO | WO 2011-109734 A1 | 9/2011 |
| WO | WO 2012-054880 A2 | 4/2012 |
| WO | WO 2012-166568 A3 | 12/2012 |
| WO | WO 2013-016212 A1 | 1/2013 |
| WO | WO 2014-149981 A1 | 9/2014 |
| WO | WO-2015-042484 A1 | 3/2015 |
| WO | WO 2015-069940 A1 | 5/2015 |
| WO | WO 2015-073909 A1 | 5/2015 |
| WO | WO 2015-073910 A1 | 5/2015 |
| WO | WO 2016-061542 A1 | 4/2016 |
| WO | WO 2016-061545 A1 | 4/2016 |
| WO | WO 2017-044868 A1 | 3/2017 |
| WO | WO-2017-218431 A1 | 12/2017 |

OTHER PUBLICATIONS

EP 11745124.5, Office Action 94(3) dated Jul. 31, 2017, 6 pages.
Kotsiantis (2007) Department of Computer Science and Technology, "Supervised Matchine Learning: A Review of Classification Techniques," 20 pages.
Wu et al., (2009) World Congress on Computer Science and Information Enginerring, "Time Series Mining Approach for Non-invasive Intracranial Pressure Assessment: an Investigation of Different Regularization Techniques," 5 pages.
Extended European Search Report, dated Jun. 7, 2017 for EP14862921.5, 8 pages.
Extended European Search Report, datd Jun. 20, 2017 for EP14859538.2, 8 pages.
International Search Report and Written Opinion prepared by the Korean Intellectual Property Office as International Searching Authority for PCT International Patent Application No. PCT/US2017/037067, dated Aug. 18, 2017, 21 pages.
U.S. Appl. No. 14/535,171, Final Office Action dated Nov. 16, 2017, 30 pages.
U.S. Appl. No. 13/889,513, Non-Final OA, dated Jan. 28, 2020, 27 pages.

(56) References Cited

OTHER PUBLICATIONS

U.S. Appl. No. 14/885,891, Final Office Action dated Mar. 3, 2020, 19 pages.
U.S. Appl. No. 13/889,513, Non-Final Office Action dated Dec. 1, 2017, 51 pages.
U.S. Appl. No. 14/867,938, Non-Final Office Action dated Dec. 8, 2017, 27 pages.
U.S. Appl. No. 13/041,006, Non-Final Office Action dated Dec. 15, 2017, 21 pages.
Canadian Patent Application No. 2,775,675, Non-Final OA dated Sep. 27, 2017; 4 pages.
U.S. Appl. No. 14/542,426, Non-Final Office Action dated Feb. 1, 2018, 19 pages.
U.S. Appl. No. 14/542,423, Non-Final Office Action dated Feb. 5, 2018, 24 pages.
U.S. Appl. No. 14/885,891, Non-Final—OA dated Feb. 5, 2018, 22 pages.
Canadian Patent Application No. 2,871,608, Non-Final OA dated Jan. 25, 2018; 5 pages.
U.S. Appl. No. 14/885,888, Non-Final Office Action dated Mar. 15, 2018, 11 pages.
International Preliminary Report on Patentability prepared by the International Bureau for PCT/US2009/062119, dated Mar. 22, 2018, 9 pages.
U.S. Appl. No. 15/649,411, Non-Final OA dated Apr. 5, 2018, 23 pages.
Extended European Search Report for EP15850241.9, dated Apr. 5, 2018; 8 pages.
U.S. Appl. No. 15/007,489, Non-Final Office Action dated Jun. 13, 2018; 48 pages.
U.S. Appl. No. 14/535,171, Non-FinalOA dated Aug. 9, 2018, 23 pages.
U.S. Appl. No. 14/867,938, Notice of Allowance dated Sep. 6, 2018; 17 pages.
U.S. Appl. No. 13/889,513, Final Office Action dated Sep. 20, 2018, 25 pages.
U.S. Appl. No. 14/542,426, Final Office Action dated Sep. 27, 2018, 11 pages.
U.S. Appl. No. 14/885,888, Final Office Action dated Sep. 28, 2018, 7 pages.
U.S. Appl. No. 14/885,891, Final Office Action dated Sep. 28, 2018, 10 pages.
U.S. Appl. No. 13/041,006, Final Office Action dated Oct. 3, 2018, 9 pages.
U.S. Appl. No. 15/261,661, Non-Final Office Action dated Oct. 12, 2018, 38 pages.
Canadian Patent Application No. 2,871,608, Non-Final OA dated Nov. 22, 2018, 3 pages.
European Patent Application No. 12816832.5, Non-Final OA dated Oct. 12, 2018, 4 pages.
International Preliminary Report on Patentability prepared by the International Bureau for PCT International Patent Application No. PCT/US2017/037067, dated Dec. 27, 2018, 13 pages.
U.S. Appl. No. 14/542,423, Non-Final Office Action dated Dec. 28, 2018, 18 pages.
EPO Communication pursuant to Rules 161(2) and 162 EPC dated Feb. 1, 2019, 4 pages.
Extended European Search Report for EP16845202.7, dated Feb. 1, 2019, 6 pages.
Moulton et al. (2013) Trauma Acute Care Surg 75(6): 1053-1059, "Running on empty? The Compensatory Reserve Index".
Poh et al. (2014) Experimental Physiology, 1421-1426, "Respiratory Pump Contributes to Increased Physiological Reserve for Compensation During Simulated Haemorrhage".
Extended European Search Report Written Opinion for EP16845202.7, dated Mar. 11, 2019, 8 pages.
EPO Communication pursuant to Rule 70(2) and 70(a)(2) EPC, dated Mar. 13, 2019, 1 page.
U.S. Appl. No. 15/007,489, Final Office Action dated Mar. 20, 2019, 36 pages.
U.S. Appl. No. 15/649,411, Non-Final OA dated Apr. 2, 2019, 24 pages.
U.S. Appl. No. 13/041,006, Non-Final OA dated Apr. 4, 2019, 15 pages.
U.S. Appl. No. 14/542,426, Non-Final OA dated Apr. 5, 2019, 9 pages.
U.S. Appl. No. 15/261,661, Final-OA dated Apr. 5, 2019, 19 pages.
U.S. Appl. No. 13/889,513, Restriction Requirement dated Apr. 12, 2019, 9 pages.
U.S. Appl. No. 14/885,888, Non-Final Office Action dated May 15, 2019, 21 pages.
U.S. Appl. No. 14/885,891, Non- Final Office Action dated May 15, 2019, 18 pages.
U.S. Appl. No. 14/535,171, Final-OA dated Jul. 3, 2019, 20, pages.
U.S. Appl. No. 14/542,423, Non-Final Office Action dated Jul. 9, 2019, 17 pages.
Japan Patent Application No. 2017-539521 Office Action, dated Sep. 5, 2019, 7 pages.
EP Application No. 15850241.9, EP Examination Report, dated Oct. 14, 2019, 6 pages.
U.S. Appl. No. 16/726,334, filed Dec. 24, 2019 by Mulligan et al. and entitled "Device-Based Maneuver and Activity State-Based Physiologic Status Monitoring," 89 pages.
U.S. Appl. No. 16/726,337, filed Dec. 24, 2019 by Mulligan et al. and entitled "Ear-Based Physiological State Monitoring" 78 pages.
U.S. Appl. No. 15/649,411, Final OA dated Dec. 23, 2019, 19 pages.
U.S. Appl. No. 14/885,888, Final Office Action dated Jan. 2, 2020, 2019, 21 pages.
U.S. Appl. No. 14/542,426, Final OA dated Dec. 20, 2019, 19 pages.
U.S. Appl. No. 15/261,661, Non-Final Rejection dated Jan. 16, 2020, 20 pages.
U.S. Appl. No. 14/535,171, Non-Final Rejection dated Jan. 23, 2020, 20, pages.
U.S. Appl. No. 13/041,006, Final Rejection dated Jan. 27, 2020; 10 pages.
U.S. Appl. No. 14/542,423, Final Office Action dated May 18, 2020, 21 pages.
U.S. Appl. No. 13/041,006, Non-Final Rejection dated Jun. 12, 2020; 29 pages.
EPO Communication pursuant to Rules 71(3) dated Jun. 23, 2020, 57 pages.
U.S. Appl. No. 15/649,411, Non-Final Office Action, dated Jul. 29, 11 pages.
U.S. Appl. No. 14/885,891, Non-Final Office Action dated Aug. 6, 2020, 19 pages.
U.S. Appl. No. 14/885,888, Non-Final Office Action dated Aug. 6, 2020, 2019, 21 pages.
U.S. Appl. No. 14/542,426, Non-Final Office Action dated Aug. 6, 2020, 2019, 19 pages.
U.S. Appl. No. 15/261,661, Non-Final Rejection dated Sep. 3, 2020, 22 pages.
U.S. Appl. No. 13/889,513, Notice of Abandonment, dated Sep. 25, 2020, 2 pages.
U.S. Appl. No. 14/535,171, Non-Final Office Action dated Oct. 5, 2020, 21 pages.
U.S. Appl. No. 14/542,423, Non-Final Office Action dated Oct. 6, 2020, 21 pages.
U.S. Appl. No. 13/041,006, Final Rejection, dated Jan. 7, 2021; 30 pages.
U.S. Appl. No. 14/885,888, Final Office Action dated Mar. 30, 2021, 25 pages.
U.S. Appl. No. 16/726,337, Non-Final Office Action dated May 17, 2021; 79 pages.
U.S. Appl. No. 15/261,661, Final Office Action dated May 19, 2021, 25 pages.
U.S. Appl. No. 14/535,171, Final Office Action dated May 19, 2021, 22 pages.
U.S. Appl. No. 14/542,423, Final Office Action dated May 19, 2021, 21 pages.
U.S. Appl. No. 15/649,411, Non-Final Office Action, dated May 19, 2021, 21 pages.
U.S. Appl. No. 14/542,426, Final Office Action dated Jun. 1, 2021, 20 pages.

(56) References Cited

OTHER PUBLICATIONS

U.S. Appl. No. 14/885,891, Non-Final Office Action, dated Jun. 8, 2021, 23 pages.
U.S. Appl. No. 13/041,006, Non-Final Office Action dated Jul. 16, 2021; 32 pages.
International Search Report and Written Opinion prepared by the U.S. Patent and Trademark Office as International Searching Authority for PCT International Patent Application No. PCT/US09/62119, dated Feb. 3, 2010, 5 pages.
International Preliminary Reporton Patentability prepared by the International Bureau for PCT/US2009/062119, dated May 12, 2011, 6 pages.
Decision to Grant, dated Apr. 23, 2015 for EP 09825222.4, 3 pages.
European Search Report, dated Jun. 15, 2012 for EP 09825222.4, 10 pages.
Procopio et al. (2008) Intelligent Robots And Systems IEEE/RSJ International Conference, pp. 620-627, "Learning in 1-14 dynamic environments with Ensemble Selection for autonomous outdoor robot navigation".
Shoemaker, et al. (2001) CHEST, 120(2):528-538, "Outcome Prediction of Emergency Patients by Noninvasive Hemodynamic Monitoring".
Supplemental European Search Report, dated Jul. 3, 2012 for EP 09825222.4, 1 page.
U.S. Appl. No. 13/126,727, filed Apr. 28, 2011 by Grudic et al. and entitled "Long Term Active Learning from Large Continually Changing Data Sets," 181 pages.
U.S. Appl. No. 13/126,727, NonFinal Office Action dated Sep. 11, 2014; 58 pages.
U.S. Appl. No. 13/126,727, Notice of Publication dated Nov. 17, 2011; 1 page.
U.S. Appl. No. 13/028,140, NonFinal Office Action dated Nov. 13, 2012; 27 pages.
U.S. Appl. No. 13/028,140, Notice of Allowance datet Feb. 22, 2013; 22 pages.
U.S. Appl. No. 13/028,140, Notice of Publication dated Aug. 18, 2011; 1 page.
U.S. Appl. No. 13/028,140, Restriction Requirement dated Aug. 1, 2012; 7 pages.
U.S. Appl. No. 13/028,140, filed Feb. 15, 2011 by Grudic et al. and entitled, "Statistical, Noninvasive Measurement of Intracranial Pressure" 41 pages.
U.S. Appl. No. 13/889,513, Notice of Publicatior dated Sep. 19, 2013; 1 page.
U.S. Appl. No. 13/889,513, filed May 8, 201 by Grudic et al. and entitled "Statistical, Noninvasive Measurement of Intracranial Pressure," 35 pages.
U.S. Appl. No. 13/889,513, NonFinal Office Action dated Jun. 15, 2015, 27 pages.
International Preliminary Report on Patentability prepared by the International Bureau for PCT/US11/24938, dated Aug. 30, 2012, 7 pages.
International Search Report and Written Opinion prepared by the U.S. Patent and Trademark Office as International Searching Authority for PCT International Patent Application No. PCT/US2011/24938, dated Jun. 7, 2011, 13 pages.
Supplemental European Search Report, dated Jun. 21, 2013 for EP 11745124.5, 7 pages.
U.S. Appl. No. 13/041,006, filed Mar. 4, 2011 by Grudit et al. and entitled "Active Physical Perturbations to Enhance Intelligent Medical Monitoring" 47 pages.
U.S. Appl. No. 13/041,006, NonFinal Office Action dated May 23, 2014; 27 pages.
U.S. Appl. No. 13/041,006, NonFinal Office Action dated Dec. 22, 2014; 14 pages.
U.S. Appl. No. 13/041,006, Notice of Publication dated Jul. 14, 2011; 1 page.
International Preliminary Report on Patentability prepared by the International Bureau for PCT/US11/27237, dated Sep. 13, 2012, 10 pages.
International Search Report and Written Opinion prepared by the U.S. Patent and Trademark Office as International Searching Authority for PCT International Patent Application No. PCT/US2011/027237, dated May 27, 2011, 16 pages.
Cooke et al. (2004) Journal of Applied Physiology 96(4): 1249-1261, "Lower body negative pressure as a model to study progression to acute hemorrhagic shock in humans".
Extended European Search Report, Oct. 18, 2013 for EP11751440.6, 7 pages.
Lambert et al. (2007) ACTA Anaesthesiologica Scandinavica 51(4):415-425, "Does a positive 1-27 end-expiratory pressure-induced reduction in stroke vol. indicate preload responsiveness? An experimental study".
Ryan et al. (2008) Journal of Applied Physiology 104(5):1402-1409, "Breathing through an inspiratory threshold device improves stroke volume during central hypovolemia in humans".
Supplemental Extended European Search Report, Nov. 6, 2013 for EP11751440.6, 8 pages.
U.S. Appl. No. 13/554,483, filed Jul. 20, 2012 by Grudic et al. and entitled "Hemodynamic Reserve Monitor and Hemodialysis Control," 57 pages.
International Preliminary Report on Patentability prepared by the International Bureau for PCT International Patent Application No. PCT/US12/047659, dated Feb. 6, 2014, 10 pages.
International Search Report and Written Opinion prepared by the U.S. Patent and Trademark Office as International Searching Authority for PCT International Patent Application No. PCT/US12/47659, dated Oct. 12, 2012, 16 pages.
Extended European Search Report for EP 12816832.5, dated Oct. 6, 2014, 9 pages.
U.S. Appl. No. 14/535,171, Notice of Publication dated Mar. 5, 2015; 1 page.
International Search Report and Written Opinion prepared by the Korean Intellectual Propert Office as International Searching Authority for PCT International Patent Application No. PCT/US2014/064413, dated Feb. 12, 2015, 13 pages.
International Patent Application No. PCT/US14/64413, Notice of Publication dated May 14, 2015; 1 page.
U.S. Appl. No. 14/542,423, Notice of Publication dated May 21, 2015; 1 page.
International Search Report and Written Opinion prepared by the Korean Intellectual Properl Office as International Searching Authority for PCT International Patent Application No. PCT/US2014/065818, dated Feb. 26, 2015, 14 pages.
U.S. Appl. No. 14/542,426, Notice of Publication dated Mar. 12, 2015; 1 page.
International Search Report and Written Opinion prepared by the Korean Intellectual Properl Office as International Searching Authority for PCT International Patent Application No. PCT/US2014/065820, dated Feb. 26, 2015, 14 pages.
Berkow (Aug. 2010) Intelomed, Inc., "CVInsight," 14 pages.
Berkow (Jan. 2012) 510(K) Summary, "CVInsight," 9 pages.
Najarian (2012) VCU School of Engineering ResearchReport, vol. 5, p. 3.
U.S. Appl. No. 13/126,727, Final Rejection dated Aug. 27, 2015; 33 pages.
U.S. Appl. No. 13/041,006, Final Rejection dated Sep. 15, 2015; 19 pages.
Canadian Patent Application No. 2,775,675, NonFinalOA dated Dec. 9, 2015; 3 pages.
International Search Report and Written Opinion prepared by the Korean Intellectual Properl Office as International Searching Authority for PCT International Patent Application No. PCT/US2015/056078, dated Jan. 25, 2016, 11 pages.
U.S. Appl. No. 14/867,938, Notice of Publication dated Jan. 21, 2016; 1 page.
International Search Report and Written Opinion prepared by the Korean Intellectual Property Office as International Searching Authority for PCT International Patent Application No. PCT/US2015/56074, dated Jan. 29, 2016, 13 pages.

(56) References Cited

OTHER PUBLICATIONS

Convertino, Victor, "Estimation of individual-specific progression to impending cardiovascular stability using arterial waveforms," Journal of Applied Physiology, Oct. 15, 2013, vol. 15, No. 8, pp. 1196-1202.
U.S. Appl. No. 14/885,888, Notice of Publication dated Feb. 11, 2016; 1 page.
U.S. Appl. No. 14/885,891, Notice of Publication dated Feb. 11, 2016; 1 page.
U.S. Appl. No. 14/542,426, Non-Final Office Action dated Feb. 26, 2016; 25 pages.
U.S. Appl. No. 13/554,483, Non-Final Office action dated Mar. 22, 2016; 41 pages.
EP11751440.6, Office Action 94(3) dated Feb. 24, 1016, 5 pages.
International Patent Application No. PCT/US15/56074, Notice of Publication dated Apr. 21, 2016; 1 page.
International Patent Application No. PCT/US15/56078, Notice of Publication dated Apr. 21, 2016; 1 page.
U.S. Appl. No. 13/041,006, Non-final Office Action dated Apr. 22, 2016, 15 pages.
International Preliminary Report on Patentability prepared by the International Bureau for PCT International Patent Application No. PCT/US14/064413, dated May 19, 2016, 10 pages.
International Preliminary Report on Patentability prepared by the International Bureau for PCT International Patent Application No. PCT/US14/65818, dated May 26, 2016, 11 pages.
International Preliminary Report on Patentability prepared by the International Bureau for PCT International Patent Application No. PCT/US14/65820, dated May 26, 2016, 11 pages.
U.S. Appl. No. 15/007,489, Notice of Publication dated Jun. 9, 2016; 1 page.
Stewart et al. (2016) PubMed Epub ahead of print, "The Compensatory Reserve Index Allowing Injury: Results of a Prospective Clinical Trial" 2 pages.
U.S. Appl. No. 14/542,426, Final Office Action dated Sep. 26, 2016, 25 pages.
Intravenous Therapy (Wikipedia) Accessed on: Sep. 27, 2016, 12 pages.
U.S. Appl. No. 13/554,483, Final Office Action dated Oct. 7, 2016, 28 pages.
International Search Report and Written Opinion prepared by the Korean Intellectual Property Office as International Searching Authority for PCT International Patent Application No. PCT/US2016/051130, dated Dec. 8, 2016, 14 pages.
U.S. Appl. No. 14/535,171, NonFinalOA dated Dec. 16, 2016, 37 pages.
U.S. Appl. No. 14/885,888, NonFinalOA dated Dec. 16, 2016, 35 pages.
U.S. Appl. No. 15/261,661, Notice of Publication dated Dec. 29, 2016; 1 page.
U.S. Appl. No. 13/889,513, Notice of Publication dated Jan. 12, 2017; 1 page.
Nadler et al. 2014, Shock 42(2): 93-98, "The Value of Noninvasive Measurement of the Compensatory Reserve Index in Monitoring and Triage of Patients Experiencing Minimal Blood Loss".
Nadler et al. 2017, Annals of Medicine and Surgery, "The approximated cardiovascular reserve index complies with haemorrhage related hemodynamic deterioration pattern: A swine exsanguination model" 7 pages.
Canadian Patent Application No. 2,775,675, NonFinalOA dated Nov. 9, 2016; 4 pages.
U.S. Appl. No. 13/041,006, FinalOA dated Mar. 7, 2017, 21 pages.
U.S. Appl. No. 13/554,483, Notice of Allowance dated Mar. 7, 2017, 39 pages.
International Patent Application No. PCT/US16/51130, Notice of Publication dated Mar. 16, 2017; 1 page.
U.S. Appl. No. 13/889,513, Final Rejection dated Apr. 11, 2017; 51 pages.
Schmidt et al. (1997) Stroke, "Noninvasive Prediction of Intracranial Pressure Curves Using Transcranial Doppler Ultrasonography and Blood Pressure Curves," 22 pages.
International Preliminary Report on Patentability prepared by the International Bureau for PCT/US15/56074, dated Apr. 27, 2017, 10 pages.
International Preliminary Report on Patentability prepared by the International Bureau for PCT/US15/56078, dated Apr. 27, 2017, 7 pages.
U.S. Appl. No. 14/542,426, Non-Final Office Action dated May 5, 2017; 17 pages.
U.S. Appl. No. 14/542,423, NonFinal Office Action dated May 8, 2017; 35 pages.
U.S. Appl. No. 14/885,891, NonFinalOA dated May 8, 2017; 29 pages.
Extended European Search Report for EP14862697.1, dated Jun. 14, 2017; 8 pages.
U.S. Appl. No. 14/885,888, Non-Final Office Action, dated Dec. 24, 2021, 28 pages.
U.S. Appl. No. 14/885,891, Final Office Action, dated Dec. 24, 2021, 24 pages.
U.S. Appl. No. 13/041,006, Final Office Action, dated Jan. 27, 2022; 32 pages.
U.S. Appl. No. 15/649,411, Notice of Allowance, dated Feb. 2, 2022, 30 pages.
U.S. Appl. No. 14/535,171, Notice of Allowance, dated Feb. 9, 2022, 30 pages.
U.S. Appl. No. 15/261,661, Notice of Allowance, dated Mar. 10, 2022; 48 pages.
U.S. Appl. No. 14/542,423, Notice of Allowance, dated Mar. 16, 2022; 29 pages.

* cited by examiner the

RAPID DETECTION OF BLEEDING FOLLOWING INJURY

CROSS-REFERENCE TO RELATED APPLICATIONS

This application claims the benefit, under 35 U.S.C. § 119(e), of provisional U.S. Patent Application No. 62/349,516, filed Jun. 13, 2016 by Mulligan et al. and entitled "Rapid Detection of Bleeding Following Injury", referred to herein as the "'516 Application"), which is hereby incorporated by reference in its entirety.

This application is also a continuation-in-part application of U.S. patent application Ser. No. 15/261,661, filed Sep. 9, 2016 by Mulligan et al. and entitled "Estimating Physiological States Based on Changes in CRT", referred to herein as the "'661 Application"), which claims priority to the '516 Application and to provisional U.S. Patent Application No. 62/216,187, filed Sep. 9, 2015 by Mulligan et al. and entitled "Estimating Physiological States Based on Changes in CRT", referred to herein as the "'187 Application"), each of which is incorporated herein by reference in its entirety. This application is also a continuation-in-part application of U.S. patent application Ser. No. 14/885,891, filed Oct. 16, 2015 by Mulligan et al. and entitled "Assessing Effectiveness of CPR", referred to herein as the "'891 Application"), which is incorporated herein by reference in its entirety. This application is also a continuation-in-part application of U.S. patent application Ser. No. 14/885,888, filed Oct. 16, 2015 by Mulligan et al. and entitled "Rapid Detection of Bleeding Before, During, and After Fluid Resuscitation", referred to herein as the "'888 Application"), which is incorporated herein by reference in its entirety and which claims priority to provisional U.S. Patent Application No. 62/064,816, filed Oct. 16, 2014 by Mulligan et al. and titled "Assessing the Effectiveness of CPR" and provisional U.S. Patent Application No. 62/064,809 filed Oct. 16, 2014 by Mulligan et al. and titled "Rapid Detection of Bleeding During Fluid Resuscitation", each of which are incorporated herein by reference in their entirety.

The '888 Application is a continuation-in-part application of U.S. patent application Ser. No. 14/542,426, filed Nov. 14, 2014 by Mulligan et al. and titled, "Noninvasive Hydration Monitoring", referred to herein as the "'426 Application"), which is incorporated herein by reference in its entirety. The '888 Application is also a continuation-in-part application of U.S. patent application Ser. No. 14/542,423, filed Nov. 14, 2014 by Mulligan et al. and titled, "Noninvasive Monitoring for Fluid Resuscitation", referred to herein as the "'423 Application"), which is incorporated herein by reference in its entirety and which claims priority to provisional U.S. Patent Application No. 61/905,727, filed Nov. 18, 2013 by Mulligan et al. and titled "Noninvasive Hydration Monitoring", referred to herein as the "'436 Application") and provisional U.S. Patent Application No. 61/904,436, filed Nov. 14, 2013 by Mulligan et al. and titled "Noninvasive Monitoring for Fluid Resuscitation", referred to herein as the "'436 Application"), each of which are incorporated herein by reference in their entirety.

The '423 Application is a continuation-in-part application of U.S. patent application Ser. No. 14/535,171, filed Nov. 6, 2014 by Mulligan et al. and titled "Noninvasive Predictive and/or Estimative Blood Pressure Monitoring", referred to herein as the "'171 Application"), which is incorporated herein by reference in its entirety and which claims priority to provisional U.S. Patent Application No. 61/900,980, filed Nov. 6, 2013 by Mulligan et al. and titled "Noninvasive Predictive and/or Estimative Blood Pressure Monitoring", which is incorporated herein by reference in its entirety.

The '171 Application is a continuation-in-part application of U.S. patent application Ser. No. 13/554,483, filed Jul. 20, 2012 by Grudic et al. and titled, "Hemodynamic Reserve Monitor and Hemodialysis Control", referred to herein as the "'483 Application"), which is hereby incorporated by reference in its entirety and which claims priority to provisional U.S. Patent Application No. 61/510,792, filed Jul. 22, 2011 by Grudic et al. and entitled "Cardiovascular Reserve Monitor" and provisional U.S. Patent Application No. 61/614,426, filed Mar. 22, 2012 by Grudic et al. and entitled "Hemodynamic Reserve Monitor and Hemodialysis Control", both of which are hereby incorporated by reference in its entirety.

The '483 Application is a continuation-in-part application of U.S. patent application Ser. No. 13/041,006, filed Mar. 4, 2011 by Grudic et al. and entitled "Active Physical Perturbations to Enhance Intelligent Medical Monitoring", referred to herein as the "'006 Application"), which is hereby incorporated by reference in its entirety and which claims priority to provisional U.S. Patent Application No. 61/310,583, filed Mar. 4, 2010 by Grudic et al. and titled "Active Physical Perturbations to Enhance Intelligent Medical Monitoring", which is hereby incorporated by reference in its entirety.

The '006 Application is a continuation-in-part application of U.S. patent application Ser. No. 13/028,140, filed Feb. 15, 2011 by Grudic et al. and entitled "Statistical, Noninvasive Measurement of Intracranial Pressure", referred to herein as the "'140 Application"; now issued U.S. Pat. No. 8,512,260), which is hereby incorporated by reference in its entirety and which claims priority to provisional U.S. Patent Application No. 61/305,110, filed Feb. 16, 2010, by Moulton et al. and titled "Statistical, Noninvasive Method for Measuring Intracranial Pressure", which is hereby incorporated by reference in its entirety.

The '140 Application is a continuation-in-part application of International Application No. PCT/US2009/062119, filed Oct. 26, 2009 by Grudic et al. and entitled "Long Term Active Learning from Large Continually Changing Data Sets" (the "'119 Application"), which is hereby incorporated by reference in its entirety and which claims priority to provisional U.S. Patent Application No. 61/252,978 filed Oct. 19, 2009 by Grudic et al. and titled "Long Term Active Learning from Large Continually Changing Data Sets," provisional U.S. Patent Application No. 61/166,499, filed Apr. 3, 2009 by Moulton and titled "Advances in Pre-Hospital Care," provisional U.S. Patent Application No. 61/166,486, filed Apr. 3, 2009 by Grudic et al. and titled "Statistical Methods for Predicting Patient Specific Blood Loss Volume Causing Hemodynamic Decompensation," provisional U.S. Patent Application No. 61/166,472, filed Apr. 3, 2009 by Grudic et al. and titled "Long Term Active Learning from Large Continually Changing Data Sets," and provisional U.S. Patent Application No. 61/109,490, filed Oct. 29, 2008 by Moulton et al. and titled "Method for Determining Physiological State or Condition," each of which is hereby incorporated by reference in its entirety.

STATEMENT AS TO RIGHTS TO INVENTIONS MADE UNDER FEDERALLY SPONSORED RESEARCH OR DEVELOPMENT

This invention was made with government support under grant number 0535269 awarded by the National Science Foundation; grant number FA8650-07-C-7702 awarded by the Air Force Research Laboratory; and grant numbers W81XWH-09-C-1060, W81XWH-09-1-0750, W81XWH-11-2-0091, W81XWH-11-2-0085, W81XWH-12-2-0112, W81XWH-13-CCCJPC6, and W81XWH-13-C-0121 awarded by Army Medical Research and Materiel Command Combat Casualty Research Program, and the US Army Small Business Innovative Research (SBIR) program. The government has certain rights in the invention.

The respective disclosures of these applications/patents (collectively, the "Related Applications"), which are commonly assigned, are incorporated herein by reference in their entirety for all purposes.

COPYRIGHT STATEMENT

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

FIELD

The present disclosure relates, in general, tools and techniques for medical monitoring, and more particularly, to tools and techniques that can provide rapid detection of bleeding following injury.

BACKGROUND

Hemorrhagic shock induced by traumatic injury is a leading cause of mortality. The first hour following injury has been termed the "golden hour," because there is a short interval of time during which recognition and proper management of a patient with significant, ongoing bleeding can make the difference between life and death. Significant bleeding is not always clinically evident. Many severely injured patients have intracavitary bleeding, which means that bleeding from a major organ or vessel is contained within the thorax or abdomen. There is no external evidence of bleeding and as a result, suspicion and clinical signs of bleeding must be sought by the practitioner. In the field, where imaging and laboratory tests are generally not available, a change in vital signs over time may be the only indication that a patient is bleeding. Thus, during the "golden hour" one must learn to recognize the signs and symptoms of acute blood loss, then initiate fluid resuscitation and frequently estimate the patient's fluid needs in an ongoing fashion.

The problem is that humans are unable to recognize subtle, beat-to-beat vital sign changes that are indicative of bleeding. More importantly, humans are unable to detect subtle vital sign changes that lead to and are characteristic of impending hemodynamic decompensation or cardiovascular collapse, which is heralded by hypotension with bradycardia.

To further complicate matters, humans have an innate ability to compensate for significant blood loss with little change in traditional vital signs. Accordingly, blood loss is difficult to detect using traditional vital sign monitoring techniques.

Thus, there is a need for an automated, noninvasive device for early diagnosis, real-time monitoring and tracking of blood loss, especially following injury.

BRIEF DESCRIPTION OF THE DRAWINGS

A further understanding of the nature and advantages of particular embodiments may be realized by reference to the remaining portions of the specification and the drawings, in which like reference numerals are used to refer to similar components. In some instances, a sub-label is associated with a reference numeral to denote one of multiple similar components. When reference is made to a reference numeral without specification to an existing sub-label, it is intended to refer to all such multiple similar components.

DETAILED DESCRIPTION OF CERTAIN EMBODIMENTS

Overview

Figure 1A:
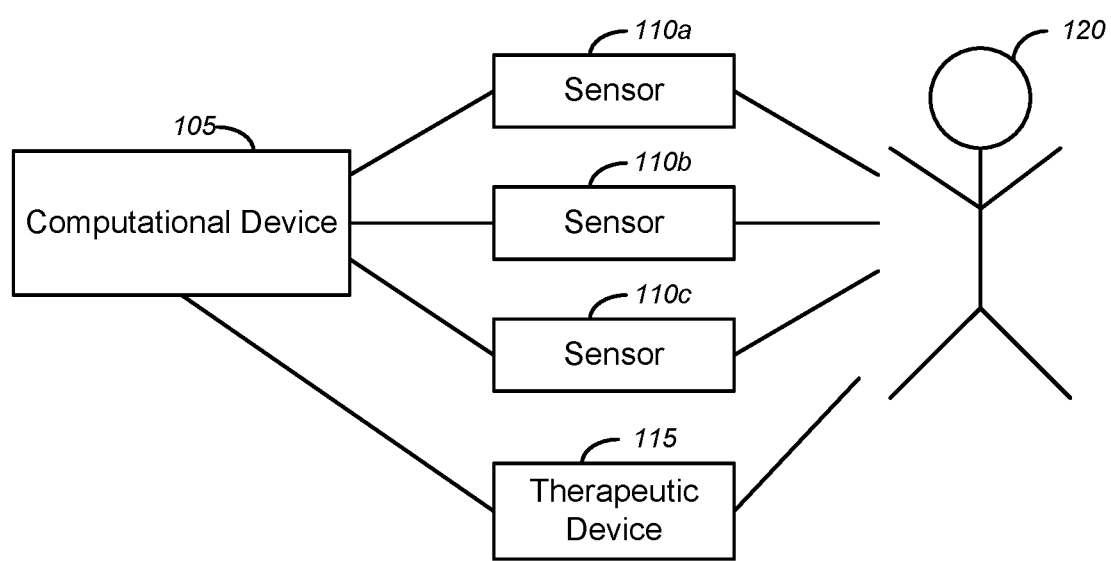
FIG. 1A is a schematic diagram illustrating a system for estimating compensatory reserve, in accordance with various embodiments.

Various embodiments can detect bleeding in patients following injury, in some instances, in real-time before, during, and after fluid resuscitation. In an aspect, such detection can be performed noninvasively. In some embodiments, the detection can be based on a calculation (or estimation) of a patient's compensatory reserve index ("CRT," also referred to herein and in the Related Applications as "cardiac reserve index" or "hemodynamic reserve index" ("HDRI")). In other cases, the assessments might be based on raw waveform data (e.g., PPG waveform data) captured by a sensor on the patient (such as the sensors described in the Related Applications, for example). In further cases, a combination of waveform data and calculated/estimated CRT can be used to calculate the effectiveness of resuscitation and/or the amount of fluid needed for effective resuscitation.

In other aspects, such functionality can be provided by and/or integrated with systems and devices (such as a cardiac reserve monitor), tool, techniques, methods, and software described in the Related Applications, including in particular the '483 Application. For example, various operations described in accordance with the methods disclosed by the Related Applications can be employed in a method of assessing effectiveness of resuscitation and/or calculating an amount of fluid needed for effective resuscitation. Similarly, such techniques can be performed by the systems and/or embodied by the software products described in the Related Applications.

An embodiment can include a system that comprises one or more sensors placed on the patient and a computer system (such as those described in the Related Applications) that performs a method for using sensor data for estimating and predicting (in real-time, after every heartbeat, or as the information is needed) one or more of the relevant parameters outlined above. Other embodiments can comprise the computer system programmed to perform such a method, an apparatus comprising instructions to program a computer to perform such a method, and/or such a method itself.

A sensor may include, but is not limited to, any of the following: a noninvasive blood pressure sensor such as the Nexfin (BMEYE, B.V.) or Finometer (Finapres Medical Systems B.V.); invasive arterial blood pressure, using an arterial catheter; invasive central venous pressure; invasive or noninvasive intracranial pressure monitor; electroencephalograph ("EEG"); cardiac monitor ("EKG"); transcranial Doppler sensor; transthoracic impedance plethysmography; pulse oximetry; a sensor generating a photoplethysmograph ("PPG") waveform; near infrared spectroscopy; electronic stethoscope; and/or the like.

The '809 Application describes several exemplary embodiments, but various embodiments are not limited to those described in the '809 Application. For example, FIG. 1 of the '809 Application illustrates an exemplary sensor that can be used to collect waveform data for analysis, but other sensors could be used as well. Similarly, the '809 Application describes several techniques for estimating probability of blood loss. Many such techniques depend on an estimate of a patient's CRI, which can be calculated using the techniques described in the '483 Application. It should be appreciated, however, that other embodiments of estimating a probability of bleeding and/or of estimating CRI can be employed in various embodiments.

Thus, in one aspect, a method can include receiving data from such a sensor and analyzing such data using techniques including, but not limited to, analyzing the data using models described in the Related Applications. Merely by way of example, a model might be constructed using test subject data from a study, such as the LBNP study, which can be used to predict or estimate a CRI (or HDRI) value, as described in the Related Applications, and in particular in the '483 Application. From this calculated value of CRI (or, in some embodiments, from the waveform data itself, alone or in combination with the CRI value), a probability that a patient is bleeding internally before, during, and/or after fluid resuscitation procedures, for example, using the techniques described in the '809 Application.

For example, in one embodiment, a method might comprise capturing waveform data from a patient with the sensor before, during, and/or after fluid resuscitation and/or calculating a CRI value for the patient at these times. In some cases, the variation in CRI values obtained during the procedure can be used to estimate a probability that the patient is bleeding. For instance, the standard deviation of the CRI values during the recording and/or the difference in CRI values before, during, and/or after fluid resuscitation can be used to estimate probability of bleeding, as described more fully with regard to the clinical study detailed in the '809 Application.

Some embodiments further comprise normalizing an estimated probability of bleeding against a scaling. For example, in some cases, an index from 0 to 1 could be used, with 0 indicating that the patient is not bleeding, 1 indicating that the patient is bleeding, and values between 0 and 1 indicating relative probabilities that the patient is bleeding, based on the estimates calculated from the CRI values.

The following detailed description illustrates a few exemplary embodiments in further detail to enable one of skill in the art to practice such embodiments. The described examples are provided for illustrative purposes and are not intended to limit the scope of the invention. For the purposes of this disclosure, it should be recognized that a node could be "virtual" or supported on a hypervisor or Host system, or could be a physical node or network device within a network. In most cases, the figures illustrate bridging a virtual path and possibly a node (virtual machine) across the path or between two physical nodes. However, it should be understood that the "swapping" of paths via orchestration can occur in any combination of physical and/or virtual nodes, physical and/or virtual links, or the like.

In the following description, for the purposes of explanation, numerous specific details are set forth in order to provide a thorough understanding of the described embodiments. It will be apparent to one skilled in the art, however, that other embodiments of the present invention may be practiced without some of these specific details. In other instances, certain structures and devices are shown in block diagram form. Several embodiments are described herein, and while various features are ascribed to different embodiments, it should be appreciated that the features described with respect to one embodiment may be incorporated with other embodiments as well. By the same token, however, no single feature or features of any described embodiment should be considered essential to every embodiment of the invention, as other embodiments of the invention may omit such features.

Unless otherwise indicated, all numbers used herein to express quantities, dimensions, and so forth used should be understood as being modified in all instances by the term "about." In this application, the use of the singular includes the plural unless specifically stated otherwise, and use of the terms "and" and "or" means "and/or" unless otherwise indicated. Moreover, the use of the term "including," as well as other forms, such as "includes" and "included," should be considered non-exclusive. Also, terms such as "element" or "component" encompass both elements and components comprising one unit and elements and components that comprise more than one unit, unless specifically stated otherwise.

The tools provided by various embodiments include, without limitation, methods, systems, and/or software products. Merely by way of example, a method might comprise one or more procedures, any or all of which are executed by a computer system. Correspondingly, an embodiment might provide a computer system configured with instructions to perform one or more procedures in accordance with methods provided by various other embodiments. Similarly, a computer program might comprise a set of instructions that are executable by a computer system (and/or a processor therein) to perform such operations. In many cases, such software programs are encoded on physical, tangible, and/or non-transitory computer readable media (such as, to name but a few examples, optical media, magnetic media, and/or the like).

In an aspect, a system might be provided that comprises one or more sensors to obtain physiological data from a patient and a computer system in communication with the one or more sensors. The computer system might comprise one or more processors and a non-transitory computer readable medium in communication with the one or more processors. The computer readable medium might have encoded thereon a set of instructions executable by the one or more processors to cause the computer system to receive the physiological data from the one or more sensors before, during, and after resuscitation following injury, analyze the physiological data, estimate a probability that the patient is bleeding, and display, on a display device, at least one of an assessment, prediction, or estimate indicating a probability that the patient is bleeding.

In another aspect, a method might be provided that comprises monitoring, with one or more sensors, physiological data of a patient before, during, and after resuscitation following injury, analyzing, with a computer system, the physiological data, and estimating, with the computer system, a probability that the patient is bleeding, based at least in part on the analyzed physiological data. The method might further comprise displaying, with the computer system and on a display device, an indication of at least one of an assessment, prediction, or estimate of a probability that the patient is bleeding.

According to some embodiments, resuscitation might comprise at least one of infusing crystalloid in the patient, infusing blood products in the patient, or infusing intravenous fluid in the patient, and/or the like. In some instances, the intravenous fluid might comprise one or more of saline solution or lactated ringer's ("LR") solution, and/or the like. In some cases, the blood products might comprise one or more of infusion of packed red blood cells ("PRBC") in the patient, infusion of fresh frozen plasma ("FFP") in the patient, infusion of platelets ("PLTs") in the patient, or infusion of cryoprecipitated antihaemophilic factor ("cryo") in the patient, and/or the like.

In some instances, one or more of monitoring the physiological data, analyzing the physiological data, estimating the probability that the patient is bleeding, or displaying the indication of at least one of an assessment, prediction, or estimate of the probability that the patient is bleeding are performed in real-time. In some cases, estimating a probability that the patient is bleeding might comprise estimating, with the computer system, a probability that the patient is bleeding, based at least in part on one or more values of compensatory reserve index ("CRT") estimated based on the received physiological data (i.e., the physiological data that are received by the computer system from the one or more sensors). According to some embodiments, the one or more values of CRT are estimated based on physiological data that are at least one of received before, received during, or received after a fluid resuscitation procedure.

In some embodiments, the one or more values of CRT might comprise a plurality of values of CRT. In some cases, estimating a probability that the patient is bleeding might comprise estimating, with the computer system, the probability that the patient is bleeding based at least in part on one or more of an average value of CRI over a particular period of time, a standard deviation of at least some of the plurality of values of CRI, a skewness of at least some of the plurality of values of CRI, a rate of change of at least some of the plurality of values of CRI, a rate of rate change of at least some of the plurality of values of CRI, and/or a difference between at least some of the plurality of values of CRI. In some instances, the indication is a value between 0 and 1. According to some embodiments, a value of 1 might indicate that the patient is not bleeding, while a value of 0 might indicate that the patient is bleeding.

In some cases, estimating a CRI of the patient comprises estimating a compensatory reserve index by comparing the physiological data to a model constructed using the following formula:

$$CRI(t) = 1 - \frac{BLV(t)}{BLV_{HDD}},$$

where CRI(t) is the compensatory reserve at time t, BLV(t) is an intravascular volume loss of a test subject at time t, and $BLV_{HDD}$ is an intravascular volume loss at a point of hemodynamic decompensation of the test subject. In some embodiments, the physiological data comprises waveform data and wherein estimating the CRI comprises comparing, with the computer system, the waveform data with one or more sample waveforms generated by exposing one or more test subjects to state of hemodynamic decompensation or near hemodynamic decompensation, or a series of states progressing towards hemodynamic decompensation, and monitoring physiological data of the test subjects.

In some instances, the physiological data might comprise waveform data, and estimating the CRI might comprise comparing, with the computer system, the waveform data with a plurality of sample waveforms, each of the sample waveforms corresponding to a different value of the CRI to produce a similarity coefficient expressing a similarity between the waveform data and each of the sample waveforms; normalizing, with the computer system, the similarity coefficients for each of the sample waveforms; and summing, with the computer system, the normalized similarity coefficients to produce an estimated CRI value for the patient.

According to some embodiments, estimating a probability that the patient is bleeding is based at least in part on a fixed time history of monitoring the physiological data of the patient. Alternatively, estimating a probability that the patient is bleeding is based at least in part on a dynamic time history of monitoring the physiological data of the patient.

In some instances, at least one of the one or more sensors each comprises at least one of a blood pressure sensor, an intracranial pressure monitor, a central venous pressure monitoring catheter, an arterial catheter, an electroencephalograph, a cardiac monitor, a transcranial Doppler sensor, a transthoracic impedance plethysmograph, a pulse oximeter, a near infrared spectrometer, a ventilator, an accelerometer, an electrooculogram, a transcutaneous glucometer, an electrolyte sensor, or an electronic stethoscope, and/or the like.

Merely by way of example, in some embodiments, physiological data might comprise at least one of blood pressure waveform data, plethysmograph waveform data, or photoplethysmograph ("PPG") waveform data.

In some cases, analyzing the physiological data might comprise analyzing, with the computer system, the physiological data against a pre-existing model. In some embodiments, the method might further comprise generating, with the computer system, the pre-existing model prior to analyzing the physiological data. In some instances, generating the pre-existing model might comprise receiving, with the computer system, data pertaining to one or more physiological parameters of a test subject to obtain a plurality of physiological data sets, directly measuring one or more physiological states of the test subject with a reference sensor to obtain a plurality of physiological state measurements, and correlating, with the computer system, the received data with the physiological state measurements of the test subject. According to some embodiments, the one or more physiological states comprise reduced circulatory system volume.

In some instances, the method might further comprise inducing the physiological state of reduced circulatory system volume in the test subject. In some cases, inducing the physiological state might comprise at least one of subjecting the test subject to lower body negative pressure ("LBNP"), subjecting the test subject to dehydration, and/or the like. In some embodiments, the one or more physiological states might comprise at least one of a state of cardiovascular collapse or near-cardiovascular collapse, a state of euvolemia, a state of hypervolemia, a state of dehydration, and/or the like.

According to some embodiments, correlating the received data with the physiological state measurements of the test subject might comprise identifying, with the computer system, a most predictive set of signals $S_k$ out of a set of signals $s_1, s_2, \ldots, s_D$ for each of one or more outcomes $o_k$, autonomously learning, with the computer system, a set of probabilistic predictive models $ô_k = M_k(S_k)$, and repeating, with the computer system, the operation of autonomously learning incrementally from data that contains examples of values of signals $s_1, s_2, \ldots, s_D$ and corresponding outcomes $o_1, o_2, \ldots, o_K$. Here, the most-predictive set of signals $S_k$ corresponds to a first data set representing a first physiological parameter, and each of the one or more outcomes $o_k$ represents a physiological state measurement, while $ô_k$ is a prediction of outcome $o_k$ derived from a model $M_k$ that uses as inputs values obtained from the set of signals $S_k$.

In yet another aspect, an apparatus might be provided that comprises a non-transitory computer readable medium that has encoded thereon a set of instructions executable by one or more computers to cause the apparatus to receive physiological data from one or more sensors before, during, and after resuscitation following injury, analyze the physiological data, estimate a probability that the patient is bleeding, and display, on a display device, at least one of an assessment, prediction, or estimate indicating a probability that the patient is bleeding.

Various modifications and additions can be made to the embodiments discussed without departing from the scope of the invention. For example, while the embodiments described above refer to particular features, the scope of this invention also includes embodiments having different combination of features and embodiments that do not include all of the above described features.

Compensatory Reserve Index ("CRT")

Various embodiments can assess the effectiveness of fluid intake hydration, where effectiveness can be defined as, but not limited to, leading to a better hydration state or maintain an optimal hydration state. In one aspect, optimal hydration might be defined as a fluid state that maximized some performance index/measure, perhaps indicated by the patient's compensatory reserve index ("CRT," also referred to herein and in the Related Applications as "cardiac reserve index" or "hemodynamic reserve index" ("HDRI"), all of which should be considered synonymous for purposes of this disclosure). (While the term, "patient," is used herein for convenience, that descriptor should not be considered limiting, because various embodiments can be employed both in a clinical setting and outside any clinical setting, such as by an athlete before, during, or after an athletic contest or training, a person during daily activities, a soldier on the battlefield, etc. Thus, the term, "patient," as used herein, should be interpreted broadly and should be considered to be synonymous with "person.") In other cases, the assessments might be based on raw waveform data (e.g., PPG waveform data) captured by a sensor on the patient (such as the sensors described below and the Related Applications, for example). In further cases, a combination of waveform data and calculated/estimated CRT can be used to calculate the effectiveness of hydration and/or the amount of fluid needed for effective hydration. In other aspects, such functionality can be provided by and/or integrated with systems, devices (such as a cardiac reserve monitor and/or wrist-worn sensor device, or the like), tools, techniques, methods, and software described below and in the Related Applications.

For example, one set of embodiments provides methods. An exemplary method might comprise monitoring, with one or more sensors, physiological data of a patient. The method might further comprise analyzing, with a computer system, the physiological data. Many different types of physiological data can be monitored and/or analyzed by various embodiments, including, without limitation, blood pressure waveform data, plethysmograph waveform data, photoplethysmograph ("PPG") waveform data (such as that generated by a pulse oximeter), and/or the like. In an aspect of some embodiments, analyzing the physiological data might comprise analyzing the data against a pre-existing model. In some cases, the method can further comprise assessing the effectiveness of hydration efforts, and/or displaying (e.g., on a display device) an assessment of the effectiveness of the hydration efforts. Such an assessment can include, without limitation, an estimate of the effectiveness at a current time, a prediction of the effectiveness at some point in the future, an estimate and/or prediction of a volume of fluid necessary for effective hydration, an estimate of the probability a patient requires fluids, etc.

An apparatus, in accordance with yet another set of embodiments, might comprise a computer readable medium having encoded thereon a set of instructions executable by one or more computers to perform one or more operations. In some embodiments, the set of instructions might comprise instructions for performing some or all of the operations of methods provided by certain embodiments.

A system, in accordance with yet another set of embodiments, might comprise one or more processors and a computer readable medium in communication with the one or more processors. The computer readable medium might have encoded thereon a set of instructions executable by the computer system to perform one or more operations, such as the set of instructions described above, to name one example. In some embodiments, the system might further comprise one or more sensors and/or a therapeutic device, either or both of which might be in communication with the processor and/or might be controlled by the processor. Such sensors can include, but are not limited to, a blood pressure sensor, an intracranial pressure monitor, a central venous pressure monitoring catheter, an arterial catheter, an electroencephalograph, a cardiac monitor, a transcranial Doppler sensor, a transthoracic impedance plethysmograph, a pulse oximeter, a near infrared spectrometer, a ventilator, an accelerometer, an electrooculogram, a transcutaneous glucometer, an electrolyte sensor, and/or an electronic stethoscope.

CRI for Assessing Blood Loss

A set of embodiments provides methods, systems, and software that can be used, in many cases noninvasively, to quickly and accurately assess blood loss in a patient (e.g., before, during, and/or after fluid resuscitation). Such an assessment can include, without limitation, an estimate of the effectiveness at a current time, a prediction of the effectiveness at some point in the future, an estimate and/or prediction of a volume of fluid necessary for effective hydration, an estimate of the probability a patient requires fluids, an estimate and/or prediction of blood loss (e.g., before, during, and/or after fluid resuscitation), etc. In a particular set of embodiments, a device, which can be worn on the patient's body, can include one or more sensors that monitor a patient's physiological parameters. The device (or a computer in communication with the device) can analyze the data captured by the sensors and compare such data with a model (which can be generated in accordance with other embodiments) to assess the effectiveness of hydration, as described in further detail in the '426 Application, and/or to assess blood loss (e.g., before, during, and/or after fluid resuscitation).

Different embodiments can measure a number of different physiological parameters from the patient, and the analysis of those parameters can vary according to which parameters are measured (and which, according to the generated model, are found to be most predictive of the effectiveness of hydration, including the probability of the need for hydration and/or the volume of fluids needed, or most predictive of blood loss). In some cases, the parameters themselves (e.g., continuous waveform data captured by a photoplethysmograph) can be analyzed against the model to make assessments of hydration effectiveness or assessments of blood loss (e.g., before, during, and/or after fluid resuscitation). In other cases, physiological parameters can be derived from the captured data, and these parameters can be used Merely by way of example, as described further below and the '483 Application (already incorporated by reference), direct physiological data (captured by sensors) can be used to estimate a value of CRI, and this value of CRI can be used to assess the effectiveness of hydration and/or to assess blood loss (e.g., before, during, and/or after fluid resuscitation). In yet other cases, the derived CRI values and raw sensor data can be used together to perform such assessments.

For example, the '483 Application describes a compensatory reserve monitor (also described as a cardiac reserve monitor or hemodynamic reserve monitor) that is able to estimate the compensatory reserve of a patient. In an aspect, this monitor quickly, accurately, and/or in real-time can determine the probability of whether a patient is bleeding. In another aspect, the device can simultaneously monitor the patient's compensatory reserve by tracking the patient's CRI, to appropriately and effectively guide hydration and ongoing patient care. The same device (or a similar device) can also include advanced functionality to assess the effectiveness of hydration, based on the monitored CRI values, as explained in further detail in the '426 Application, and/or to rapidly assess blood loss (e.g., before, during, and/or after fluid resuscitation).

CRI is a hemodynamic parameter that is indicative of the individual-specific proportion of intravascular fluid reserve remaining before the onset of hemodynamic decompensation. CRI has values that range from 1 to 0, where values near 1 are associated with normovolemia (normal circulatory volume) and values near 0 are associated with the individual specific circulatory volume at which hemodynamic decompensation occurs.

The mathematical formula of CRI, at some time "t" is given by the following equation:

$$CRI(t) = 1 - \frac{BLV(t)}{BLV_{HDD}} \qquad (Eq. 1)$$

where BLV(t) is the intravascular volume loss ("BLV," also referred to as "blood loss volume" in the Related Applications) of a person at time "t," and $BLV_{HDD}$ is the intravascular volume loss of a person when they enter hemodynamic decompensation ("HDD"). Hemodynamic decompensation is generally defined as occurring when the systolic blood pressure falls below 70 mmHg. This level of intravascular volume loss is individual specific and will vary from subject to subject.

Lower body negative pressure ("LBNP") in some linear or nonlinear relationship λ with intravascular volume loss:

$$BLV = \lambda \cdot LBNP \qquad (Eq. 2)$$

can be used in order to estimate the CRI for an individual undergoing a LBNP experiment as follows:

$$CRI = 1 - \frac{BLV(t)}{BLV_{HDD}} \approx 1 - \frac{\lambda \cdot LBNP(t)}{\lambda \cdot LBNP_{HDD}} = 1 - \frac{LBNP(t)}{LBNP_{HDD}} \qquad (Eq. 3)$$

where LBNP(t) is the LBNP level that the individual is experiencing at time "t," and, $LBNP_{HDD}$ is the LNPB level that the individual will enter hemodynamic decompensation.

Using either CRI data, raw (or otherwise processed) sensor data, or both, various embodiments can assess the effectiveness of hydration. In one embodiment, the assessment of blood loss ("BL") can be expressed as a value between 0 and 1; when BL=1, blood loss is certain, when BL=0, there is no blood loss, and when BL is a value between 1 and 0, the value is indicative of probability of blood loss, perhaps due to ongoing bleeding before, during, and/or after fluid resuscitation. (Of course, other embodiments can scale the value of BL differently). In an aspect of some embodiments, a general expression for the estimate of blood loss is as follows:

$$BL = f_{BL}(CRI_t, FV_t, S_t) \qquad (Eq. 4)$$

where BL is a measure or an estimate of blood loss, $f_{BL}(CRI_t,FV_t,S_t)$ is an algorithm embodied by a model generated empirically, e.g., using the techniques described with respect to FIG. 4 below, and/or in the Related Applications, $CRI_t$ is a time history of CRI values (which can range from a single CRI value to many hours of CRI values), $FV_t$ is a time history of fluid volume being given to the patient (which can range from a single value to many hours of values), and $S_t$ is a time history of raw sensor values, such as physiological data measured by the sensors, as described elsewhere herein (which can range from one value to many hours of values).

The functional form of Eq. 4 is similar to but not limited to the form of the CRI model in the sense that time histories of ($CRI_t$, $FV_t$, $S_t$) data gathered from human subjects at various levels of BL are compared to time histories of ($CRI_t$, $FV_t$, $S_t$) for the current patient being monitored. The estimated BL for the current patient is then that which is the closest in ($CRI_t$, $FV_t$, $S_t$) space to the previously gathered data.

While Eq. 4 is the general expression for BL, various embodiments might use subsets of the parameters considered in Eq. 4. For instance, in one embodiment, a model might consider only the volume of fluid and CRI data, without accounting for raw sensor input. In that case, BL can be calculated as follows:

$$BL=f_{BL}(CRI_t,FV_t). \qquad (Eq.\ 5)$$

Similarly, some models might estimate BL based on sensor data, rather than first estimating CRI, in which case, BL can be expressed thusly:

$$BL=f_{BL}(FV_t,S_t). \qquad (Eq.\ 6)$$

The choice of parameters to use in modeling BL is discretionary, and it can depend on what parameters are shown (e.g., using the techniques of FIG. 4, below) to result in the best prediction of BL.

In another aspect, the effectiveness of hydration can be assessed by estimating or predicting the volume, V, of fluid necessary for effective hydration of the patient. This volume, V, can indicate a volume of fluid needed for full hydration if therapy has not yet begun, and/or it can indicate a volume remaining for fully effective hydration if therapy is underway. Like BL, the value of V can be estimated/predicted using the modeling techniques described herein and in the Related Applications. In a general case, V can be expressed as the following:

$$V=f_V(CRI_t,FV_t,S_t) \qquad (Eq.\ 7)$$

where V is an estimated volume of fluid needed by a patient need to prevent over or under hydration, $f_V(CRI_t,FV_t,S_t)$ is an algorithm embodied by a model generated empirically, e.g., using the techniques described with respect to FIG. 4 below, and/or in the Related Applications, $CRI_t$ is a time history of CRI values, $FV_t$ is a time history of fluid volume being given to the patient, and $S_t$ is a time history of physiological data received from the one or more sensors.

As with the estimate of BL, various embodiments can employ subsets of the parameters used in the general expression of Eq. 7. Thus, different embodiments might calculate V as follows:

$$V=f_V(CRI_t,FV_t) \qquad (Eq.\ 8)$$

or $$V=f_V(FV_t,S_t). \qquad (Eq.\ 9)$$

Yet another way of assessing effectiveness of hydration (which can even include assessing the need for hydration) is estimating the probability $P_f$ that the patient requires fluids; this probability can estimate the likelihood that the patient requires hydration if therapy has not been initiated, and/or, if hydration therapy is underway, the probability can estimate the likelihood that further hydration is necessary. The value of this probability, which can be expressed, e.g., as a percentage, as a decimal value between 0 and 1, etc. can be estimated using the following expression:

$$P_f=f_{P_f}(CRI_t,S_t) \qquad (Eq.\ 10)$$

where $P_f$ is the estimated probability that the patient requires fluid, $f_{P_f}(CRI_t,S_t)$ is a relationship derived based on empirical study, $CRI_t$ is a time history of CRI values, and $S_t$ is a time history of physiological data received from the one or more sensors. Once again, this general expression can be employed, in various embodiments, using subsets of the parameters in the general expression, such as the following:

$$P_f=f_{P_f}(CRI_t) \qquad (Eq.\ 11)$$

or $$P_f=f_{P_f}(S_t). \qquad (Eq.\ 12)$$

Figure 2A:
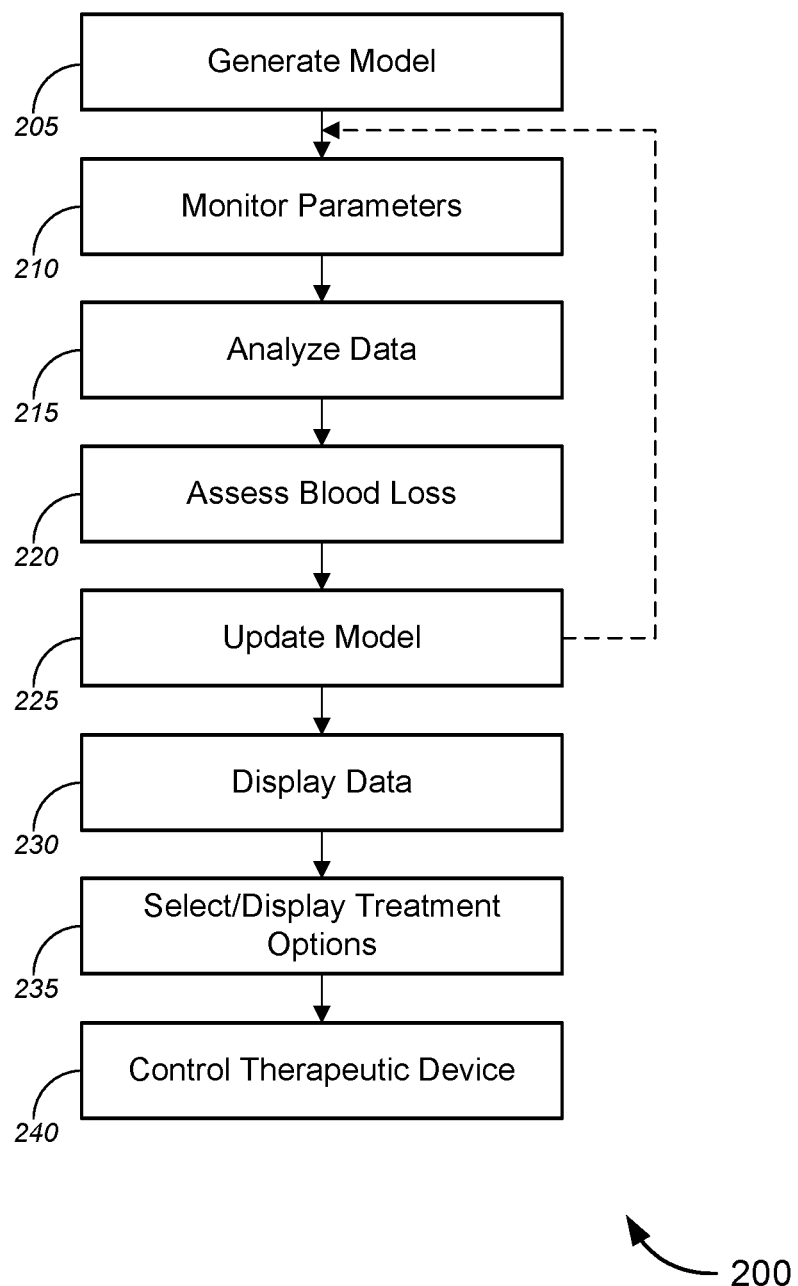
FIG. 2A is a process flow diagram illustrating a method of assessing blood loss, in accordance with various embodiments.

In the estimate of any of BL, V, or $P_f$, the function $f$ expresses a relationship that is derived based on empirical study. In a set of embodiments, for example, various sensor data can be collected from test subjects before, during, and/or after hydration efforts, during hemorrhaging, or under other conditions that might simulate such situations. This sensor data can be analyzed to develop models, using techniques similar to those of FIG. 4 below, which can then be used to estimate various assessments of hydration effectiveness, using, e.g., the methods described below with respect to FIGS. 2 and 3.

A measure of CRI, BL, V, and/or $P_f$ can be useful in a variety of clinical settings, including, but not limited to: 1) acute blood loss volume due to injury or surgery; 2) acute circulatory volume loss due to hemodialysis (also called intradialytic hypotension); and 3) acute circulatory volume loss due to various causes of dehydration (e.g., reduced fluid intake, vomiting, dehydration, etc.). A change in CRI can also herald other conditions, including, without limitation, changes in blood pressure, general fatigue, overheating, and/or certain types of illnesses. Accordingly, the tools and techniques for estimating and/or predicting CRI can have a variety of applications in a clinical setting, including, without limitation, diagnosing such conditions.

Moreover, measures of CRI, BL, V, and/or $P_f$ can have applicability outside the clinical setting. For example, an athlete can be monitored (e.g., using a wrist-wearable hydration monitor) before, during, or after competition or training to ensure optimal performance (and overall health and recovery). In other situations, a person concerned about overall wellbeing can employ a similar hydration monitor to ensure that he or she is getting enough (but not too much) fluid, ill infants or adults can be monitored while ill to ensure that symptoms (e.g., vomiting, diarrhea, etc.) do not result in dehydration, and the like. Similarly, soldiers in the field (particularly in harsh conditions) can be monitored to ensure optimal operational readiness.

In various embodiments, a hydration monitor, compensatory reserve monitor, a wrist-wearable sensor device, and/or another integrated system can include, but is not limited to, some or all of the following functionality, as described in further detail herein and in the Related Applications:

A. Estimating and/or displaying intravascular volume loss to hemodynamic decompensation (or cardiovascular collapse).

B. Estimating, predicting, and/or displaying a patient's compensatory reserve as an index that is proportional to an approximate measure of intravascular volume loss to CV collapse, recognizing that each patient has a unique reserve capacity.

C. Estimating, predicting, and/or displaying a patient's compensatory reserve as an index with a normative value at euvolemia (for example, CRI=1), representing a state in which the patient is normovolemic; a minimum value (for example, CRI=0) which implies no circulatory reserve and that the patient is experiencing CV collapse; and/or an excess value (for example, CRI>1) representing a state in which the patient is hypervolemic; the patient's normalized compensatory reserve can be displayed on a continuum between the minimum and maximum values (perhaps labeled by different symbols and/or colors depending on where the patient falls on the continuum).

D. Determining and/or displaying a probability that bleeding or intravascular volume loss has occurred.

E. Displaying an indicator that intravascular volume loss has occurred and/or is ongoing; as well as other measures of reserve, such as trend lines.

F. Estimating a patient's current blood pressure and/or predicting a patient's future blood pressure.

G. Estimating the current effectiveness of fluid resuscitation efforts.

H. Predicting the future effectiveness of fluid resuscitation efforts.

I. Estimating and/or predicting a volume of fluid necessary for effective resuscitation.

J. Estimating a probability that a patient needs fluids.

K. Estimating a hydration state of a patient or user.

L. Predicting a future hydration state of a patient or user.

M. Estimating and/or predicting a volume of fluid intake necessary for adequate hydration of a patient or user.

N. Estimating a probability that a patient is dehydrated.

In various embodiments, CRI, BL, V, and/or $P_f$ estimates can be (i) based on a fixed time history of patient monitoring (for example a 30 second or 30 heart beat window); (ii) based on a dynamic time history of patient monitoring (for example monitoring for 200 minutes, the system may use all sensor information gathered during that time to refine and improve CRI estimates, hydration effectiveness assessments, etc.); (iii) based on either establishing baseline estimates when the patient is normovolemic (no volume loss has occurred); and/or (iv) based on NO baselines estimates when patient is normovolemic.

Certain embodiments can also recommend treatment options, based on the analysis of the patient's condition (including the estimated/predicted blood pressure, probability of bleeding, state of dehydration, and/or the patient's estimated and/or predicted CRI). Treatment options can include, without limitation, such things as optimizing hemodynamics, ventilator adjustments, IV fluid adjustments (e.g., controlling the flow rate of an IV pump or the drip rate of an IV drip), transfusion of blood or blood products, infusion of volume expanders, medication changes, changes in patient position, and/or surgical therapy, or the like.

As one example, certain embodiments can be used to control an IV drip, IV pump, or rapid infuser. For instance, an embodiment might estimate the probability that a patient requires fluids and might activate such a device in response to that estimate (or instruct a clinician to attach such a device to the patient and activate the device). The system might then monitor the progress of the hydration effort (through continual or periodic assessment of the effectiveness of hydration) and increase/decrease drip or flow rates accordingly.

As another example, certain embodiments can be used as an input for a hemodialysis procedure. For example, certain embodiments can predict how much intravascular (blood) volume can be safely removed from a patient during a hemodialysis process. For example, an embodiment might provide instructions to a human operator of a hemodialysis machine, based on estimates or predictions of the patient's CRI. Additionally and/or alternatively, such embodiments can be used to continuously self-adjust the ultra-filtration rate of the hemodialysis equipment, thereby completely avoiding intradialytic hypotension and its associated morbidity.

As yet another example, certain embodiments can be used to estimate and/or predict a dehydration state (and/or the amount of dehydration) in an individual (e.g., a trauma patient, an athlete, an elder living at home, etc.) and/or to provide treatment (either by providing recommendations to treating personnel or by directly controlling appropriate therapeutic equipment). For instance, if an analytical model indicates a relationship between CRI (and/or any other physiological phenomena that can be measured and/or estimated using the techniques described herein and in the Related Applications) and dehydration state, an embodiment can apply that model, using the techniques described herein, to estimate a dehydration state of the patient.

Specific Exemplary Embodiments

Figure 14A:
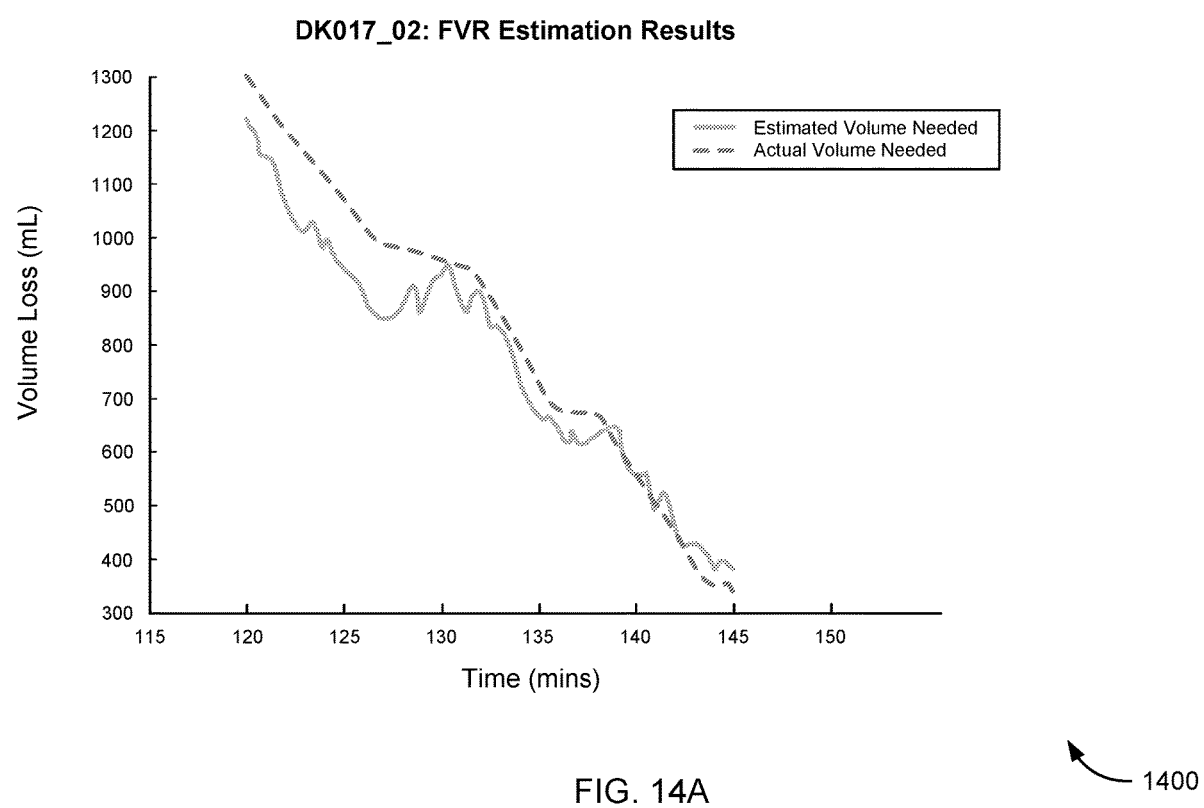
FIGS. 14A and 14B are graphical diagrams illustrating Fluid Volume Requirements ("FVR") estimation vs. actual volume requirements for two patients in a clinical trial.
Figure 14B:
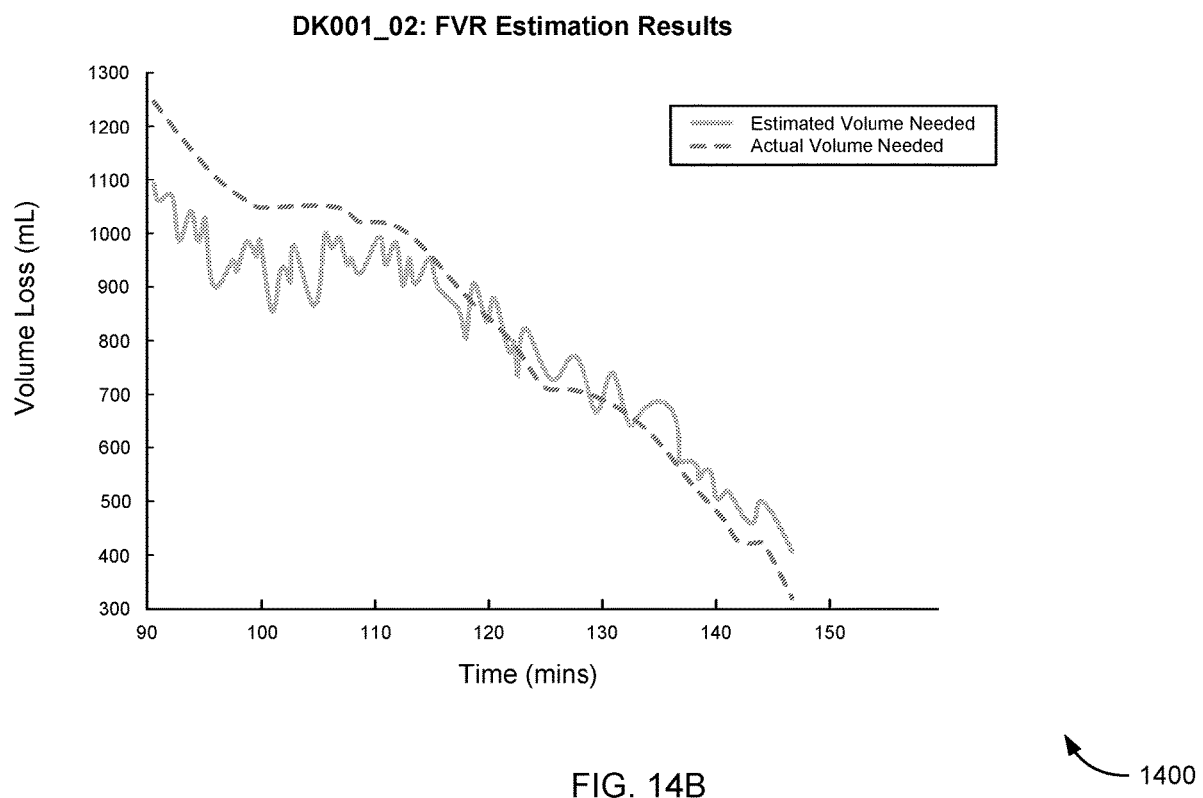
Figure 15:
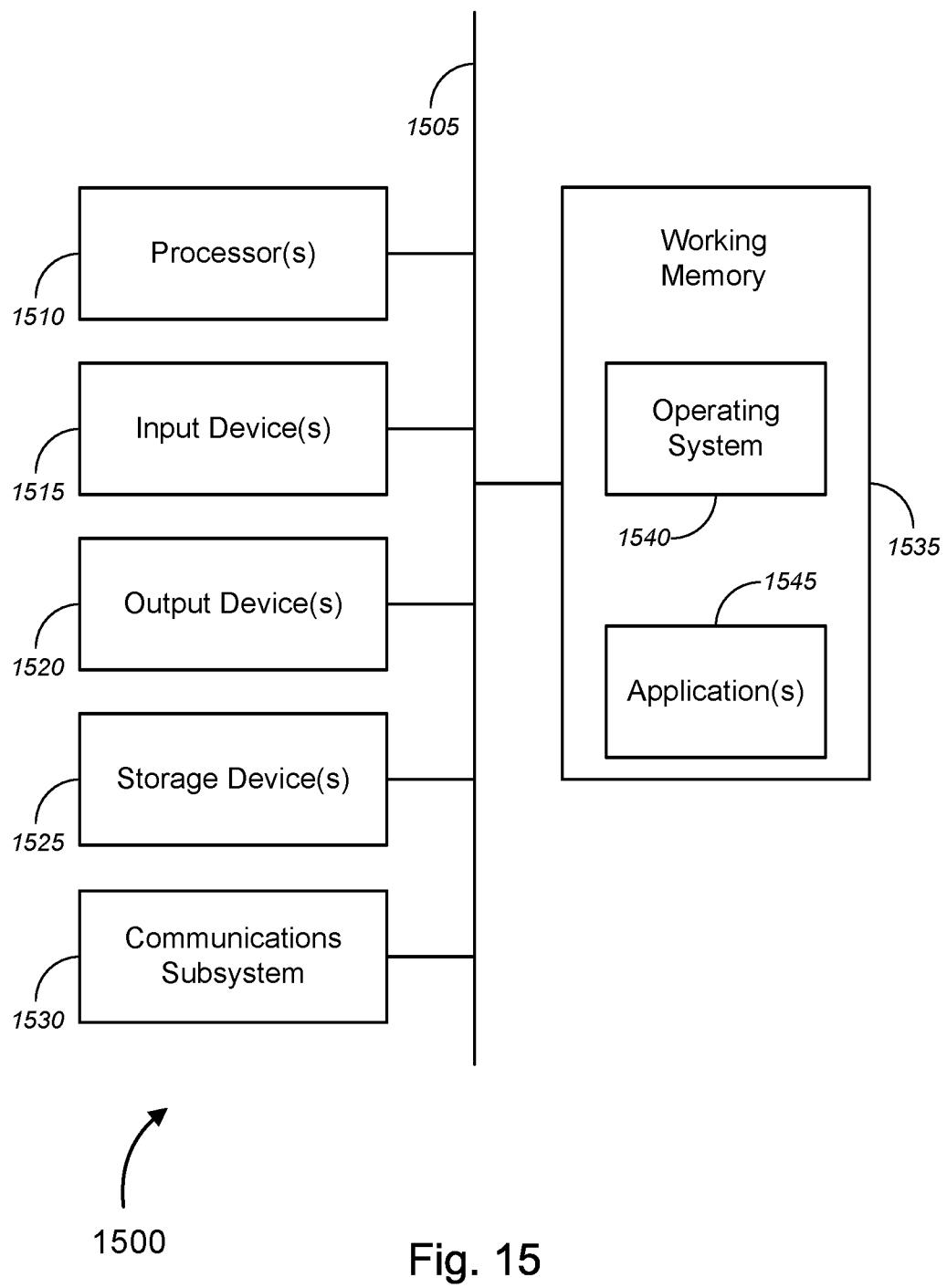
FIG. 15 is a generalized schematic diagram illustrating a computer system, in accordance with various embodiments.

We now turn to the embodiments as illustrated by the drawings. FIGS. 1-15 illustrate some of the features of the method, system, and apparatus for implementing rapid detection of bleeding of a patient following injury, in some cases, before, during, and after fluid resuscitation, as referred to above. FIGS. 1-8 illustrate some of the specific (although non-limiting) exemplary features of the method, system, and apparatus for implementing rapid detection of bleeding before, during, and after fluid resuscitation, while FIGS. 9A-9H illustrate implementing rapid detection of bleeding before, during, and after fluid resuscitation of patients in a clinical trial, and FIGS. 10-14B illustrate implementing rapid detection of bleeding of patients following injury in another clinical trial. FIG. 15 illustrates exemplary system and hardware implementation. The methods, systems, and apparatuses illustrated by FIGS. 1-15 refer to examples of different embodiments that include various components and steps, which can be considered alternatives or which can be used in conjunction with one another in the various embodiments. The description of the illustrated methods, systems, and apparatuses shown in FIGS. 1-15 is provided for purposes of illustration and should not be considered to limit the scope of the different embodiments.

With reference to the figures, FIG. 1A provides a general overview of a system 100 provided by certain embodiments. The system includes a computer system or computational device 105 in communication with one or more sensors 110 (which might include sensors 110*a*, 110*b*, and 110*c*, or the like), each of which is configured to obtain physiological data from the subject (e.g., animal or human test subject or patient) 120. In one embodiment, the computer system 105 comprises a Lenovo THINKPAD X200, 4 GB of RAM with Microsoft WINDOWS 7 operating system and is programmed with software to execute the computational methods outlined herein. The computational methods can be implemented in MATLAB 2009b and C++ programming languages. A more general example of a computer system 105 that can be used in some embodiments is described in further detail below. Even more generally, however, the computer system 105 can be any system of one or more computers that are capable of performing the techniques described herein. In a particular embodiment, for example, the computer system 105 is capable of reading values from the physiological sensors 110; generating models of physiological state from those sensors; employing such models to make individual-specific estimations, predictions, or other diagnoses; displaying the results; recommending and/or implementing a therapeutic treatment as a result of the analysis; and/or archiving (learning) these results for use in future, model building and predictions; or the like.

The sensors 110 can be any of a variety of sensors (including without limitation those described herein) for obtaining physiological data from the subject. An exemplary sensor suite might include a Finometer sensor for obtaining a noninvasive continuous blood pressure waveform, a pulse oximeter sensor, an Analog to Digital Board (National Instruments USB-9215A 16-Bit, 4 channel) for connecting the sensors (either the pulse oximeter and/or the finometer) to the computer system 105. More generally, in an embodiment, one or more sensors 110 might obtain, e.g., using one or more of the techniques described herein, continuous physiological waveform data, such as continuous blood pressure. Input from the sensors 110 can constitute continuous data signals and/or outcomes that can be used to generate, and/or can be applied to, a predictive model as described below.

In some cases, the structure or system might include a therapeutic device 115 (also referred to herein as a "physiological assistive device"), which can be controlled by the computer system 105 to administer therapeutic treatment, in accordance with the recommendations developed by analysis of a patient's physiological data. In a particular embodiment, the therapeutic device might comprise hemodialysis equipment (also referred to as a hemodialysis machine), which can be controlled by the computer system 105 based on the estimated CRI of the patient, as described in further detail below. Further examples of therapeutic devices in other embodiments can include a cardiac assist device, a ventilator, an automatic implantable cardioverter defibrillator ("AICD"), pacemakers, an extracorporeal membrane oxygenation circuit, a positive airway pressure ("PAP") device (including, without limitation, a continuous positive airway pressure ("cPAP") device, or the like), an anesthesia machine, an integrated critical care system, a medical robot, intravenous and/or intra-arterial pumps that can provide fluids and/or therapeutic compounds (e.g., through intravenous injection), intravenous drips, a rapid infuser, a heating/cooling blanket, and/or the like.

Figure 1B:
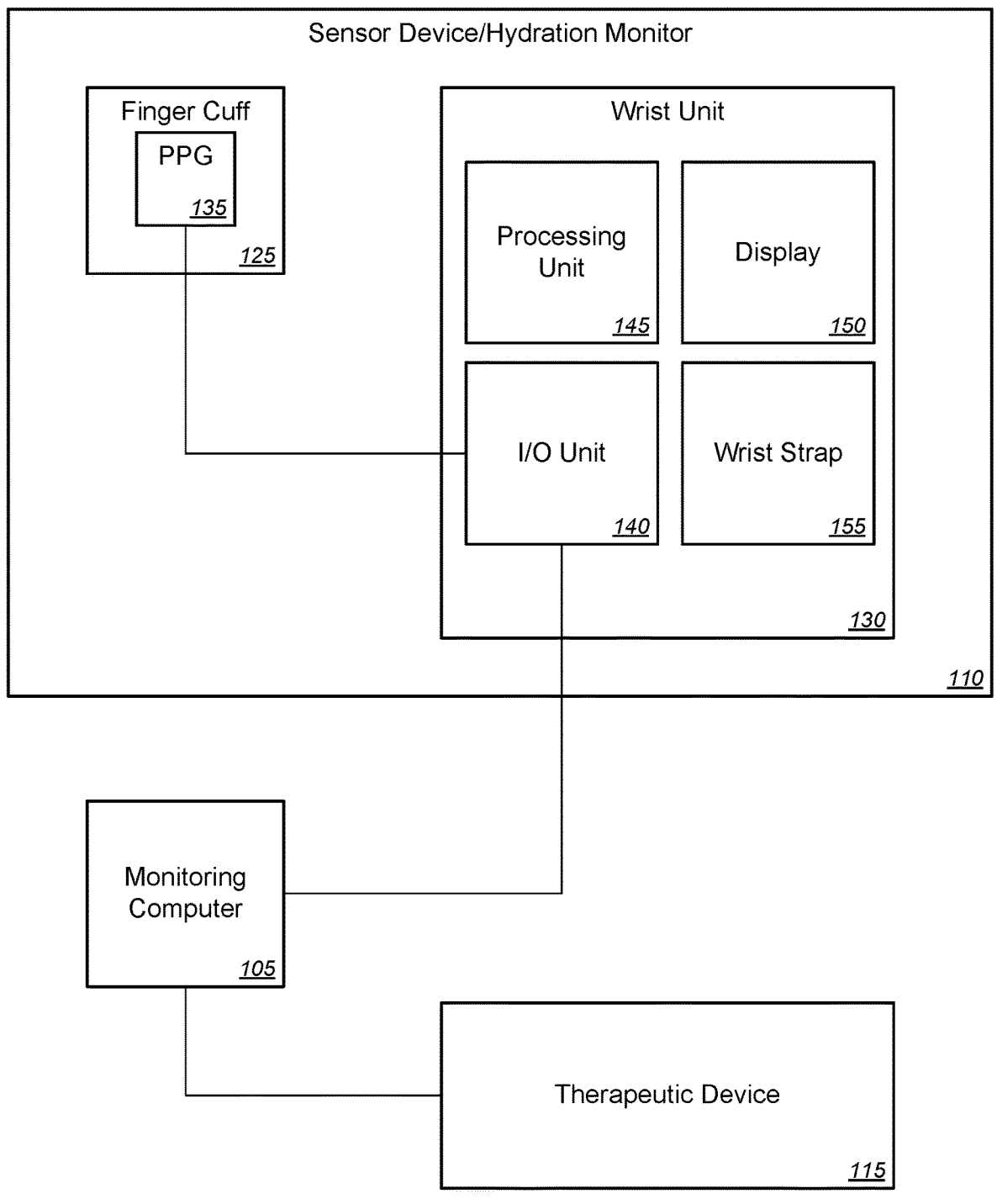
FIG. 1B is a schematic diagram illustrating a sensor system that can be worn on a patient's body, in accordance with various embodiments.

FIG. 1B illustrates in more detail an exemplary sensor device 110, which can be used in the system 100 described above. (It should be noted, of course, that the depicted sensor device 110 of FIG. 1B is not intended to be limiting, and different embodiments can employ any sensor that captures suitable data, including, without limitation, sensors described elsewhere in this disclosure and in the Related Applications.) The illustrated sensor device 110 is designed to be worn on a patient's wrist and therefore can be used both in clinical settings and in the field (e.g., on any person for whom monitoring might be beneficial, for a variety of reasons, including, without limitation, assessment of blood pressure and/or hydration during athletic competition or training, daily activities, military training or action, etc.). In one aspect, the sensor device 110 can serve as an integrated hydration monitor, which can assess hydration as described herein, display an indication of the assessment, recommend therapeutic action based on the assessment, or the like, in a form factor that can be worn during athletic events and/or daily activities.

Hence, the exemplary sensor 110 device (e.g., hydration monitor or the like) includes a finger cuff 125 and a wrist unit 130. The finger cuff 125 includes a fingertip sensor 135 (in this case, a PPG sensor) that captures data based on physiological conditions of the patient, such as PPG waveform data. The sensor 135 communicates with an input/output unit 140 of the wrist unit 130 to provide output from the sensor 135 to a processing unit 145 of the wrist unit 130. Such communication can be wired (e.g., via a standard—such as USB—or proprietary connector on the wrist unit 130) and/or wireless (e.g., via Bluetooth, such as Bluetooth Low Energy ("BTLE"), near field connection ("NFC"), WiFi, or any other suitable radio technology).

In different embodiments, the processing unit 145 can have different types of functionality. For example, in some cases, the processing unit 145 might simply act to store and/or organize data prior to transmitting the data through the I/O unit 140 to a monitoring computer 105, which might perform data analysis, to control a therapeutic device 115, etc. In other cases, however, the processing unit 145 might act as a specialized computer (e.g., with some or all of the components described in connection with FIG. 10, below and/or some or all of the functionality ascribed to the computer 105 of FIGS. 1A and 1B), such that the processing unit 145 can perform data analysis onboard, e.g., to estimate and/or predict a patient's current and/or future blood pressure. As such, the wrist unit 130 might include a display 150, which can display any output described herein, including, without limitation, estimated and/or predicted values (e.g., of CRI, blood pressure, hydration status, etc.), data captured by the sensor (e.g., heart rate, pulse oximetry data, etc.), and/or the like.

In some cases, the wrist unit 130 might include a wrist strap 155 that allows the unit to be worn on the wrist, similar to a wrist watch. Of course, other options are available to facilitate transportation of the sensor device 110 with a patient. More generally, the sensor device 110 might not include all of the components described above, and/or various components might be combined and/or reorganized; once again, the embodiment illustrated by FIG. 1B should be considered only illustrative, and not limiting, in nature.

FIGS. 2A, 2B, 3A, 3B, 4, and 5 illustrate methods in accordance with various embodiments. While the methods of FIGS. 2A, 2B, 3A, 3B, 4, and 5 are illustrated, for ease of description, as different methods, it should be appreciated that the various techniques and procedures of these methods can be combined in any suitable fashion, and that, in some embodiments, the methods depicted by FIGS. 2A, 2B, 3A, 3B, 4, and 5 can be considered interoperable and/or as portions of a single method. Similarly, while the techniques and procedures are depicted and/or described in a certain order for purposes of illustration, it should be appreciated that certain procedures may be reordered and/or omitted within the scope of various embodiments. Moreover, while the methods illustrated by FIGS. 2A, 2B, 3A, 3B, 4, and 5 can be implemented by (and, in some cases, are described below with respect to) the system 100 of FIG. 1 (including computational device or monitoring computer 105, or other components of the system, such as the sensor 110 of FIGS. 1A and 1B), these methods may also be implemented using any suitable hardware implementation. Similarly, while the system 100 of FIG. 1 (and/or other components of such a system) can operate according to the methods illustrated by FIGS. 2A, 2B, 3A, 3B, 4, and 5 (e.g., by executing instructions embodied on a computer readable medium), the system 100 of FIG. 1 can also operate according to other modes of operation and/or perform other suitable procedures.

Merely by way of example, a method might comprise one or more procedures, any or all of which are executed by a computer system. Correspondingly, an embodiment might provide a computer system configured with instructions to perform one or more procedures in accordance with methods provided by various other embodiments. Similarly, a computer program might comprise a set of instructions that are executable by a computer system (and/or a processor therein) to perform such operations. In many cases, such software programs are encoded on physical, tangible and/or non-transitory computer readable media (such as, to name but a few examples, optical media, magnetic media, and/or the like).

By way of non-limiting example, various embodiments can comprise a method for using sensor data to assess blood loss in a patient. FIG. 2 illustrates an exemplary method 200 in accordance with various embodiments. The method 200 might comprise generating a model, e.g., with a computer system, against which patient data can be analyzed to estimate and/or predict various physiological states (block 205). In a general sense, generating the model can comprise receiving data pertaining to a plurality of more physiological parameters of a test subject to obtain a plurality of physiological data sets. Such data can include PPG waveform data to name one example, and/or any other type of sensor data including, without limitation, data captured by other sensors described herein and in the Related Applications.

Generating a model can further comprise directly measuring one or more physiological states of the test subject with a reference sensor to obtain a plurality of physiological state measurements. The one or more physiological states can include, without limitation, states of various volumes of blood loss and/or fluid resuscitation, and/or various states of hydration and/or dehydration. (In other embodiments, different states can include a state of hypervolemia, a state of euvolemia, and/or a state of cardiovascular collapse (or near-cardiovascular collapse), and/or can include states that have been simulated, e.g., through use of an LBNP apparatus). Other physiological states that can be used to generate a model are described elsewhere herein and in the Related Applications.

Generating the model can further comprise correlating the physiological state(s) with the measured physiological parameters. There are a variety of techniques for generating a model in accordance with different embodiments, using these general functions. One exemplary technique for generating a model of a generic physiological state is described below with respect to FIG. 4, below, which provides a technique using a machine-learning algorithm to optimize the correlation between measured physiological parameters (such as PPG waveform data, to name one example) and physical states (e.g., various blood volume states, including states where a known volume of blood loss has occurred and/or a known volume of fluid resuscitation has been administered, various states of hydration and/or dehydration, etc.). It should be appreciated, however, that any suitable technique or model may be employed in accordance with various embodiments.

A number of physiological states can be modeled, and a number of different conditions can be imposed on test subjects as part of the model generation. For example, physiological states that can be induced (or monitored when naturally occurring) in test subjects include, without limitation, reduced circulatory system volume, known volume of blood loss, specified amounts of fluids added to blood volume, dehydration, cardiovascular collapse or near-cardiovascular collapse, euvolemia, hypervolemia, low blood pressure, high blood pressure, normal blood pressure, and/or the like.

Merely by way of example, in one set of embodiments, a number of physiological parameters of a plurality of test subjects might be measured. In some cases, a subject might undergo varying, measured levels of blood loss (either real or simulated) or intravenous fluid addition. Using the method described below with respect to FIG. 4 (or other, similar techniques, many of which are described in the Related Applications), the system can determine which sensor information most effectively differentiates between subjects at different blood loss/addition volume levels.

Additional and/or alternative to using direct (e.g., raw) sensor data to build such models, some embodiments might construct a model based on data that is derived from sensor data. Merely by way of example, one such model might use, as input values, CRI values of test subjects in different blood loss and/or volume addition conditions. Accordingly, the process of generating a model might first comprise building a model of CRI, and then, from that model, building a model of hydration effectiveness. (In other cases, a hybrid model might consider both raw sensor data and CRI data.)

A CRI model can be generated in different ways. For example, in some cases, one or more test subjects might be subjected to LBNP. In an exemplary case, LBNP data is collected from human subjects being exposed to progressively lower levels of LBNP, until hemodynamic decompensation, at which time LBNP is released and the subject recovers. Each level of LBNP represents an additional amount of blood loss. During these tests, physiological data (including, without limitation, waveform data, such as continuous non-invasive blood pressure data) can be collected before, during, and/or after the application of the LBNP. As noted above, a relationship (as expressed by Equation 2) can be identified between LBNP and intravascular volume loss, and this relationship can be used to estimate CRI. Hence, LBNP studies form a framework (methodology) for the development of the hemodynamic parameter referred to herein as CRI and can be used to generate models of this parameter.

More generally, several different techniques that induce a physiological state of reduced volume in the circulatory system, e.g., to a point of cardiovascular collapse (hemodynamic decompensation) or to a point near cardiovascular collapse, can be used to generate such a model. LBNP can be used to induce this condition, as noted above. In some cases, such as in a study described below, dehydration can be used to induce this condition as well. Other techniques are possible as well. Similarly, data collected from a subject in a state of euvolemia, dehydration, hypervolemia, and/or other states might be used to generate a CRI model in different embodiments.

At block 210, the method 200 comprises monitoring, with one or more sensors, physiological data of a patient. As noted above, a variety of physical parameters can be monitored, invasively and/or non-invasively, depending on the nature of the anticipated physiological state of the patient. In an aspect, monitoring the one or more physical parameters might comprise receiving, e.g., from a physiological sensor, continuous waveform data, which can be sampled as necessary. Such data can include, without limitation, plethysmograph waveform data, PPG waveform data (such as that generated by a pulse oximeter), and/or the like.

The method 200 might further comprise analyzing, with a computer system (e.g., a monitoring computer 105 and/or a processing unit 135 of a sensor unit, as described above), the physiological data (block 215). In some cases, the physiological data is analyzed against a pre-existing model (which might be generated as described above and which in turn, can be updated based on the analysis, as described in further detail below and in the Related Applications).

Merely by way of example, in some cases, sensor data can be analyzed directly against a generated model to assess the effectiveness of hydration (which can include estimating current values, and/or predicting future values for any or all of BL, V, and/or $P_f$, as expressed above. For example, the sensor data can be compared to determine similarities with models that estimate and/or predict any of these values. Merely by way of example, an input waveform captured by a sensor from a patient might be compared with sample waveforms generated by models for each of these values.

Figure 2B:
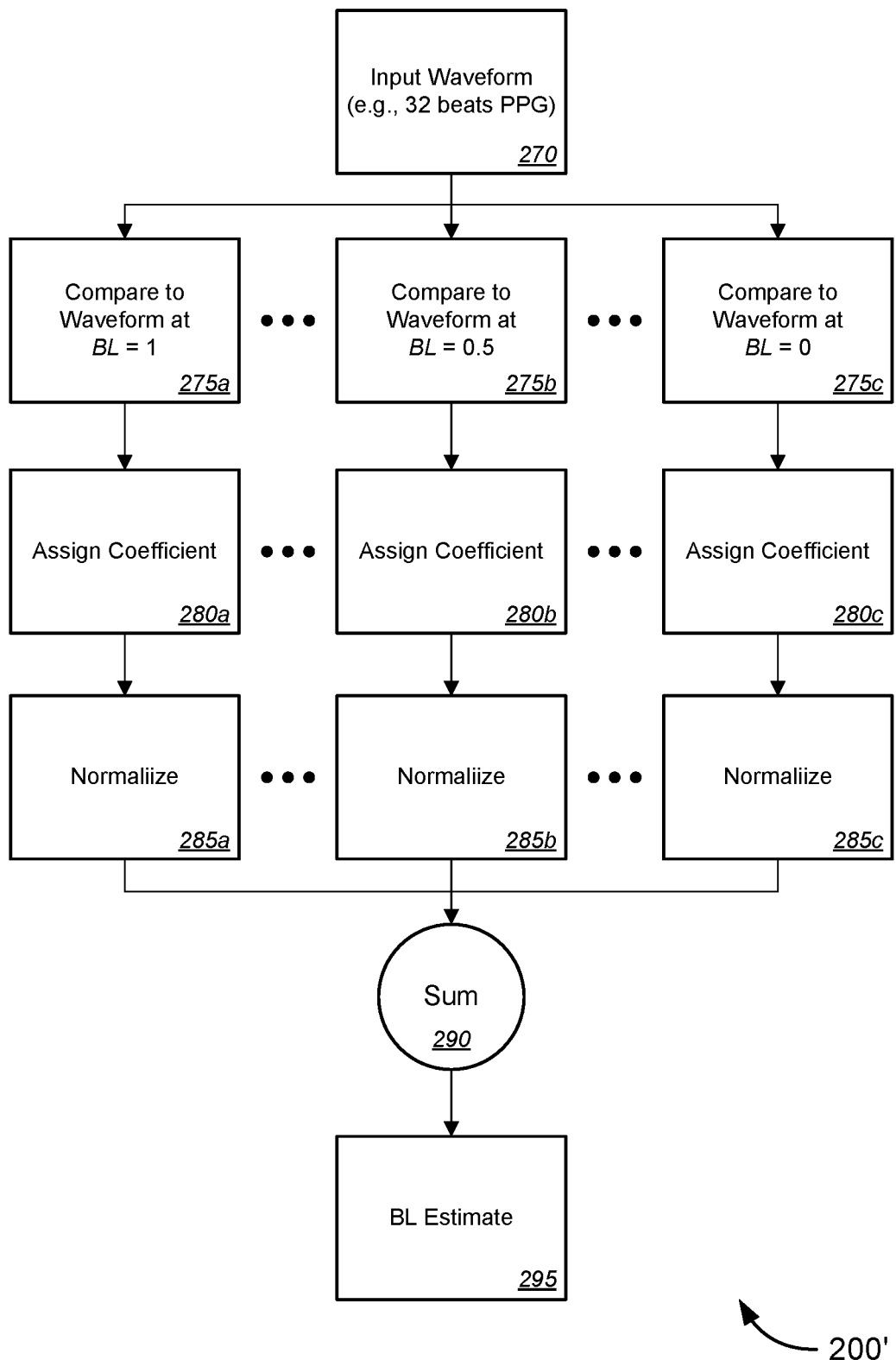
FIG. 2B illustrates a technique for assessing blood loss, in accordance with various embodiments.

For example, the technique 200' of FIG. 2B provides one method for deriving an estimate of BL in accordance with some embodiments. It should be noted that the technique 200' is presented as an example only, and that while this technique 200' estimates BL from raw sensor data, similar techniques can be used to estimate or predict BL, V, and/or $P_f$ from raw sensor data, CRI data, and/or a combination of these. For example, one model might produce a first estimate of BL from raw sensor data, produce a second estimate of BL from estimated CRI values, and then combine those estimates (in either weighted or unweighted fashion) to produce a hybrid BL estimate.

The illustrated technique 200' comprises sampling waveform data (e.g., any of the data described herein and in the Related Applications, including, without limitation, arterial waveform data, such as continuous PPG waveforms and/or continuous noninvasive blood pressure waveforms) for a specified period, such as 32 heartbeats (block 270). That sample is compared with a plurality of waveforms of reference data corresponding to BL values (block 275), which in this case range from 0 to 1 using the scale described above (but alternatively might use any appropriate scale). These reference waveforms are derived as part of the model developed using the algorithms described in this and the Related Applications, might be the result of experimental data, and/or the like. In effect, these reference waveforms reflect the relationship $f$ from Eq. 6, above.

According to the technique 200', the sample might be compared with waveforms corresponding to a BL=1 (block 275a), BL=0.5 (block 275b), and BL=0 (block 275c), as illustrated. (As illustrated by the ellipses in FIG. 2B, any number of sample waveforms can be used for the comparison; for example, if there is a nonlinear relationship between the measured sensor data and the BL values, more sample waveforms might provide for a better comparison.) From the comparison, a similarity coefficient is calculated (e.g., using a least squares or similar analysis) to express the similarity between the sampled waveform and each of the reference waveforms (block 280). These similarity coefficients can be normalized (if appropriate) (block 285), and the normalized coefficients can be summed (block 290) to produce an estimated BL value of the patient (block 295).

In other cases, similar techniques can be used to analyze data against a model based on parameters derived from direct sensor measurements. In one aspect, such operations can be iterative in nature, by generating the derived parameters—such as CRI, to name one example—by analyzing the sensor data against a first model, and then analyzing the derived parameters against a second model.

Figure 3A:
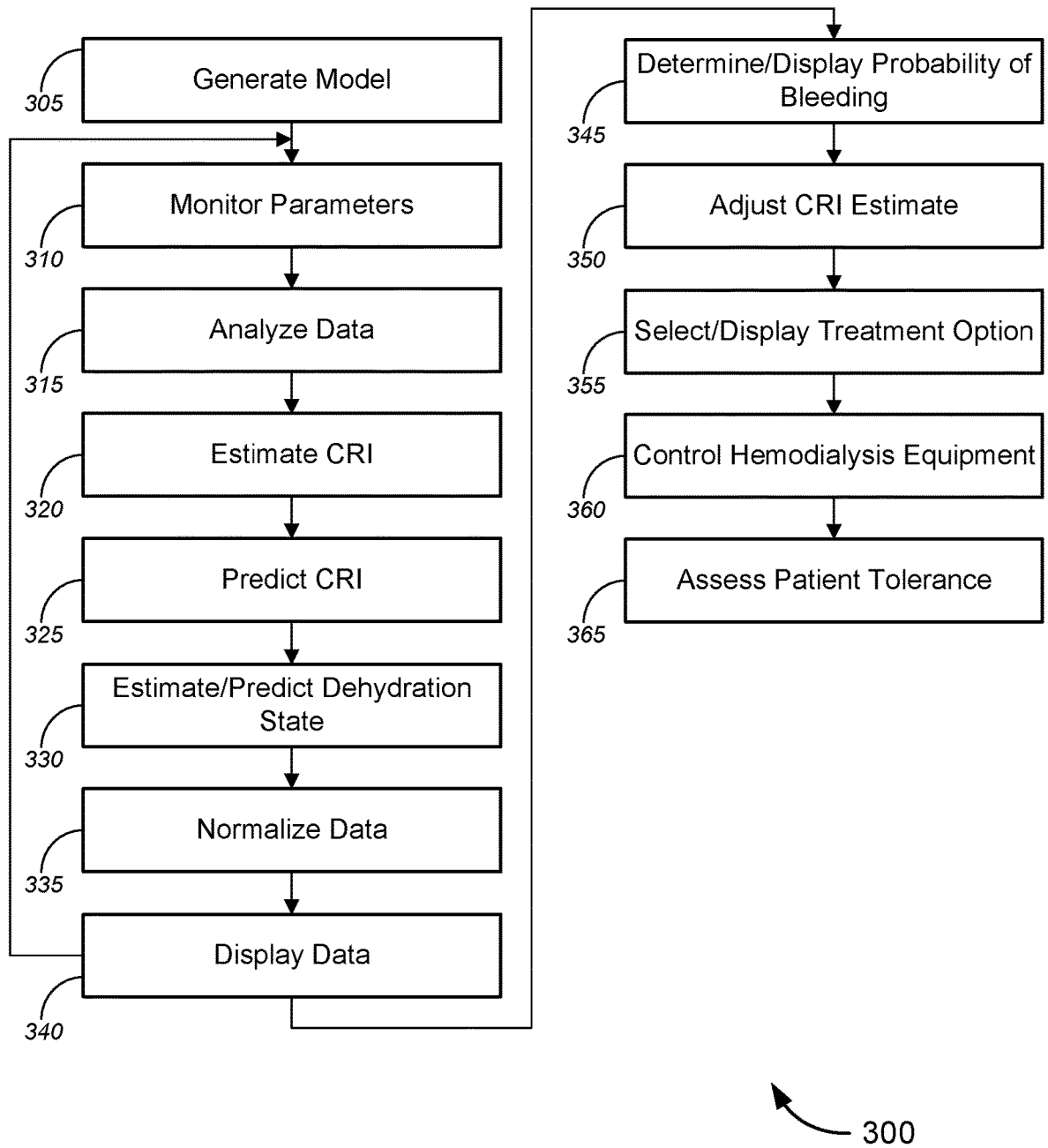
FIG. 3A is a process flow diagram illustrating a method estimating a patient's compensatory reserve and/or dehydration state, in accordance with various embodiments.

For example, FIG. 3A illustrates a method 300 of calculating a patient's CRI, which can be used (in some embodiments) as a parameter that can be analyzed to assess the effectiveness of hydration (including the probability that fluids are needed and/or the estimated volume of fluid necessary for effective hydration) and/or to assess blood loss (e.g., before, during, and/or after fluid resuscitation). The method 300 includes generating a model of CRI (block 305), monitoring physiological parameters (block 310) and analyzing the monitored physical parameters or data (block 315), using techniques such as those described above and/or in the '483 Application, for example.

Based on this analysis, the method 300, in an exemplary embodiment, includes estimating, with the computer system, a compensatory reserve (or CRI value) of the patient, based on analysis of the physiological data (block 320). In some cases, the method might further comprise predicting, with the computer system, the compensatory reserve (or CRI value) of the patient at one or more time points in the future, based on analysis of the physiological data (block 325). The operations to predict a future value of a parameter can be similar to those for estimating a current value; in the prediction context, however, the applied model might correlate measured data in a test subject with subsequent values of the diagnostic parameter, rather than contemporaneous values. It is worth noting, of course, that in some embodiments, the same model can be used to both estimate a current value and predict future values of a physiological parameter.

The estimated and/or predicted compensatory reserve of the patient can be based on several factors. Merely by way of example, in some cases, the estimated/predicted compensatory reserve can be based on a fixed time history of monitoring the physiological data of the patient and/or a dynamic time history of monitoring the physiological data of the patient. In other cases, the estimated/predicted compensatory reserve can be based on a baseline estimate of the patient's compensatory reserve established when the patient is euvolemic. In still other cases, the estimate and/or prediction might not be based on a baseline estimate of the patient's compensatory reserve established when the patient is euvolemic, but rather based on a baseline estimate of the patient's compensatory reserve established when the patient is in another physiological state or condition.

Figure 3B:
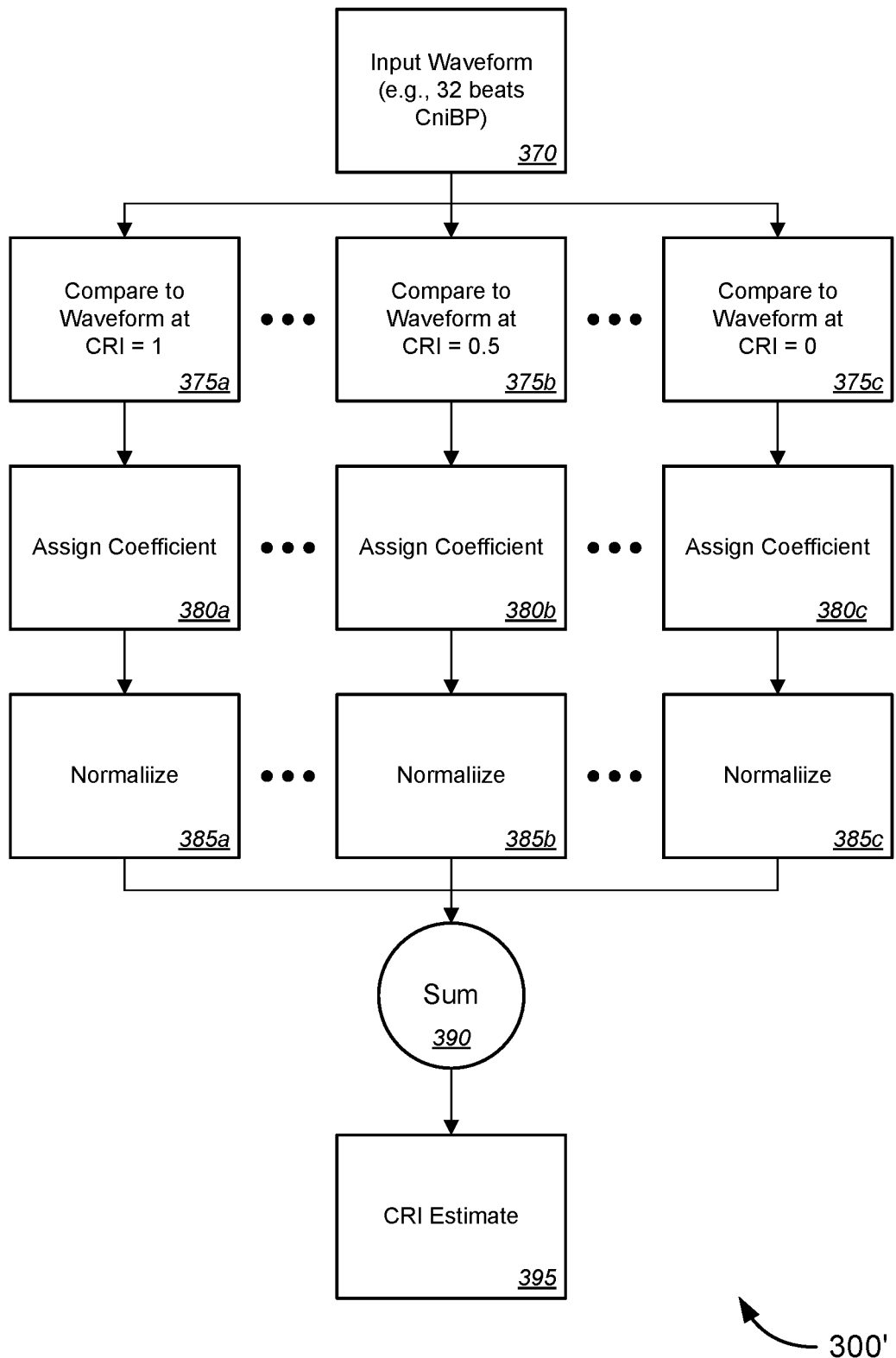
FIG. 3B illustrates a technique for estimating and/or predicting a patient's compensatory reserve index, in accordance with various embodiments.

Merely by way of example, FIG. 3B illustrates one technique 300' for deriving an estimate of CRI in accordance with some embodiments, similar to the technique 200' described above with respect to FIG. 2B for deriving an assessment of hydration effectiveness and/or deriving an assessment of blood loss (e.g., before, during, and/or after fluid resuscitation) directly from sensor data (and, in fact, CRI can be derived as described herein, and that derived value can be used, alone or with raw sensor data, to assess such effectiveness). The illustrated technique comprises sampling waveform data (e.g., any of the data described herein and in the Related Applications, including, without limitation, arterial waveform data, such as continuous PPG waveforms and/or continuous noninvasive blood pressure waveforms, or the like) for a specified period, such as 32 heartbeats (block 370). That sample is compared with a plurality of waveforms of reference data corresponding to different CRI values (block 375). (These reference waveforms, which might be derived using the algorithms described in the Related Applications, might be the result of experimental data, and/or the like). Merely by way of example, the sample might be compared with waveforms corresponding to a CRI of 1 (block 375a), a CRI of 0.5 (block 375b), and a CRI of 0 (block 375c), as illustrated. (As illustrated by the ellipses in FIG. 3B, any number of sample waveforms can be used for the comparison; for example, if there is a nonlinear relationship between the measured sensor data and the CRI estimates, more sample waveforms might provide for a better comparison.) From the comparison, a similarity coefficient is calculated (e.g., using a least squares or similar analysis) to express the similarity between the sampled waveform and each of the reference waveforms (block 380). These similarity coefficients can be normalized (if appropriate) (block 385), and the normalized coefficients can be summed (block 390) to produce an estimated value of the patient's CRI (block 395).

Returning to FIG. 3A, the method 300 can comprise estimating and/or predicting a patient's dehydration state (block 330). The patient's state of dehydration can be expressed in a number of ways. For instance, the state of dehydration might be expressed as a normalized value (for example, with 1.0 corresponding to a fully hydrated state and 0.0 corresponding to a state of morbid dehydration). In other cases, the state of dehydration might be expressed as a missing volume of fluid or as a volume of fluid present in the patient's system, or expressed using any other appropriate metric.

A number of techniques can be used to model dehydration state. Merely by way of example, as noted above (and as described in further detail below), the relationship between a patient's compensatory reserve and level of dehydration can be modeled. Accordingly, in some embodiments, estimating a dehydration state of the patient might comprise estimating the compensatory reserve (e.g., CRI) of the patient, and then, based on that estimate and the known relationship, estimating the dehydration state. Similarly, a predicted value of compensatory reserve at some point in the future can be used to derive a predicted dehydration state at that point in the future. Other techniques might use a parameter other than CRI to model dehydration state.

The method 300 might further comprise normalizing the results of the analysis (block 335), such as the compensatory reserve, dehydration state, and/or probability of bleeding, to name a few examples. Merely by way of example, the estimated/predicted compensatory reserve of the patient can be normalized relative to a normative normal blood volume value corresponding to euvolemia, a normative excess blood volume value corresponding to circulatory overload, and a normative minimum blood volume value corresponding to cardiovascular collapse. Any values can be selected as the normative values. Merely by way of example, in some embodiments, the normative excess blood volume value is >1, the normative normal blood volume value is 1, and the normative minimum blood volume value is 0. As an alternative, in other embodiments, the normative excess blood volume value might be defined as 1, the normative normal blood volume value might be defined as 0, and the normative minimum blood volume value at the point of cardiovascular collapse might be defined as −1. As can be seen from these examples, different embodiments might use a number of different scales to normalize CRI and other estimated parameters.

In an aspect, normalizing the data can provide benefits in a clinical setting, because it can allow the clinician to quickly make a qualitative judgment of the patient's condition, while interpretation of the raw estimates/predictions might require additional analysis. Merely by way of example, with regard to the estimate of the compensatory reserve of the patient, that estimate might be normalized relative to a normative normal blood volume value corresponding to euvolemia and a normative minimum blood volume value corresponding to cardiovascular collapse. Once again, any values can be selected as the normative values. For example, if the normative normal blood volume is defined as 1, and the normative minimum blood volume value is defined as 0, the normalized value, falling between 0.0 and 1.0 can quickly apprise a clinician of the patient's location on a continuum between euvolemia and cardiovascular collapse. Similar normalizing procedures can be implemented for other estimated data (such as probability of bleeding, dehydration, and/or the like).

The method 300 might further comprise displaying data with a display device (block 340). Such data might include an estimate and/or prediction of the compensatory reserve of the patient, an estimate and/or prediction of the patient's dehydration state, and/or the like. A variety of techniques can be used to display such data. Merely by way of example, in some cases, displaying the estimate of the compensatory reserve of the patient might comprise displaying the normalized estimate of the compensatory reserve of the patient. Alternatively and/or additionally, displaying the normalized estimate of the compensatory reserve of the patient might comprise displaying a graphical plot showing the normalized excess blood volume value, the normalized normal blood volume value, the normalized minimum blood volume value, and the normalized estimate of the compensatory reserve (e.g., relative to the normalized excess blood volume value, the normalized normal blood volume value, the normalized minimum blood volume value), and/or the like.

In some cases, the method 300 might comprise repeating the operations of monitoring physiological data of the patient, analyzing the physiological data, and estimating (and/or predicting) the compensatory reserve of the patient, to produce a new estimated (and/or predicted) compensatory reserve of the patient. Thus, displaying the estimate (and/or prediction) of the compensatory reserve of the patient might comprise updating a display of the estimate of the compensatory reserve to show the new estimate (and/or prediction) of the compensatory reserve, in order to display a plot of the estimated compensatory reserve over time. Hence, the patient's compensatory reserve can be repeatedly estimated and/or predicted on any desired interval (e.g., after every heartbeat, every n number of seconds, etc.), on demand, before fluid resuscitation, during fluid resuscitation, after fluid resuscitation, etc., or a combination of one or more of these.

In further embodiments, the method 300 can comprise determining a probability that the patient is bleeding, and/or displaying, with the display device, an indication of the probability that the patient is bleeding (block 345). For example, some embodiments might generate a model based on data that removes fluid from the circulatory system (such as LBNP, dehydration, etc.). Another embodiment might generate a model based on fluid removed from a subject voluntarily, e.g., during a blood donation, based on the known volume (e.g., 500 cc) of the donation. Based on this model, using techniques similar to those described above, a patient's physiological data can be monitored and analyzed to estimate a probability that the patient is bleeding (e.g., internally, or the like).

In some cases, the probability that the patient is bleeding can be used to adjust the patient's estimated CRI. Specifically, given a probability of bleeding expressed as Pr_Bleed at a time t, the adjusted value of CRI can be expressed as:

$$CRI_{Adjusted}(t)=1-((1-CRI(t))\times Pr\_Bleed(t)). \quad \text{(Eq. 13)}$$

Given this relationship, the estimated CRI can be adjusted to produce a more accurate diagnosis of the patient's condition at a given point in time (block 350).

The method 300 might comprise selecting, with the computer system, a recommended treatment option for the patient, and/or displaying, with the display device, the recommended treatment option (block 355). The recommended treatment option can be any of a number of treatment options, including, without limitation, optimization of hemodynamics of the patient, a ventilator adjustment, an intravenous fluid adjustment, transfusion of blood or blood products to the patient, infusion of volume expanders to the patient, a change in medication administered to the patient, a change in patient position, surgical therapy, and/or the like.

In a specific, non-limiting, example, the method 300 might comprise controlling operation of hemodialysis equipment (block 360), based at least in part on the estimate of the patient's compensatory reserve. Merely by way of example, a computer system that performs the monitoring and estimating functions might also be configured to adjust an ultra-filtration rate of the hemodialysis equipment in response to the estimated CRI values of the patient. In other embodiments, the computer system might provide instructions or suggestions to a human operator of the hemodialysis equipment, such as instructions to manually adjust an ultra-filtration rate, etc.

In some embodiments, the method 300 might include assessing the tolerance of an individual to blood loss, general volume loss, and/or dehydration (block 365). For example, such embodiments might include estimating a patient's CRI based on the change in a patient's position (e.g., from lying prone to standing, from standing to lying prone, from lying prone to sitting, from sitting to lying prone, from standing to sitting, and/or from sitting to standing, or the like). Based on changes to the patient's CRI in response to these maneuvers, the patient's sensitivity to blood loss, volume loss, and/or dehydration can be measured. In an aspect, this measurement can be performed using a CRI model generated as described above; the patient can be monitored using one or more of the sensors described above, and the changes in the sensor output when the subject changes position can be analyzed according to the model (as described above, for example) to assess the tolerance of the individual to volume loss. Such monitoring and/or analysis, in some embodiments, can be performed in real time.

Returning to FIG. 2, based on the analysis of the data (whether data collected directly by sensors or derived data, such as CRI, or both) against a model (which might include multiple sub-models, such as a model of BL against raw data and a model of BL against CRI, or the like), the method 200 can include assessing the blood loss of the patient (block 220), based on analysis of the patient's physiological data against the model. As noted above, assessing blood loss can include estimating or predicting a number of values, such as the estimated effectiveness, BL, of the hydration effort, the volume, V, of fluid necessary for effective hydration, the probability, $P_f$, that the patient needs fluids, and/or the like.

In some cases, the assessment of the blood loss will be based on the analysis of a plurality of measured (or derived) values of a particular physiological parameter (or plurality of parameters). Hence, in some cases, the analysis of the data might be performed on a continuous waveform, either during or after measurement of the waveform with a sensor (or both), and the assessment of the blood loss can be updated as hydration efforts and/or fluid resuscitation efforts continue. Further, the amount of fluids added to the patient's blood volume can be measured directly, and these direct measurements can be fed back into the model to update the model (at block 225) and thereby improve performance of the algorithms in the model (e.g., by refining the weights given to different parameters in terms of estimative or predictive value). The updated model can then be used to continue assessing the treatment (in the instant patient and/or in a future patient), as shown by the broken lines on FIG. 2A.

Figure 6:
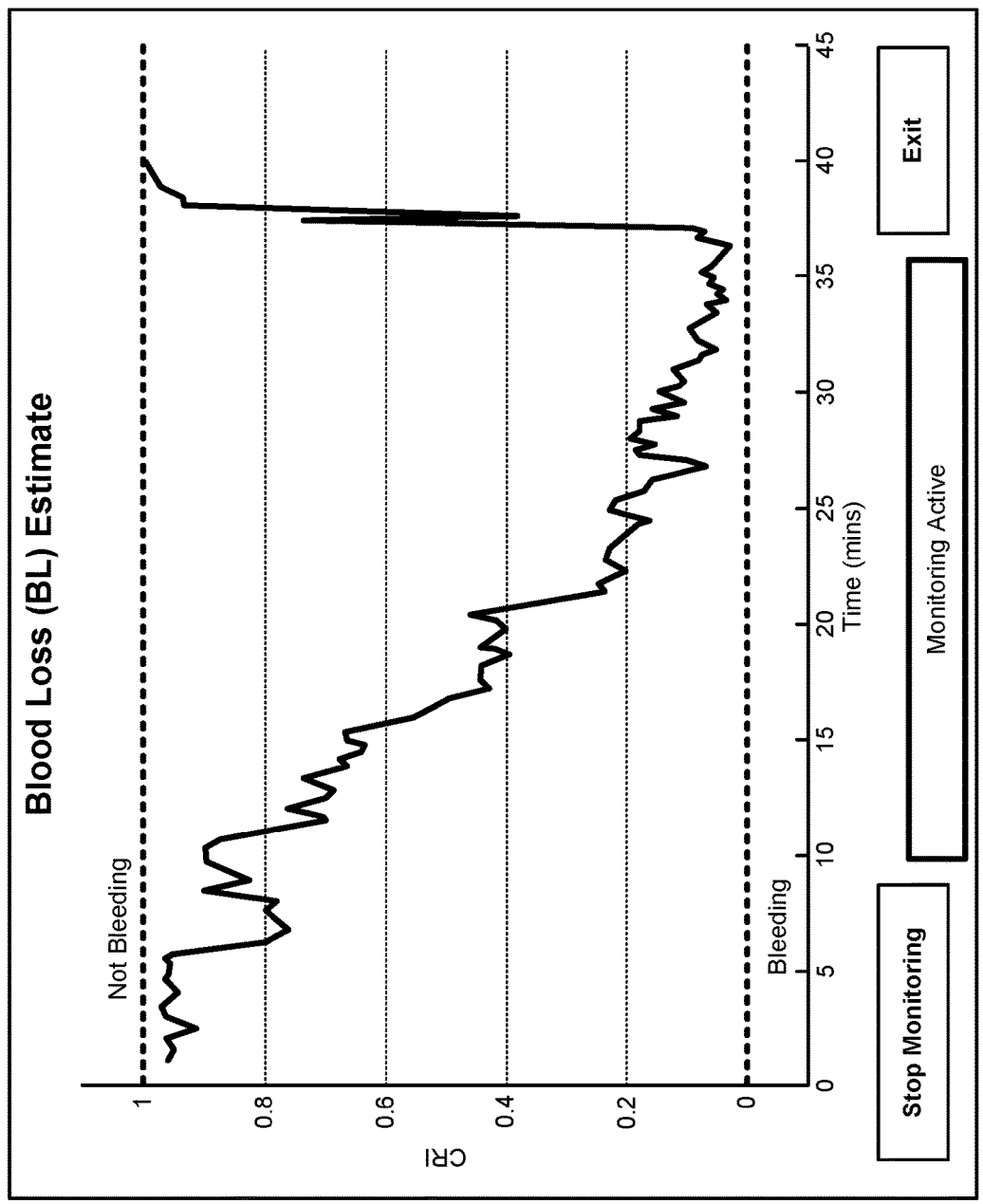
FIGS. 6-8 are exemplary screen captures illustrating display features of a compensatory reserve monitor showing assessments of blood loss before, during, and/or after fluid resuscitation, in accordance with various techniques.

In some cases, the method 200 comprises displaying data (block 230) indicating the assessment of the effectiveness of hydration. In some cases, the data might be displayed on a display of a sensor device (such as the device 110 illustrated by FIG. 1B). Alternatively and/or additionally, the data might be displayed on a dedicated machine, such as a compensatory reserve monitor, or on a monitor of a generic computer system. The data might be displayed alphanumerically, graphically, or both. FIGS. 6-8, described below, illustrate several possible exemplary displays of assessments of blood loss and/or CRI. There are many different ways that the data can be displayed, and any assessments, estimates or predictions generated by the method 200 can be displayed in any desired way, in accordance with various embodiments.

In certain embodiments, the method 200 can include selecting and/or displaying treatment options for the patient (block 235) and/or controlling a therapeutic device (block 240), based on the assessment of the blood loss of the patient. For example, a display might indicate to a clinician or the patient himself or herself that the patient is losing (or has lost) blood; that fluid resuscitation therapy should be initiated or continued; an estimated volume of fluid to drink, infuse, or otherwise consume; a drip rate for an IV drip; a flow rate for an IV pump or infuser; or the like. Similarly, the system might be configured to control operation of a therapeutic device, such as dispensing a fluid to drink from an automated dispenser, activating or adjusting the flow rate of an IV pump or infuser, adjusting the drip rate of an IV drip, and/or the like, based on the assessment of the effectiveness of hydration. As another example, certain embodiments might include a water bladder (e.g., a backpack-based hydration pack, such as those available from Camelbak Products LLC) or a water bottle, and the hydration monitor could communicate with and/or control operation of such a dispensing device (e.g., to cause the device to dispense a certain amount of fluid, to cause the device to trigger an audible alarm, etc.).

Further, in certain embodiments, the method 200 can include functionality to help a clinician (or other entity) to monitor hydration, fluid resuscitation, and/or blood volume status. For example, in some cases, any measure of effectiveness outside of the normal range (such as a value of $P_f$ higher than a certain threshold value, a value of BL lower than a threshold value, etc.) would set off various alarm conditions, such as an audible alarm, a message to a physician, a message to the patient, an update written automatically to a patient's chart, etc. Such messaging could be accomplished by electronic mail, text message, etc., and a sensor device or monitoring computer could be configured with, e.g., an SMTP client, text messaging client, or the like to perform such messaging.

In some cases, feedback and/or notifications might be sent to a third party, regardless of whether any alarm condition were triggered. For example, a hydration monitor might be configured to send monitoring results (e.g., any of the assessments, estimates and/or predictions described herein) to another device or computer, either for personal monitoring by the patient or for monitoring by another. Examples could include transmitting such alarms or data (e.g., by Bluetooth, NFC, WiFi, etc.) to a wireless phone, wearable device (e.g., smart watch or glasses) or other personal device of the patient, e.g., for inclusion in a health monitoring application. Additionally and/or alternatively, such information could be sent to a specified device or computer (e.g., via any available IP connection), for example to allow a parent to monitor a child's (or a child to monitor an elderly parent's) hydration remotely, to allow a coach to monitor a player's hydration remotely, and/or to allow a superior officer to monitor a soldier's hydration remotely, or the like. In some cases (e.g., for a coach or superior officer), an application might aggregate results from a plurality of hydration monitors, to allow the supervisor to view (e.g., in a dashboard-type configuration), hydration effectiveness and/or blood loss (and/or any other data, such as CRI, blood pressure, etc.) for a group of people. Such a display might employ, for example, a plurality of "fuel gauge" displays, one (or more) for each person in the group, allowing the supervisor to quickly ascertain any unusual results (e.g., based on the color of the gauge, etc.).

Similarly, if an alarm condition were met for another physiological parameter (such as blood pressure, which can be estimated as described in the '171 Application, for example), that alarm could trigger an assessment of hydration effectiveness via the method 200, to determine whether the first alarm condition has merit or not. If not, perhaps there could be an automated silencing of the original alarm condition, since all is well at present. More generally, the assessment techniques could be added to an ecosystem of monitoring algorithms (including, without limitation, those described in the Related Applications), which would inform one another or work in combination, to inform one another about how to maintain optimal physiological stability.

Figure 4:
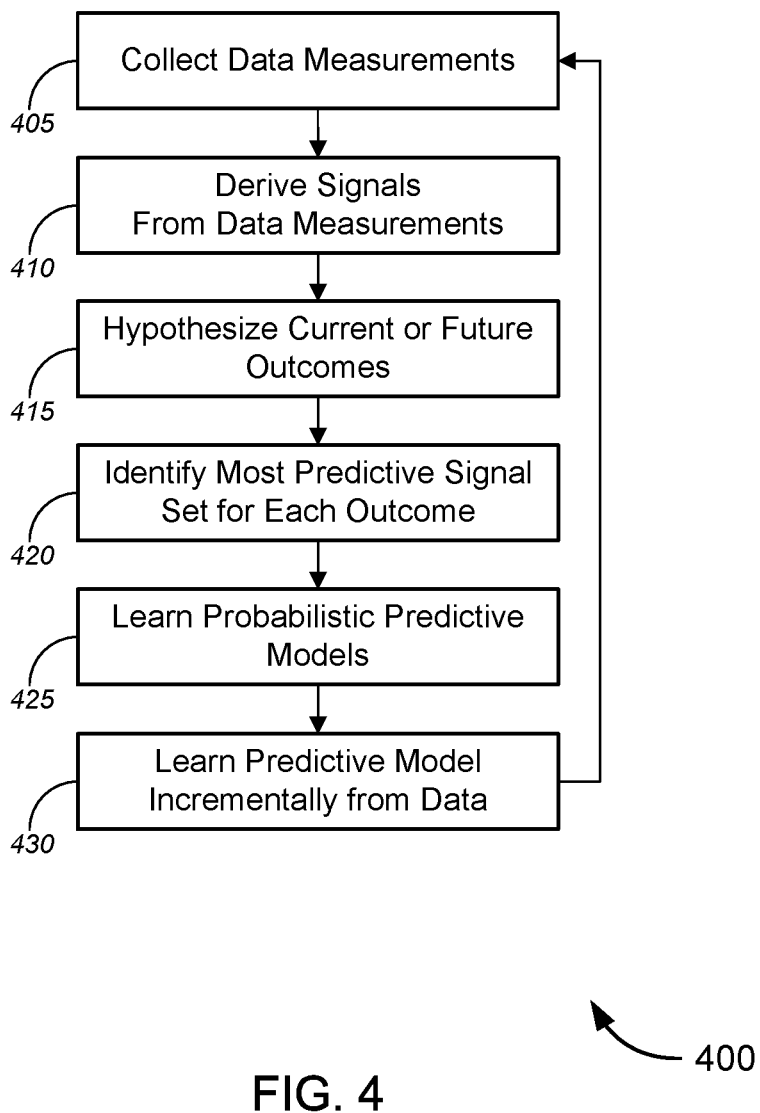
FIG. 4 is a process flow diagram illustrating a method of generating a model of a physiological state, in accordance with various embodiments.

FIG. 4 illustrates a method 400 of employing a self-learning predictive model (or machine learning) technique, according to some embodiments. In particular, the method 400 can be used to correlate physiological data received from a subject sensor with a measured physiological state. More specifically, with regard to various embodiments, the method 400 can be used to generate a model for assessing, predicting, and/or estimating various physiological parameters, such as blood loss volume, effectiveness of hydration or fluid resuscitation efforts, estimated and/or predicted blood pressure, CRI, the probability that a patient is bleeding, a patient's dehydration state, and/or the like, from one or more of a number of different physiological parameters, including, without limitation, those described above and in the Related Applications.

The method 400 begins at block 405 by collecting raw data measurements that may be used to derive a set of D data signals $s_1, \ldots, s_D$, as indicated at block 410 (each of the data signals s being, in a particular case, input from one or many different physiological sensors). Embodiments are not constrained by the type of measurements that are made at block 405 and may generally operate on any data set. For example, data signals can be retrieved from a computer memory and/or can be provided from a sensor or other input device. As a specific example, the data signals might correspond to the output of the sensors described above (which measure the types of waveform data described above, such as continuous, non-invasive PPG data and/or blood pressure waveform data, or the like).

A set of K current or future outcomes $\hat{o}=(o_1, \ldots, o_K)$ is hypothesized at block 415 (the outcomes o being, in this case, past and/or future physiological states, such as probability that fluids are needed, volume of fluid needed for effective hydration or fluid resuscitation, BL, CRI, dehydration state, probability of bleeding, etc.). The method autonomously generates a predictive model M that relates the derived data signals $\vec{s}$ with the outcomes $\vec{o}$. As used herein, "autonomous" means "without human intervention."

As indicated at block 420, this is achieved by identifying the most predictive set of signals $S_k$, where $S_k$ contains at least some (and perhaps all) of the derived signals $s_1, \ldots, s_D$ for each outcome $o_k$, where $k \in \{1, \ldots, K\}$. A probabilistic predictive model $\hat{o}_k = M_k(S_k)$ is learned at block 425, where $\hat{o}_k$ is the prediction of outcome $o_k$ derived from the model $M_k$ that uses as inputs values obtained from the set of signals $S_k$, for all $k \in \{1, \ldots, K\}$. The method 400 can learn the predictive models $\hat{o}_k = M_k(S_k)$ incrementally (block 430) from data that contains example values of signals $s_1, \ldots, s_D$ and the corresponding outcomes $o_1, \ldots, o_K$. As the data become available, the method 400 loops so that the data are added incrementally to the model for the same or different sets of signals $S_k$, for all $k \in \{1, \ldots, K\}$.

While the description above outlines the general characteristics of the methods, additional features are noted. A linear model framework may be used to identify predictive variables for each new increment of data. In a specific embodiment, given a finite set of data of signals and outcomes $\{(\vec{S}_1, \vec{o}_1), (\vec{s}_2, \vec{o}_2), \ldots\}$, a linear model may be constructed that has the form, for all $k \in \{1, \ldots, K\}$, $$\hat{o}_k = f_k(a_0 + \Sigma_{i=1}^d a_i s_i) \qquad \text{(Eq. 14)}$$

where $f_k$ is any mapping from one input to one output, and $a_0, a_1, \ldots, a_d$ are the linear model coefficients. The framework used to derive the linear model coefficients may estimate which signals $s, s_1, \ldots, s_d$ are not predictive and accordingly sets the corresponding coefficients $a_0, a_1, \ldots, a_d$ to zero. Using only the predictive variables, the model builds a predictive density model of the data, $\{(\vec{s}_1, \vec{o}_1), (\vec{s}_2, \vec{o}_2), \ldots\}$. For each new increment of data, a new predictive density model(s) can be constructed.

In some embodiments, a prediction system can be implemented that can predict future results from previously analyzed data using a predictive model and/or modify the predictive model when data does not fit the predictive model. In some embodiments, the prediction system can make predictions and/or adapt the predictive model in real-time. Moreover, in some embodiments, a prediction system can use large data sets not only to create the predictive model, but also to predict future results as well as to adapt the predictive model.

In some embodiments, a self-learning, prediction device can include a data input, a processor, and an output. Memory can include application software that when executed can direct the processor to make a prediction from input data based on a predictive model. Any type of predictive model can be used that operates on any type of data. In some embodiments, the predictive model can be implemented for a specific type of data. According to some embodiments, when data is received the predictive model can determine whether it understands the data according to the predictive model. If the data is understood, a prediction is made and the appropriate output is provided based on the predictive model. If the data is not understood when received, then the data can be added to the predictive model to modify the model. In some embodiments, the device can wait to determine the result of the specified data and can then modify the predictive model accordingly. In some embodiments, if the data is understood by the predictive model and the output that is generated using the predictive model is not accurate, then the data and the outcome can be used to modify the predictive model. According to some embodiments, modification of the predictive model can occur in real-time.

Particular embodiments can employ the tools and techniques described in the Related Applications in accordance with the methodology described herein perform the functions of a cardiac reserve monitor, a wrist-wearable sensor device, and/or a monitoring computer, as described herein (the functionality of any or all of which can be combined in a single, integrated device, in some embodiments). These functions include, but are not limited to, assessing fluid resuscitation of a patient; assessing hydration of a patient; monitoring, estimating, and/or predicting a subject's (including, without limitation, a patient's) current or future blood pressure and/or compensatory reserve; estimating and/or determining the probability that a patient is bleeding (e.g., internally) and/or has been bleeding; recommending treatment options for such conditions; and/or the like. Such tools and techniques include, in particular, the systems (e.g., computer systems, sensors, therapeutic devices, etc.) described in the Related Applications, the methods (e.g., the analytical methods for generating and/or employing analytical models, the diagnostic methods, etc.), and the software programs described herein and in the Related Applications, which are incorporated herein by reference.

Figure 5:
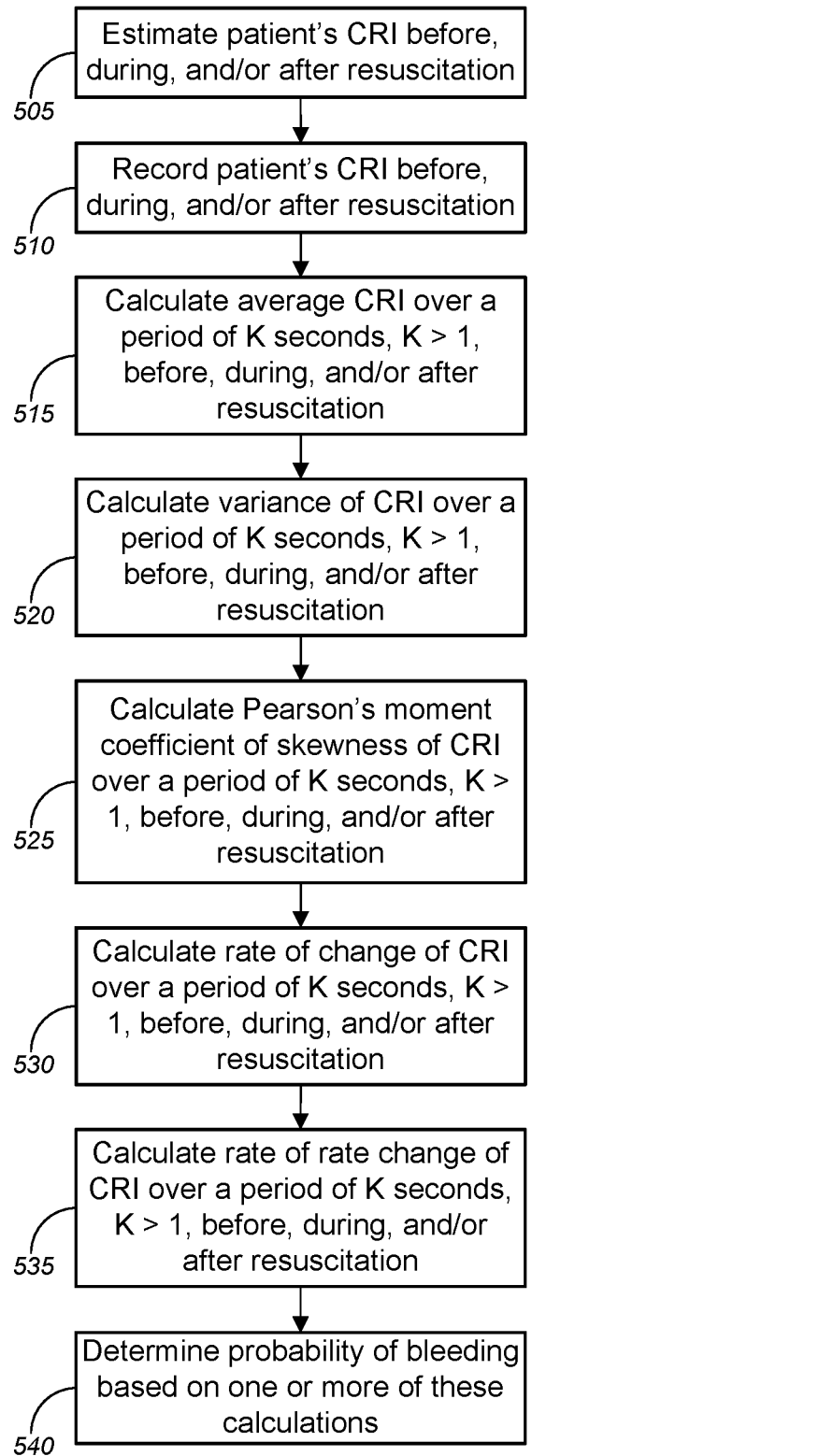
FIG. 5 is a process flow diagram illustrating a method of implementing rapid detection of bleeding before, during, and after fluid resuscitation, in accordance with various embodiments.

FIG. 5 illustrates a method 500 of implementing rapid detection of bleeding before, during, and after fluid resuscitation, in accordance with various embodiments. In the embodiment of FIG. 5, method 500, at block 505, comprises estimating a patient's CRI before, during, and/or after resuscitation (e.g., fluid resuscitation, or the like). Estimation of the patient's CRT may be performed, for example, using the techniques described above with respect to FIGS. 3A and 3B, or using other techniques described above and/or in the Related Applications.

At block 510, method 500 might comprise recording the patient's CRT, before, during, and/or after resuscitation. In some instances, the CRT may be recorded or stored on one or more of a data storage device that is part of processing unit 145 and/or a memory device that is part of the monitoring computer 105 of FIG. 1, or the like. Method 500 might further comprise calculating an average CRT over a period of K seconds (where K>1), before, during, and/or after resuscitation (block 515), calculating a standard deviation or variance of CRT over a period of K seconds (where K>1), before, during, and/or after resuscitation (block 520), calculating Pearson's moment coefficient of skewness of CRT over a period of K seconds (where K>1), before, during, and/or after resuscitation (block 525), calculating a rate of change of CRT over a period of K seconds (where K>1), before, during, and/or after resuscitation (block 530), calculating a rate of rate change (or a rate of change of rate change) of CRT (also referred to herein as "acceleration of CRT") over a period of K seconds (where K>1), before, during, and/or after resuscitation (block 535).

According to some embodiments, method 500 might further comprise, at block 540, determining probability of bleeding, based on one or more of the calculations in blocks 515-535 (which may be referred to herein as "variation results"). In other words, the variation results might be used to estimate one or more states of bleeding—namely, a (certain) non-bleeding state (perhaps designated by a symbol, "0"), a (certain) bleeding state (perhaps designated by a symbol, "1"), and some probability of bleeding state (perhaps designated by a symbol between "0" and "1").

In some embodiments, the following definitions might be used for (i) CRT value sample, (ii) a set of values of CRT, (iii) average CRT, (iv) median CRT, (v) standard deviation of CRT, (vi) rate of change of CRT, (vii) rate of change of rate change of CRT, and (viii) skewness of CRT:

(i) A specific CRT value at time t:

$$CRI(t); \tag{Eq. 15}$$

(ii) A set of CRI values at times $\{t_1, t_2, \ldots, t_K\}$:

$$CRI=\{CRI(t_1), CRI(t_2), \ldots, CRI(t_K)\}; \tag{Eq. 16}$$

(iii) Average CRI value over a specific set of times $\{t_1, t_2, \ldots, t_K\}$:

$$\overline{CRI}_K = \Sigma_{k=1}^{K} CRI(t_k); \tag{Eq. 17}$$

(iv) Median CRI value over a specific set of times $\{t_1, t_2, \ldots, t_K\}$:

$$CRI_K^{Med} = \text{Median}\{CRI(t_1), CRI(t_2), \ldots, CRI(t_K)\}; \tag{Eq. 18}$$

(v) A measure of deviation of CRI over a specific set of times $\{t_1, t_2, \ldots, t_K\}$, perhaps variance, or standard deviation defined by:

$$SD(CRI_K) = \sqrt{\frac{\sum_{k=1}^{K}(CRI(t_k) - \overline{CRI}_K)^2}{K}}; \tag{Eq. 19}$$

(vi) Rate of change of CRI, denoted by $m_K$, over a set of CRI values $\{CRI(t_1), CRI(t_2), \ldots, CRI(t_K)\}$, where the rate of change measures some increase or decrease of CRI over a specific period of time, and, for example, may be calculated as a slope of the line:

$$\begin{bmatrix} m_K \\ b \end{bmatrix} = (A^t A)^{-1} A^t \begin{bmatrix} CRI(t_1) \\ \vdots \\ CRI(t_K) \end{bmatrix}, \tag{Eq. 20}$$

where A is a matrix defined by:

$$A = \begin{bmatrix} t_1 & 1 \\ \vdots & \vdots \\ t_K & 1 \end{bmatrix}; \tag{Eq. 21}$$

(vii) Rate of change of rate change of CRI, denoted by $r_K$, over a set of CRI values $\{CRI(t_1), CRI(t_2), \ldots, CRI(t_K)\}$, where the rate of change of rate change measures some rate of change of increase or decrease of CRI over a specific period of time, and, for example, may be calculated as a second order increase or decrease of a curve:

$$\begin{bmatrix} r_K \\ m_K \\ b \end{bmatrix} = (B^t B)^{-1} B^t \begin{bmatrix} CRI(t_1) \\ \vdots \\ CRI(t_k) \end{bmatrix}, \tag{Eq. 22}$$

where B is a matrix defined by:

$$B = \begin{bmatrix} (t_1)^2 & t_1 & 1 \\ \vdots & \vdots & \vdots \\ (t_K)^2 & t_K & 1 \end{bmatrix}; \tag{Eq. 23}$$

(viii) Some measure of skewness, denoted by $S_K$ (not to be confused with set of signals, $S_k$, as described above with respect to FIG. 4), over a set of CRI values {CRI($t_1$), CRI($t_2$), ..., CRI($t_K$)}, where $S_K$ is possibly a variant of the Fisher-Pearson coefficient of skewness:

$$S_K = \frac{1}{(SD(CRI_K))^3} \left[ \frac{\sum_{k=1}^{K}(CRI(t_k) - \overline{CRI}_K)^3}{K} \right], \quad \text{(Eq. 24)}$$

and/or $S_K$ is some other measure of skewness, possibly Galton skewness (or Bowley's skewness), as defined by:

$$S_K = \frac{Q_1 + Q_3 - 2Q_2}{Q_3 - Q_1}. \quad \text{(Eq. 25)}$$

A method for estimating a (certain) non-bleeding state might include, but is not limited to, one of the following calculations or a combination of two or more such calculations, perhaps within a statistical and/or machine learning framework, or the like: (1) Average of CRI before resuscitation ("$\overline{CRI}_{BR}$")>NB1; (2) Average of CRI during resuscitation ("$\overline{CRI}_{DR}$")>NB2; (3) Average of CRI after resuscitation ("$\overline{CRI}_{AR}$")>NB3; (4) $\overline{CRI}_{AR}$–$\overline{CRI}_{DR}$>NB4; (5) $\overline{CRI}_{DR}$–$\overline{CRI}_{BR}$>NB5; (6) $\overline{CRI}_{AR}$–$\overline{CRI}_{BR}$>NB6; (7) standard deviation or variance of CRI before resuscitation ("[SD(CRI)]$_{BR}$")<NB7; (8) standard deviation or variance of CRI during resuscitation ("[SD(CRI)]$_{DR}$")<NB8; (9) standard deviation or variance of CRI after resuscitation ("[SD(CRI)]$_{AR}$")<NB9; (10) [SD(CRI)]$_{AR}$–[SD(CRI)]$_{BR}$<NB10; (11) moment coefficient of skewness of CRI (positive or negative) before resuscitation ("$S_{BR}$")<NB11; (12) moment coefficient of skewness of CRI (positive or negative) during resuscitation ("$S_{DR}$")<NB12; (13) moment coefficient of skewness of CRI (positive or negative) after resuscitation ("$S_{AR}$")<NB13; (14) rate of change of CRI before resuscitation ("$m_{BR}$")>NB14; (15) rate of change of CRI during resuscitation ("$m_{DR}$")>NB15; (16) rate of change of CRI after resuscitation ("$m_{AR}$")>NB16; (17) $m_{AR}$–$m_{BR}$>NB17; (18) $m_{DR}$–$m_{BR}$>NB18; (19) rate of rate change of CRI before resuscitation ("$r_{BR}$")>NB19; (20) rate of rate change of CRI during resuscitation ("$r_{DR}$")>NB20; (21) rate of rate change of CRI after resuscitation ("$r_{AR}$")>NB21; (22) $r_{AR}$–$r_{BR}$>NB22; (23) $r_{DR}$–$r_{BR}$>NB23; and/or the like. In some cases, each of, or one or more of, NB1 through NB23 might either be estimated experimentally or set by the user. Herein, the number K>0 may be different in each instance of the calculations (1) through (23), may be chosen by the user, or may be experimentally determined.

With reference to (1), the average CRI before resuscitation, $CRI_{BR}$={CRI($t_1$), CRI($t_2$), ..., CRI($t_K$)} may be any set of points sampled at times before resuscitation, and $\overline{CRI}_{BR}$ may be the average value of those points. Accordingly, for example, a classification of no bleeding may be made by choosing a threshold, either experimentally or user set, denoted by $^{NB}\overline{CRI}_{BR}$ (e.g., NB1 above), and classifying non-bleeding may be determined if:

$$\overline{CRI}_{BR} > {}^{NB}\overline{CRI}_{BR}. \quad \text{(Eq. 26)}$$

Referring to (2), the average CRI during resuscitation, $CRI_{DR}$={CRI($t_1$), CRI($t_2$), ..., CRI($t_K$)} may be any set of points sampled at times during resuscitation, and $\overline{CRI}_{DR}$ may be the average value of those points. Accordingly, a classification of no bleeding may be made by choosing a threshold, either experimentally or user set, denoted by $^{NB}\overline{CRI}_{DR}$ (e.g., NB2 above), and classifying non-bleeding may be determined if:

$$\overline{CRI}_{DR} > {}^{NB}\overline{CRI}_{DR}. \quad \text{(Eq. 27)}$$

Regarding (3), the average CRI after resuscitation, $CRI_{AR}$={CRI($t_1$), CRI($t_2$), ..., CRI($t_K$)} may be any set of points sampled at times after resuscitation, and $\overline{CRI}_{AR}$ may be the average value of those points. Accordingly, a classification of no bleeding may be made by choosing a threshold, either experimentally or user set, denoted by $^{NB}\overline{CRI}_{AR}$ (e.g., NB3 above), and classifying non-bleeding may be determined if:

$$\overline{CRI}_{AR} > {}^{NB}\overline{CRI}_{AR}. \quad \text{(Eq. 28)}$$

With reference to (4), $\overline{CRI}_{DR}$ and $\overline{CRI}_{AR}$ may be as defined above. Accordingly, a classification of no bleeding may be made by choosing a threshold, either experimentally or user set, denoted by $_{AR}^{NB}\overline{CRI}_{DR}$ (e.g., NB4 above), and classifying non-bleeding may be determined if:

$$\overline{CRI}_{AR} - \overline{CRI}_{DR} > {}_{AR}^{NB}\overline{CRI}_{DR}. \quad \text{(Eq. 29)}$$

Referring to (5), $\overline{CRI}_{BR}$ and $\overline{CRI}_{DR}$ may be as defined above. Accordingly, a classification of no bleeding may be made by choosing a threshold, either experimentally or user set, denoted by $_{DR}^{NB}\overline{CRI}_{BR}$ (e.g., NB5 above), and classifying non-bleeding may be determined if:

$$\overline{CRI}_{DR} - \overline{CRI}_{BR} > {}_{DR}^{NB}\overline{CRI}_{BR}. \quad \text{(Eq. 30)}$$

Regarding (6), $\overline{CRI}_{BR}$ and $\overline{CRI}_{AR}$ may be as defined above. Accordingly, a classification of no bleeding may be made by choosing a threshold, either experimentally or user set, denoted by $_{AR}^{NB}\overline{CRI}_{BR}$ (e.g., NB6 above), and classifying non-bleeding may be determined if:

$$\overline{CRI}_{AR} - \overline{CRI}_{BR} > {}_{AR}^{NB}\overline{CRI}_{BR}. \quad \text{(Eq. 31)}$$

With reference to (7), the variance of CRI before resuscitation, $CRI_{BR}$={CRI($t_1$), CRI($t_2$), ..., CRI($t_K$)} may be any set of points sampled at times before resuscitation, and [SD(CRI)]$_{DR}$ may be the variation of those values (perhaps the standard deviation as defined above). Accordingly, for example, a classification of no bleeding may be made by choosing a threshold, either experimentally or user set, denoted by $^{NB}$[SD(CRI)]$_{BR}$ (e.g., NB7 above), and classifying non-bleeding may be determined if:

$$[SD(CRI)]_{BR} < {}^{NB}[SD(CRI)]_{BR}. \quad \text{(Eq. 32)}$$

Referring to (8), the variance of CRI during resuscitation, $CRI_{DR}$={CRI($t_1$), CRI($t_2$), ..., CRI($t_K$)} may be any set of points sampled at times during resuscitation, and [SD(CRI)]$_{DR}$ may be the variation of those values (perhaps the standard deviation as defined above). Accordingly, a classification of no bleeding may be made by choosing a threshold, either experimentally or user set, denoted by $^{NB}$[SD(CRI)]$_{DR}$ (e.g., NB8 above), and classifying non-bleeding may be determined if:

$$[SD(CRI)]_{DR} < {}^{NB}[SD(CRI)]_{DR}. \quad \text{(Eq. 33)}$$

Regarding (9), the variance of CRI after resuscitation, $CRI_{AR}$={CRI($t_1$), CRI($t_2$), ..., CRI($t_K$)} may be any set of points sampled at times after resuscitation, and [SD(CRI)]$_{AR}$ may be the variation of those values (perhaps the standard deviation as defined above). Accordingly, a classification of no bleeding may be made by choosing a threshold, either experimentally or user set, denoted by $^{NB}[SD(CRI)]_{AR}$ (e.g., NB9 above), and classifying non-bleeding may be determined if:

$$[SD(CRI)]_{AR} < ^{NB}[SD(CRI)]_{AR}. \qquad (Eq. 34)$$

Referring to (10), $[SD(CRI)]_{BR}$ and $[SD(CRI)]_{AR}$ may be as defined above. Accordingly, a classification of no bleeding may be made by choosing a threshold, either experimentally or user set, denoted by $_{AR}{}^{NB}[SD(CRI)]_{BR}$ (e.g., NB10 above), and classifying non-bleeding may be determined if:

$$[SD(CRI)]_{AR} - [SD(CRI)]_{BR} <_{AR}{}^{NB}[SD(CRI)]_{BR}. \qquad (Eq. 35)$$

With reference to (11), the skewness of CRI before resuscitation, $CRI_{BR} = \{CRI(t_1), CRI(t_2), \ldots, CRI(t_K)\}$ may be any set of points sampled at times before resuscitation, and $S_{BR}$ may be a measure of skewness of those points (perhaps as defined above). Accordingly, for example, a classification of no bleeding may be made by choosing a threshold, either experimentally or user set, denoted by $^{NB}S_{BR}$ (e.g., NB11 above), and classifying non-bleeding may be determined if:

$$|S_{BR}| < ^{NB}S_{BR}. \qquad (Eq. 36)$$

Referring to (12), the skewness of CRI during resuscitation, $CRI_{DR} = \{CRI(t_1), CRI(t_2), \ldots, CRI(t_K)\}$ may be any set of points sampled at times during resuscitation, and $S_{DR}$ may be a measure of skewness of those points (perhaps as defined above). Accordingly, a classification of no bleeding may be made by choosing a threshold, either experimentally or user set, denoted by $^{NB}S_{DR}$ (e.g., NB12 above), and classifying non-bleeding may be determined if:

$$|S_{DR}| < ^{NB}S_{DR}. \qquad (Eq. 37)$$

Regarding (13), the skewness of CRI after resuscitation, $CRI_{AR} = \{CRI(t_1), CRI(t_2), \ldots, CRI(t_K)\}$ may be any set of points sampled at times after resuscitation, and $S_{AR}$ may be a measure of skewness of those points (perhaps as defined above). Accordingly, a classification of no bleeding may be made by choosing a threshold, either experimentally or user set, denoted by $^{NB}S_{AR}$ (e.g., NB13 above), and classifying non-bleeding may be determined if:

$$|S_{AR}| < ^{NB}S_{AR}. \qquad (Eq. 38)$$

With reference to (14), the rate of change of CRI before resuscitation, $CRI_{BR} = \{CRI(t_1), CRI(t_2), \ldots, CRI(t_K)\}$ may be any set of points sampled at times before resuscitation, and $m_{BR}$ may be a measure of rate of change of those points (perhaps as defined above). Accordingly, for example, a classification of no bleeding may be made by choosing a threshold, either experimentally or user set, denoted by $^{NB}m_{BR}$ (e.g., NB14 above), and classifying non-bleeding may be determined if:

$$m_{BR} > ^{NB}m_{BR}. \qquad (Eq. 39)$$

Referring to (15), the rate of change of CRI during resuscitation, $CRI_{DR} = \{CRI(t_1), CRI(t_2), \ldots, CRI(t_K)\}$ may be any set of points sampled at times during resuscitation, and $m_{DR}$ may be a measure of rate of change of those points (perhaps as defined above). Accordingly, a classification of no bleeding may be made by choosing a threshold, either experimentally or user set, denoted by $^{NB}m_{DR}$ (e.g., NB15 above), and classifying non-bleeding may be determined if:

$$m_{DR} > ^{NB}m_{DR}. \qquad (Eq. 40)$$

Regarding (16), the rate of change of CRI after resuscitation, $CRI_{AR} = \{CRI(t_1), CRI(t_2), \ldots, CRI(t_K)\}$ may be any set of points sampled at times after resuscitation, and $m_{AR}$ may be a measure of rate of change of those points (perhaps as defined above). Accordingly, a classification of no bleeding may be made by choosing a threshold, either experimentally or user set, denoted by $^{NB}m_{AR}$ (e.g., NB16 above), and classifying non-bleeding may be determined if:

$$m_{AR} > ^{NB}m_{AR}. \qquad (Eq. 41)$$

With reference to (17), $m_{BR}$ and $m_{AR}$ may be as defined above. Accordingly, a classification of no bleeding may be made by choosing a threshold, either experimentally or user set, denoted by $_{AR}{}^{NB}m_{BR}$ (e.g., NB17 above), and classifying non-bleeding may be determined if:

$$m_{AR} - m_{BR} > _{AR}{}^{NB}m_{BR}. \qquad (Eq. 42)$$

Referring to (18), $m_{BR}$ and $m_{DR}$ may be as defined above. Accordingly, a classification of no bleeding may be made by choosing a threshold, either experimentally or user set, denoted by $_{DR}{}^{NB}m_{BR}$ (e.g., NB18 above), and classifying non-bleeding may be determined if:

$$m_{DR} - m_{BR} > _{DR}{}^{NB}m_{BR}. \qquad (Eq. 43)$$

With reference to (19), the rate of rate change of CRI before resuscitation, $CRI_{BR} = \{CRI(t_1), CRI(t_2), \ldots, CRI(t_K)\}$ may be any set of points sampled at times before resuscitation, and $r_{BR}$ may be a measure of rate of rate change of those points (perhaps as defined above). Accordingly, for example, a classification of no bleeding may be made by choosing a threshold, either experimentally or user set, denoted by $^{NB}r_{BR}$ (e.g., NB19 above), and classifying non-bleeding may be determined if:

$$r_{BR} > ^{NB}r_{BR}. \qquad (Eq. 44)$$

Referring to (20), the rate of rate change of CRI during resuscitation, $CRI_{DR} = \{CRI(t_1), CRI(t_2), \ldots, CRI(t_K)\}$ may be any set of points sampled at times during resuscitation, and $r_{DR}$ may be a measure of rate of rate change of those points (perhaps as defined above). Accordingly, a classification of no bleeding may be made by choosing a threshold, either experimentally or user set, denoted by $^{NB}r_{DR}$ (e.g., NB20 above), and classifying non-bleeding may be determined if:

$$r_{DR} > ^{NB}r_{DR}. \qquad (Eq. 45)$$

Regarding (21), the rate of rate change of CRI after resuscitation, $CRI_{AR} = \{CRI(t_1), CRI(t_2), \ldots, CRI(t_K)\}$ may be any set of points sampled at times after resuscitation, and $r_{AR}$ may be a measure of rate of rate change of those points (perhaps as defined above). Accordingly, a classification of no bleeding may be made by choosing a threshold, either experimentally or user set, denoted by $^{NB}r_{AR}$ (e.g., NB21 above), and classifying non-bleeding may be determined if:

$$r_{AR} > ^{NB}r_{AR}. \qquad (Eq. 46)$$

With reference to (22), $r_{BR}$ and $r_{AR}$ may be as defined above. Accordingly, a classification of no bleeding may be made by choosing a threshold, either experimentally or user set, denoted by $_{AR}{}^{NB}r_{BR}$ (e.g., NB22 above), and classifying non-bleeding may be determined if:

$$r_{AR} - r_{BR} > _{AR}{}^{NB}r_{BR}. \qquad (Eq. 47)$$

Referring to (23), $m_{BR}$ and $m_{DR}$ may be as defined above. Accordingly, a classification of no bleeding may be made by choosing a threshold, either experimentally or user set, denoted by $_{DR}{}^{NB}m_{BR}$ (e.g., NB23 above), and classifying non-bleeding may be determined if:

$$r_{DR} - r_{BR} > _{DR}{}^{NB}r_{BR}. \qquad (Eq. 48)$$

Similarly, in some instances, a method for estimating a (certain) bleeding state might include, but is not limited to, one of the following calculations or a combination of two or more such calculations, perhaps within a statistical and/or machine learning framework, or the like: (1) Average of CRI before resuscitation ("$\overline{CRI}_{BR}$")<BL1; (2) Average of CRI during resuscitation ("$\overline{CRI}_{DR}$")<BL2; (3) Average of CRI after resuscitation ("$\overline{CRI}_{AR}$")<BL3; (4) $\overline{CRI}_{AR}-\overline{CRI}_{DR}$<BL4; (5) $\overline{CRI}_{DR}-\overline{CRI}_{BR}$<BL5; (6) $\overline{CRI}_{AR}-\overline{CRI}_{BR}$<BL6; (7) standard deviation of CRI before resuscitation ("$[SD(CRI)]_{BR}$")>BL7; (8) standard deviation of CRI during resuscitation ("$[SD(CRI)]_{DR}$")>BL8; (9) standard deviation of CRI after resuscitation ("$[SD(CRI)]_{AR}$")>BL9; (10) $[SD(CRI)]_{AR}-[SD(CRI)]_{BR}$>BL10; (11) moment coefficient of skewness of CRI (positive or negative) before resuscitation ("$S_{BR}$")>BL11; (12) moment coefficient of skewness of CRI (positive or negative) during resuscitation ("$S_{DR}$")>BL12; (13) moment coefficient of skewness of CRI (positive or negative) after resuscitation ("$S_{AR}$")>BL13; (14) rate of change of CRI before resuscitation ("$m_{BR}$")<BL14; (15) rate of change of CRI during resuscitation ("$m_{DR}$")<BL15; (16) rate of change of CRI after resuscitation ("$m_{AR}$")<BL16; (17) $m_{AR}-m_{BR}$<BL17; (18) $m_{DR}-m_{BR}$<BL18; (19) rate of rate change of CRI before resuscitation ("$r_{BR}$")<BL19; (20) rate of rate change of CRI during resuscitation ("$r_{DR}$")<BL20; (21) rate of rate change of CRI after resuscitation ("$r_{AR}$")<BL21; (22) $r_{AR}-r_{BR}$<BL22; (23) $r_{DR}-r_{BR}$<BL23; and/or the like. In some cases, each of, or one or more of, BL1 through BL20 might either be estimated experimentally or set by the user.

With reference to (1), the average CRI before resuscitation, $CRI_{BR}=\{CRI(t_1), CRI(t_2), \ldots, CRI(t_K)\}$ may be any set of points sampled at times before resuscitation, and $\overline{CRI}_{BR}$ may be the average value of those points. Accordingly, for example, a classification of bleeding may be made by choosing a threshold, either experimentally or user set, denoted by $^B\overline{CRI}_{BR}$ (e.g., BL1 above), and classifying certain bleeding may be determined if:

$$\overline{CRI}_{BR}<^B\overline{CRI}_{BR}. \quad (Eq.\ 49)$$

Referring to (2), the average CRI during resuscitation, $CRI_{DR}=\{CRI(t_1), CRI(t_2), \ldots, CRI(t_K)\}$ may be any set of points sampled at times during resuscitation, and $\overline{CRI}_{DR}$ may be the average value of those points. Accordingly, a classification of bleeding may be made by choosing a threshold, either experimentally or user set, denoted by $^B\overline{CRI}_{DR}$ (e.g., BL2 above), and classifying certain bleeding may be determined if:

$$\overline{CRI}_{DR}<^B\overline{CRI}_{DR}. \quad (Eq.\ 50)$$

Regarding (3), the average CRI after resuscitation, $CRI_{AR}=\{CRI(t_1), CRI(t_2), \ldots, CRI(t_K)\}$ may be any set of points sampled at times after resuscitation, and $\overline{CRI}_{AR}$ may be the average value of those points. Accordingly, a classification of bleeding may be made by choosing a threshold, either experimentally or user set, denoted by $^B\overline{CRI}_{AR}$ (e.g., BL3 above), and classifying certain bleeding may be determined if:

$$\overline{CRI}_{AR}<^B\overline{CRI}_{AR}. \quad (Eq.\ 51)$$

With reference to (4), $\overline{CRI}_{DR}$ and $\overline{CRI}_{AR}$ may be as defined above. Accordingly, a classification of bleeding may be made by choosing a threshold, either experimentally or user set, denoted by $_{AR}^B\overline{CRI}_{DR}$ (e.g., BL4 above), and classifying certain bleeding may be determined if:

$$\overline{CRI}_{AR}-\overline{CRI}_{DR}<_{AR}^B\overline{CRI}_{DR}. \quad (Eq.\ 52)$$

Referring to (5), $\overline{CRI}_{BR}$ and $\overline{CRI}_{DR}$ may be as defined above. Accordingly, a classification of bleeding may be made by choosing a threshold, either experimentally or user set, denoted by $_{DR}^B\overline{CRI}_{BR}$ (e.g., BL5 above), and classifying certain bleeding may be determined if:

$$\overrightarrow{CRI}_{DR}-\overline{CRI}_{BR}<_{DR}^B\overline{CRI}_{BR}. \quad (Eq.\ 53)$$

Regarding (6), $\overline{CRI}_{BR}$ and $\overline{CRI}_{AR}$ may be as defined above. Accordingly, a classification of bleeding may be made by choosing a threshold, either experimentally or user set, denoted by $_{AR}^B\overline{CRI}_{BR}$ (e.g., BL6 above), and classifying certain bleeding may be determined if:

$$\overline{CRI}_{AR}-\overline{CRI}_{BR}<_{AR}^B\overline{CRI}_{BR}. \quad (Eq.\ 54)$$

With reference to (7), the variance of CRI before resuscitation, $CRI_{BR}=\{CRI(t_1), CRI(t_2), \ldots, CRI(t_K)\}$ may be any set of points sampled at times before resuscitation, and $[SD(CRI)]_{BR}$ may be the variation of those values (perhaps the standard deviation as defined above). Accordingly, for example, a classification of bleeding may be made by choosing a threshold, either experimentally or user set, denoted by $^B[SD(CRI)]_{BR}$ (e.g., BL7 above), and classifying certain bleeding may be determined if:

$$[SD(CRI)]_{BR}>^B[SD(CRI)]_{BR}. \quad (Eq.\ 55)$$

Referring to (8), the variance of CRI during resuscitation, $CRI_{DR}=\{CRI(t_1), CRI(t_2), \ldots, CRI(t_K)\}$ may be any set of points sampled at times during resuscitation, and $[SD(CRI)]_{DR}$ may be the variation of those values (perhaps the standard deviation as defined above). Accordingly, a classification of bleeding may be made by choosing a threshold, either experimentally or user set, denoted by $^B[SD(CRI)]_{DR}$ (e.g., BL8 above), and classifying certain bleeding may be determined if:

$$[SD(CRI)]_{DR}>^B[SD(CRI)]_{DR}. \quad (Eq.\ 56)$$

Regarding (9), the variance of CRI after resuscitation, $CRI_{AR}=\{CRI(t_1), CRI(t_2), \ldots, CRI(t_K)\}$ may be any set of points sampled at times after resuscitation, and $[SD(CRI)]_{AR}$ may be the variation of those values (perhaps the standard deviation as defined above). Accordingly, a classification of bleeding may be made by choosing a threshold, either experimentally or user set, denoted by $^B[SD(CRI)]_{AR}$ (e.g., BL9 above), and classifying certain bleeding may be determined if:

$$[SD(CRI)]_{AR}>^B[SD(CRI)]_{AR}. \quad (Eq.\ 57)$$

Referring to (10), $[SD(CRI)]_{BR}$ and $[SD(CRI)]_{AR}$ may be as defined above. Accordingly, a classification of bleeding may be made by choosing a threshold, either experimentally or user set, denoted by $_{AR}^B[SD(CRI)]_{BR}$ (e.g., BL10 above), and classifying certain bleeding may be determined if:

$$[SD(CRI)]_{AR}-[SD(CRI)]_{BR}>_{AR}^B[SD(CRI)]_{BR}. \quad (Eq.\ 58)$$

With reference to (11), the skewness of CRI before resuscitation, $CRI_{BR}=\{CRI(t_1), CRI(t_2), \ldots, CRI(t_K)\}$ may be any set of points sampled at times before resuscitation, and $S_{BR}$ may be a measure of skewness of those points (perhaps as defined above). Accordingly, for example, a classification of bleeding may be made by choosing a threshold, either experimentally or user set, denoted by $^BS_{BR}$ (e.g., BL11 above), and classifying certain bleeding may be determined if:

$$|S_{BR}|>^BS_{ER}. \quad (Eq.\ 59)$$

Referring to (12), the skewness of CRI during resuscitation, $CRI_{BR}=\{CRI(t_1), CRI(t_2), \ldots, CRI(t_K)\}$ may be any set of points sampled at times during resuscitation, and $S_{DR}$ may be a measure of skewness of those points (perhaps as defined above). Accordingly, a classification of bleeding may be made by choosing a threshold, either experimentally or user set, denoted by $^{B}S_{DR}$ (e.g., BL12 above), and classifying certain bleeding may be determined if:

$$|S_{DR}|>^{B}S_{DR}. \quad \text{(Eq. 60)}$$

Regarding (13), the skewness of CRI after resuscitation, $CRI_{AR}=\{CRI(t_1), CRI(t_2), \ldots, CRI(t_K)\}$ may be any set of points sampled at times after resuscitation, and $S_{AR}$ may be a measure of skewness of those points (perhaps as defined above). Accordingly, a classification of bleeding may be made by choosing a threshold, either experimentally or user set, denoted by $^{B}S_{AR}$ (e.g., BL13 above), and classifying certain bleeding may be determined if:

$$|S_{AR}|>^{B}S_{AR}. \quad \text{(Eq. 61)}$$

With reference to (14), the rate of change of CRI before resuscitation, $CRI_{BR}=\{CRI(t_1), CRI(t_2), \ldots, CRI(t_K)\}$ may be any set of points sampled at times before resuscitation, and $m_{BR}$ may be a measure of rate of change of those points (perhaps as defined above). Accordingly, for example, a classification of bleeding may be made by choosing a threshold, either experimentally or user set, denoted by $^{B}m_{BR}$ (e.g., BL14 above), and classifying certain bleeding may be determined if:

$$m_{BR}<^{B}m_{BR}. \quad \text{(Eq. 62)}$$

Referring to (15), the rate of change of CRI during resuscitation, $CRI_{DR}=\{CRI(t_1), CRI(t_2), \ldots, CRI(t_K)\}$ may be any set of points sampled at times during resuscitation, and $m_{DR}$ may be a measure of rate of change of those points (perhaps as defined above). Accordingly, a classification of bleeding may be made by choosing a threshold, either experimentally or user set, denoted by $^{B}m_{DR}$ (e.g., BL15 above), and classifying certain bleeding may be determined if:

$$m_{DR}<^{B}m_{DR}. \quad \text{(Eq. 63)}$$

Regarding (16), the rate of change of CRI after resuscitation, $CRI_{AR}=\{CRI(t_1), CRI(t_2), \ldots, CRI(t_K)\}$ may be any set of points sampled at times after resuscitation, and $m_{AR}$ may be a measure of rate of change of those points (perhaps as defined above). Accordingly, a classification of bleeding may be made by choosing a threshold, either experimentally or user set, denoted by $^{B}m_{AR}$ (e.g., BL16 above), and classifying certain bleeding may be determined if:

$$m_{AR}<^{B}m_{AR}. \quad \text{(Eq. 64)}$$

With reference to (17), $m_{BR}$ and $m_{AR}$ may be as defined above. Accordingly, a classification of bleeding may be made by choosing a threshold, either experimentally or user set, denoted by $_{AR}{}^{B}m_{BR}$ (e.g., BL17 above), and classifying certain bleeding may be determined if:

$$m_{AR}-m_{BR}<_{AR}{}^{B}m_{BR}. \quad \text{(Eq. 65)}$$

Referring to (18), $m_{BR}$ and $m_{DR}$ may be as defined above. Accordingly, a classification of bleeding may be made by choosing a threshold, either experimentally or user set, denoted by $_{DR}{}^{B}m_{BR}$ (e.g., BL18 above), and classifying certain bleeding may be determined if:

$$m_{DR}-m_{BR}<_{DR}{}^{B}m_{BR}. \quad \text{(Eq. 66)}$$

With reference to (19), the rate of rate change of CRI before resuscitation, $CRI_{BR}=\{CRI(t_1), CRI(t_2), \ldots, CRI(t_K)\}$ may be any set of points sampled at times before resuscitation, and $r_{BR}$ may be a measure of rate of rate change of those points (perhaps as defined above). Accordingly, for example, a classification of bleeding may be made by choosing a threshold, either experimentally or user set, denoted by $^{B}r_{BR}$ (e.g., BL19 above), and classifying certain bleeding may be determined if:

$$r_{BR}<^{B}r_{BR}. \quad \text{(Eq. 67)}$$

Referring to (20), the rate of rate change of CRI during resuscitation, $CRI_{BR}=\{CRI(t_1), CRI(t_2), \ldots, CRI(t_K)\}$ may be any set of points sampled at times during resuscitation, and $r_{DR}$ may be a measure of rate of rate change of those points (perhaps as defined above). Accordingly, a classification of bleeding may be made by choosing a threshold, either experimentally or user set, denoted by $^{B}r_{DR}$ (e.g., BL20 above), and classifying certain bleeding may be determined if:

$$r_{DR}<^{B}r_{DR}. \quad \text{(Eq. 68)}$$

Regarding (21), the rate of rate change of CRI after resuscitation, $CRI_{AR}=\{CRI(t_1), CRI(t_2), \ldots, CRI(t_K)\}$ may be any set of points sampled at times after resuscitation, and $r_{AR}$ may be a measure of rate of rate change of those points (perhaps as defined above). Accordingly, a classification of bleeding may be made by choosing a threshold, either experimentally or user set, denoted by $^{B}r_{AR}$ (e.g., BL21 above), and classifying certain bleeding may be determined if:

$$r_{AR}<^{B}r_{AR}. \quad \text{(Eq. 69)}$$

With reference to (22), $r_{BR}$ and $r_{AR}$ may be as defined above. Accordingly, a classification of bleeding may be made by choosing a threshold, either experimentally or user set, denoted by $_{AR}{}^{B}r_{BR}$ P (e.g., BL22 above), and classifying certain bleeding may be determined if:

$$r_{AR}-r_{BR}<_{AR}{}^{B}r_{BR}. \quad \text{(Eq. 70)}$$

Referring to (23), $m_{BR}$ and $m_{DR}$ may be as defined above. Accordingly, a classification of bleeding may be made by choosing a threshold, either experimentally or user set, denoted by $_{DR}{}^{B}m_{BR}$ (e.g., BL23 above), and classifying may be determined if:

$$r_{DR}-r_{BR}<_{DR}{}^{B}r_{BR}. \quad \text{(Eq. 71)}$$

Likewise, in some instances, a method for estimating a probability of bleeding (e.g., designated by a symbol or value between 0 and 1) might include, but is not limited to, one of the above calculations or a combination of two or more such calculations, perhaps within a statistical and/or machine learning framework, or the like, to estimate the probability of bleeding. In some cases, the method might include, without limitation, empirical estimations of probability density functions, cumulative distribution functions using graphical and/or nonparametric models, and/or the like. Other methods might include, but are not limited to: (i) probability of bleeding being proportional to the number of times the bleeding threshold is achieved; (ii) probability of no bleeding being proportional to the number of times the no bleeding threshold is achieved; (iii) probability of bleeding being proportional to the number of times the bleeding threshold is achieved minus the number of times the no bleeding threshold is achieved; (iv) probability of bleeding being expressed as $$Pr(\text{bleeding})=f(\overline{CRI}_{BR},\overline{CRI}_{DR},\overline{CRI}_{AR},[SD(CRI)]_{BR},[SD(CRI)]_{DR},[SD(CRI)]_{AR},S_{BR},S_{DR},S_{AR},m_{BR},m_{DR},m_{AR},r_{BR},r_{DR},r_{AR}), \quad \text{(Eq. 72)}$$

where $f$ is some empirical estimation of the probability density function and/or cumulative distribution functions using graphical and/or nonparametric models.

In some embodiments, estimated CRI values might include, but are not limited to, one or more of CRI values estimated or measured after every heartbeat, CRI values averaged over the preceding or last N seconds (where N>1), and/or the median value of CRI over the preceding or last N seconds (where N>1), or the like. According to some embodiments, the calculations described above with respect to blocks 515-535 might utilize these estimated CRI values. According to some embodiments, instead of using CRI measurements, a method might use all or some of the calculations above that replace CRI values with values corresponding to measurements related to any measure of compensatory reserve, or derivative thereof, using one or more of the sensor types described above.

FIGS. 6-8 illustrate exemplary screen captures from a display device of a compensatory reserve monitor, showing various features that can be provided by one or more embodiments. Similar screens could be shown by other monitoring devices, such as a display of a wrist-wearable sensor device, a display of a monitoring computer, and/or the like. While FIGS. 6-8 use BL or CRI as an example condition for illustrative purposes, other embodiments might also display values for the volume, V, the volume of fluid necessary for effective hydration, or the probability, $P_f$, that the patient needs fluid (including additional fluid, if hydration efforts already are underway).

FIG. 6 illustrates an exemplary display 600 of a compensatory reserve monitor implementation where a normalized CRI estimate of "0" implies that blood loss is certain, and "1" implies that there is no blood loss. Values in between "0" and "1" imply a continuum of a probability of no blood loss. Alternatively, although not shown, the normalized CRI estimates can be reversed, whereby a normalized CRI estimate of "1" implies that blood loss is certain, and "0" implies that there is no blood loss. Values in between "0" and "1" imply a continuum of a probability of blood loss.

Figure 7A:
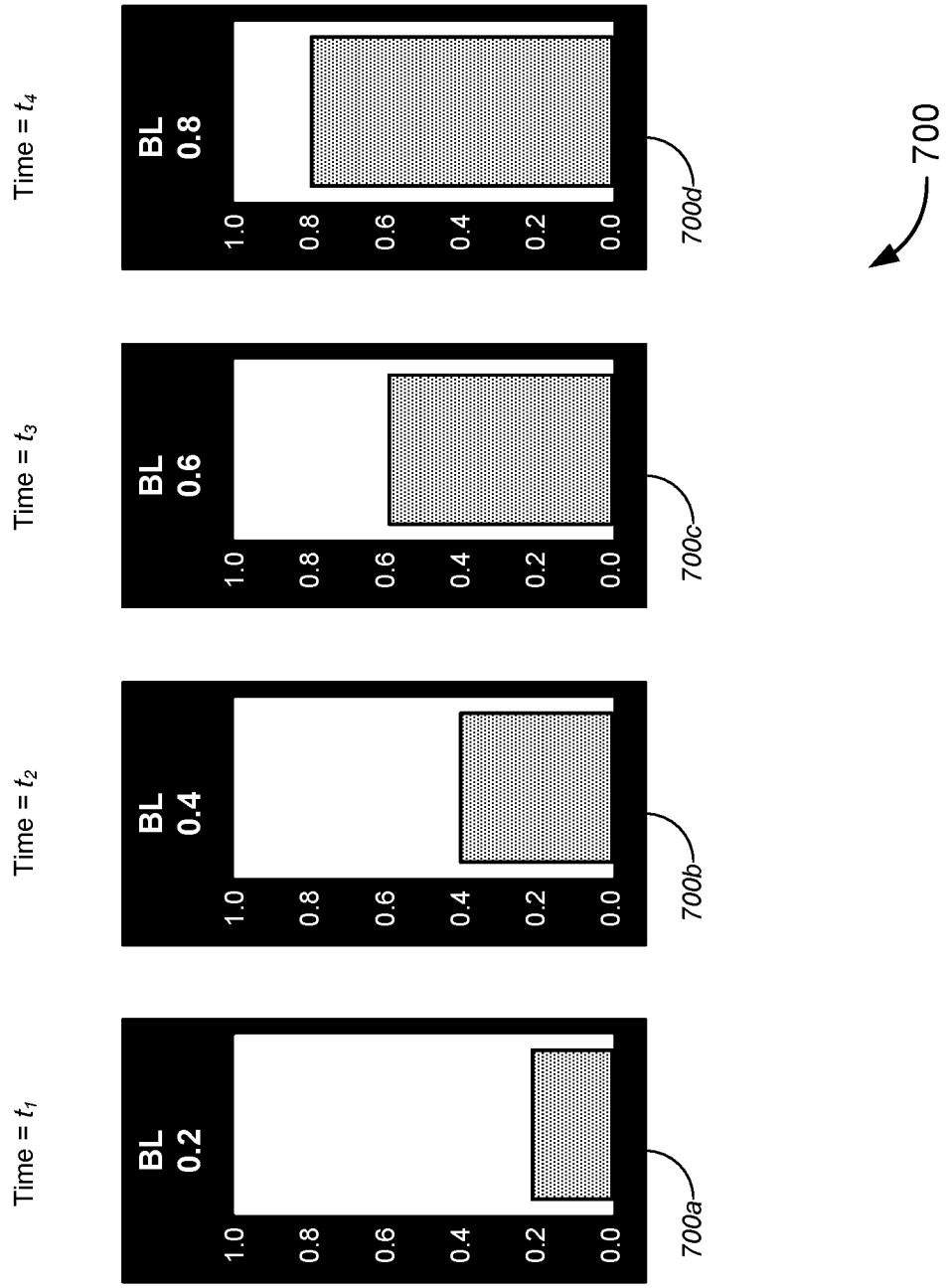
Figure 8:
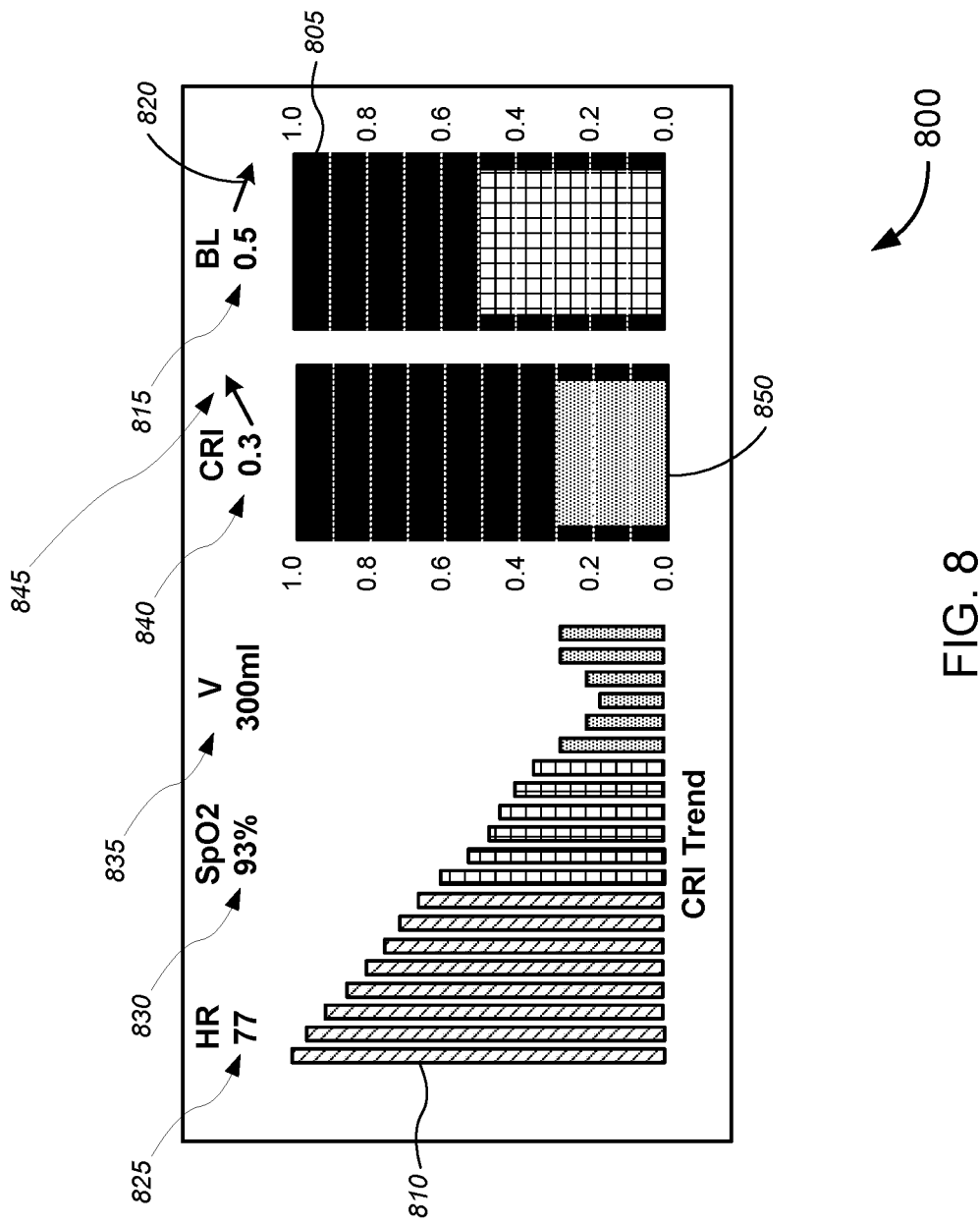

FIG. 7A illustrates four screen captures 700 of a display of a compensatory reserve monitor implementation that displays BL as a "fuel gauge" type bar graph for a person undergoing central volume blood loss and subsequent hydration efforts, or for a person who is about to, is undergoing, or has undergone fluid resuscitation. While FIG. 6 illustrates a trace of CRI over time, the bar graphs of FIG. 7A provide snapshots of BL at the time of each screen capture corresponding to the CRI of FIG. 6. (In the illustrated implementation, the bar graphs are continuously and/or periodically updated, such that each bar graph could correspond to a particular position on the X-axis of FIG. 6.) The fuel gauge can be configured to show probability of no blood loss (in which a value of "1" implies no blood loss, a value of "0" implies certain blood loss, and a value between "0" and "1" implies a continuum of a probability of no blood loss), similar to FIG. 6. Alternatively, the fuel gauge can be configured to show probability of blood loss (in which a value of "0" implies no blood loss, a value of "1" implies certain blood loss, and a value between "0" and "1" implies a continuum of a probability of blood loss).

Figure 7B:
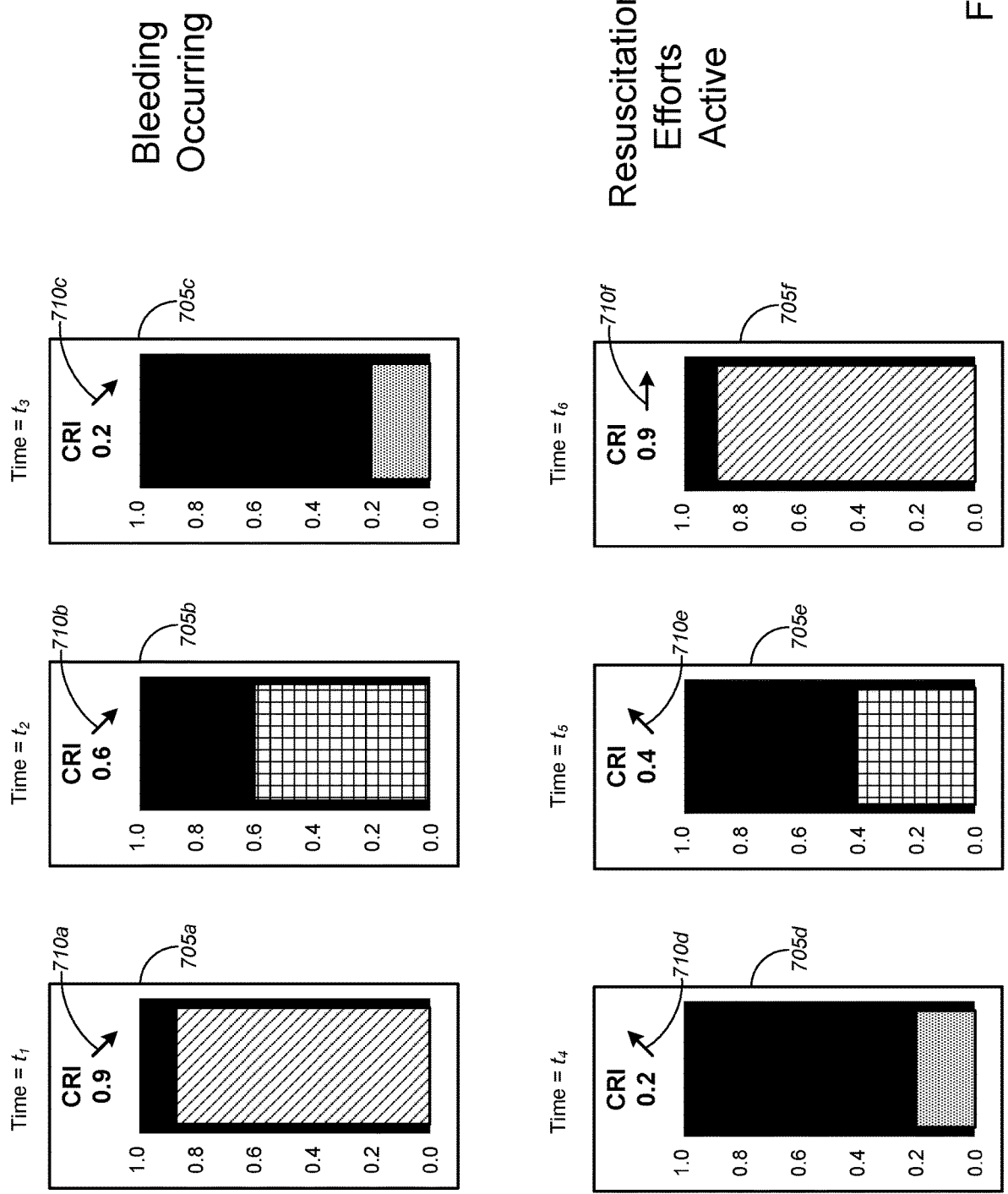

A variety of additional features are possible. Merely by way of example FIG. 7B illustrates similar "fuel gauge" type displays, but the displays feature bars of different colors— for example, green (illustrated by diagonal cross-hatching), yellow (illustrated by a checked pattern) and red (illustrated by gray shading) corresponding to different levels of CRI, along with arrows 710 indicating trending in the CRI values (e.g., rising, declining, or remaining stable), the CRI values and trends being indicative of blood loss occurring and/or resuscitation efforts being active.

In some embodiments, such a "fuel gauge" display (or other indicator of BL or CRI and/or different physiological parameters) can be incorporated in a more comprehensive user interface. Merely by way of example, FIG. 8 illustrates an exemplary display 800 of a monitoring system. The display 800 includes a graphical, color-coded "fuel gauge" type display 805 of the current estimated BL (similar to the displays illustrated by FIG. 7B), along with a historical display 810 of recent CRI estimates; in this example, each bar on the historical display 810 might correspond to an estimate performed every minute, but different estimate frequencies or time intervals are possible, and in some embodiments, the operator can be given the option to specify a different frequency or time interval. In the illustrated embodiment, the display 800 also includes numerical display 815 of the current BL as well as a trend indicator 820 (similar to that indicated above).

In particular embodiments, the display 800 can include additional information (and, in some cases, the types of information displayed and/or the type of display can be configured by the operator). For instance, the exemplary display 800 includes an indicator 825 of the patient's current heart rate and an indicator 830 of the patient's blood oxygen saturation level (SpO2). The exemplary display 800 also includes an indicator of the estimated volume, V, necessary for effective hydration, as well as an numerical indicator 840, a trend indicator 845, and a similar color coded "fuel gauge" display 850 of the current CRI. Other monitored parameters (although not shown) might be displayed as well, such as an ECG tracing, blood pressure, probability of bleeding estimates, and/or the like.

Exemplary Clinical Studies

FIGS. 9A-9H (collectively, "FIG. 9") are graphical diagrams 900 illustrating rapid detection of bleeding before, during, and after fluid resuscitation of patients in a multi-trauma clinical study at Denver Health Medical Center ("DHMC"), in accordance with various embodiments. In one exemplary multi-trauma clinical study at DHMC, 50 patients were enrolled, of which 45 patients met required criteria while 5 were excluded (as having incomplete data and/or device). Of the 45 patients, 12 were bleeding (with initial CRI values of 0.17±0.07 and mean injury severity score ("ISS") of 27±12.7), 30 non-bleeding (with initial CRI values of 0.56±0.17 and mean ISS of 7.5±8.7), and 3 indeterminate.

Figure 9A:
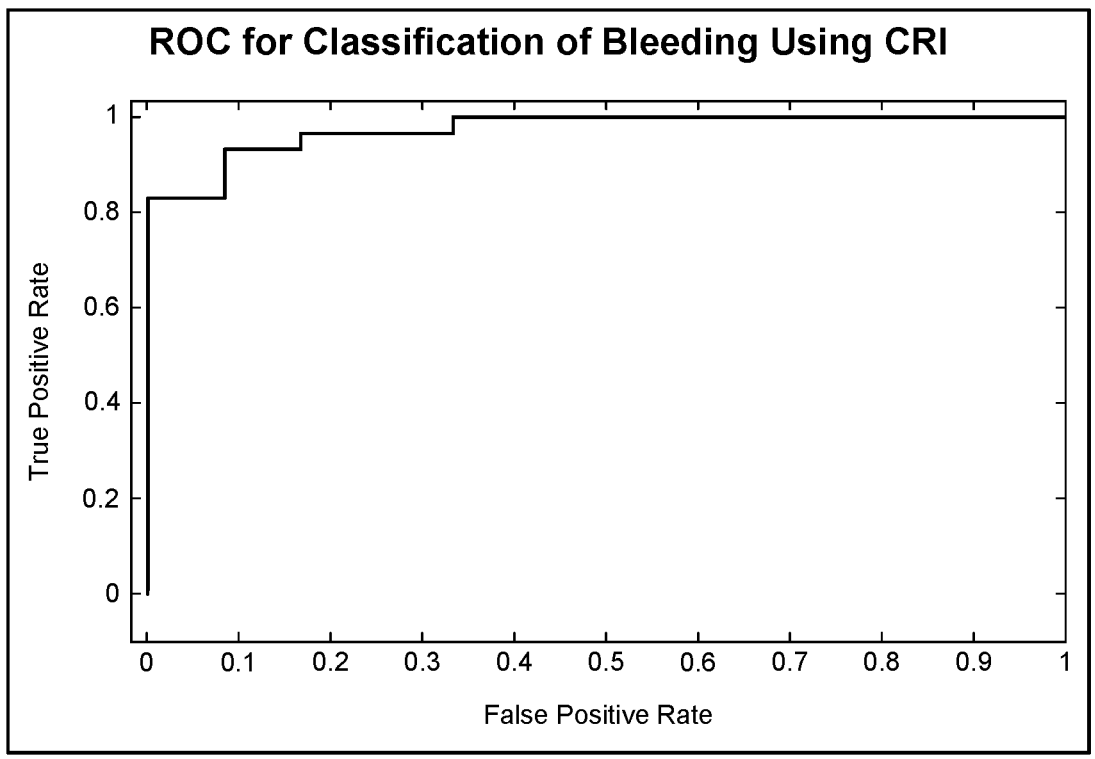
FIGS. 9A-9H are graphical diagrams illustrating rapid detection of bleeding before, during, and after fluid resuscitation of patients in a multi-trauma clinical study at Denver Health Medical Center, in accordance with various embodiments.

With reference to FIG. 9, FIG. 9A illustrates a receiver operating characteristic ("ROC") curve that is used for classification of bleeding using compensatory reserve. The sensitivity is 0.93, with specificity of 0.92, and area under the curve ("AUC") of 0.97.

Figure 9B:
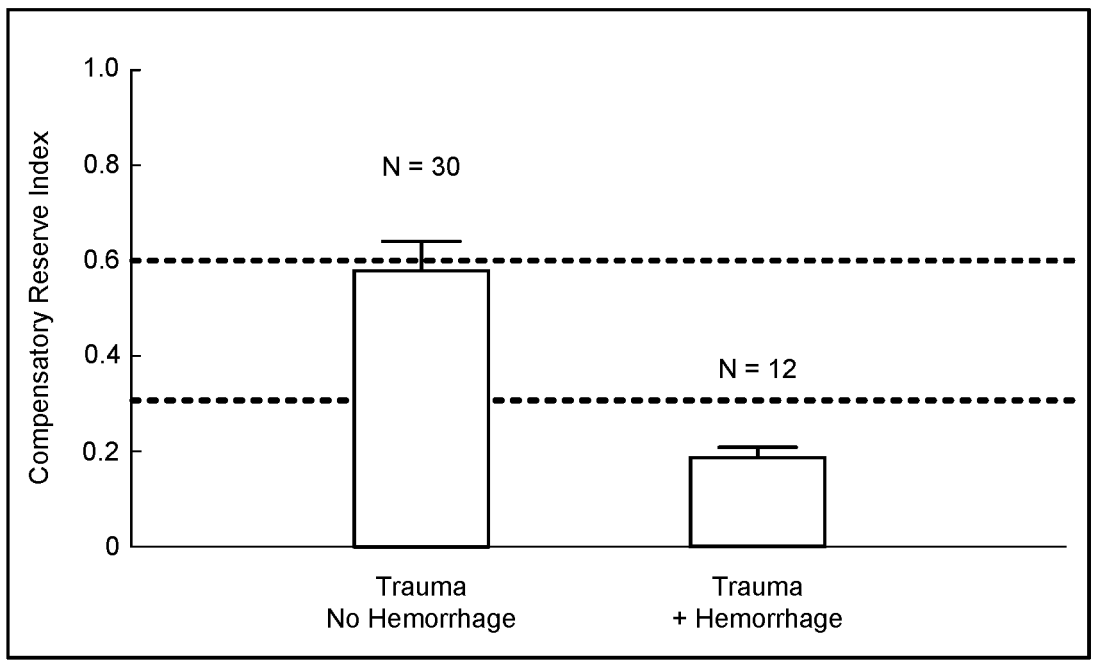

FIG. 9B illustrates the CRI for the non-bleeding patients (indicated in the graph as "Trauma No Hemorrhage") and for the bleeding patients (indicated in the graph as "Trauma+ Hemorrhage"). As shown in FIG. 9B, CRI values are low during bleeding.

Figure 9C:
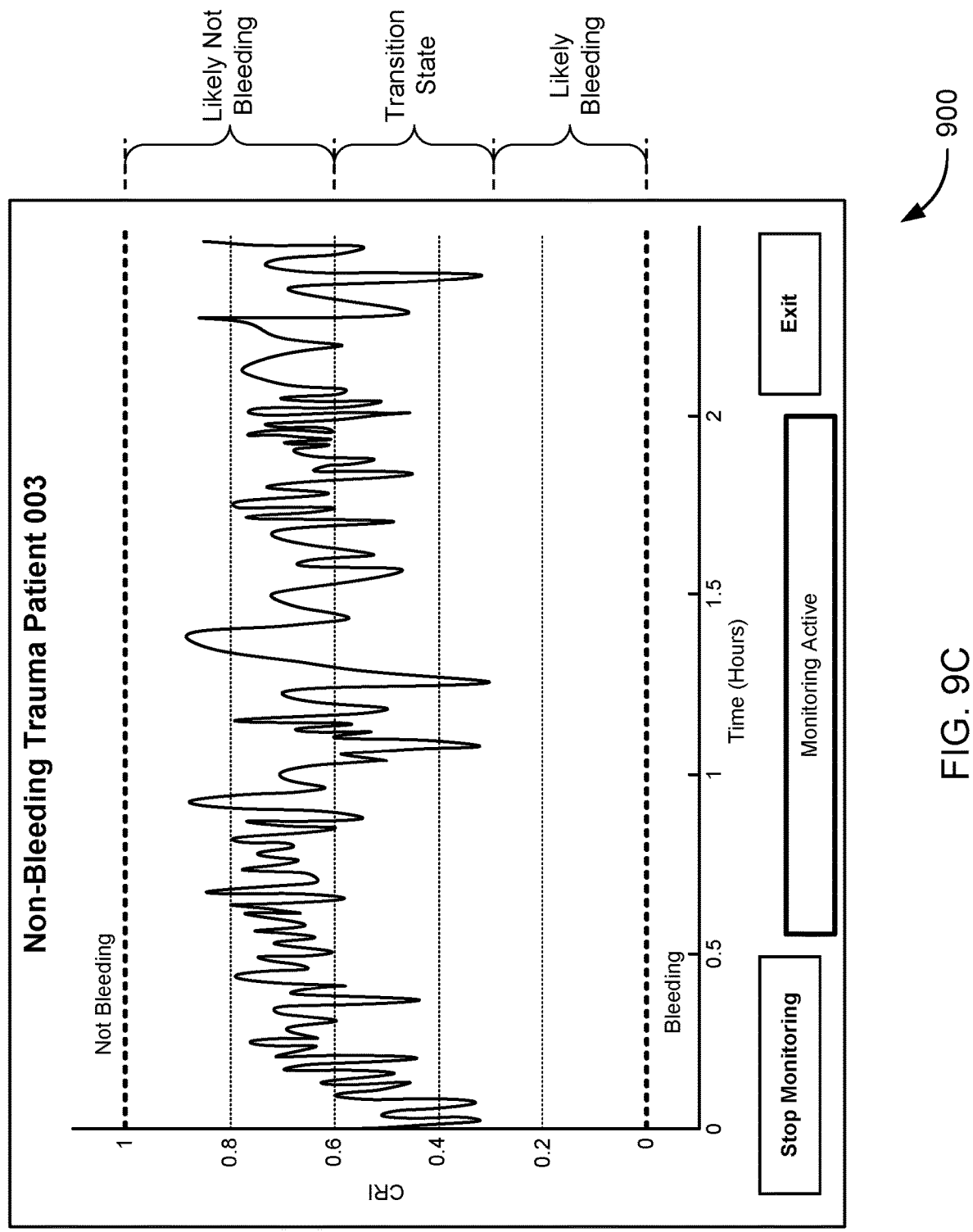
Figure 9D:
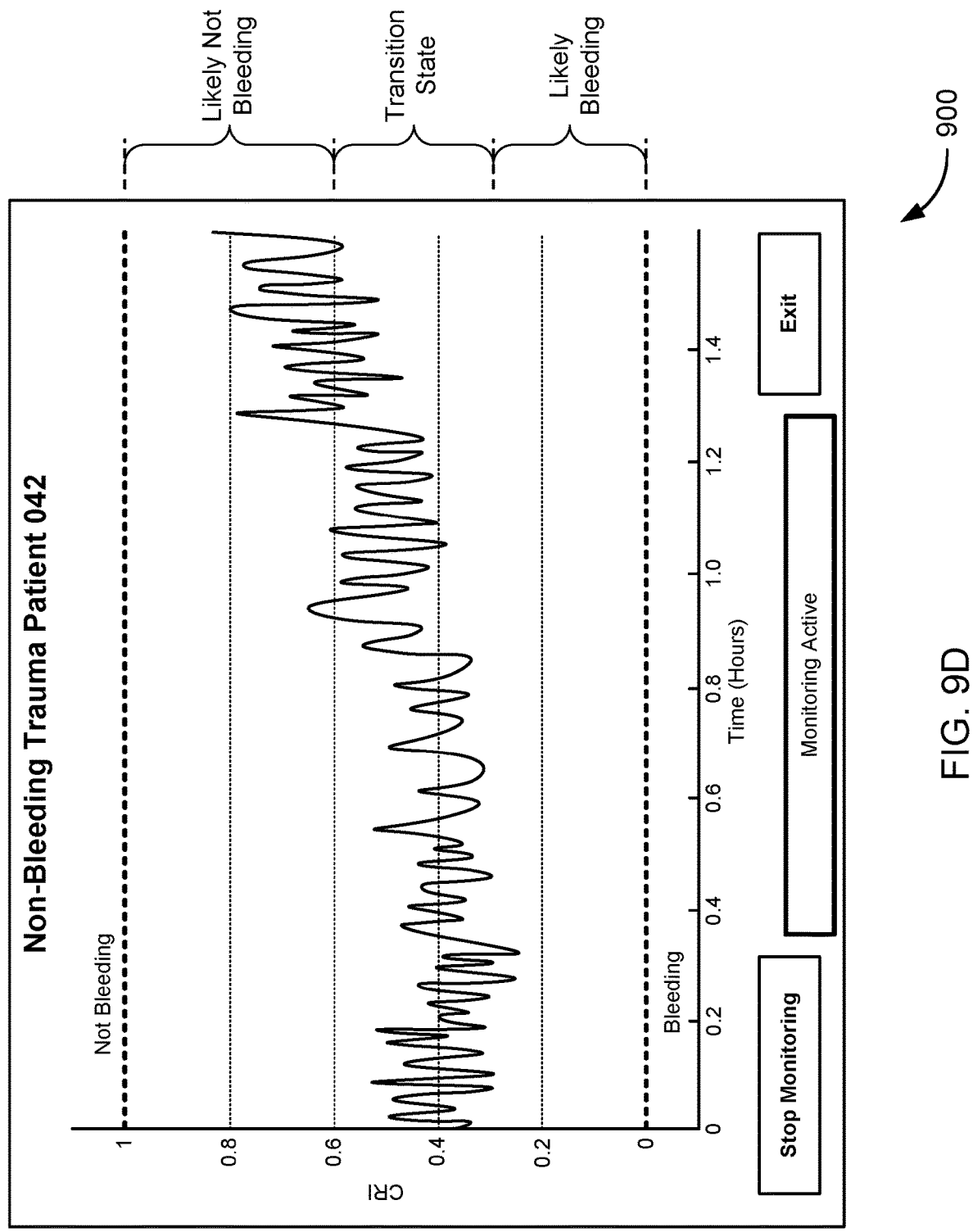
Figure 9E:
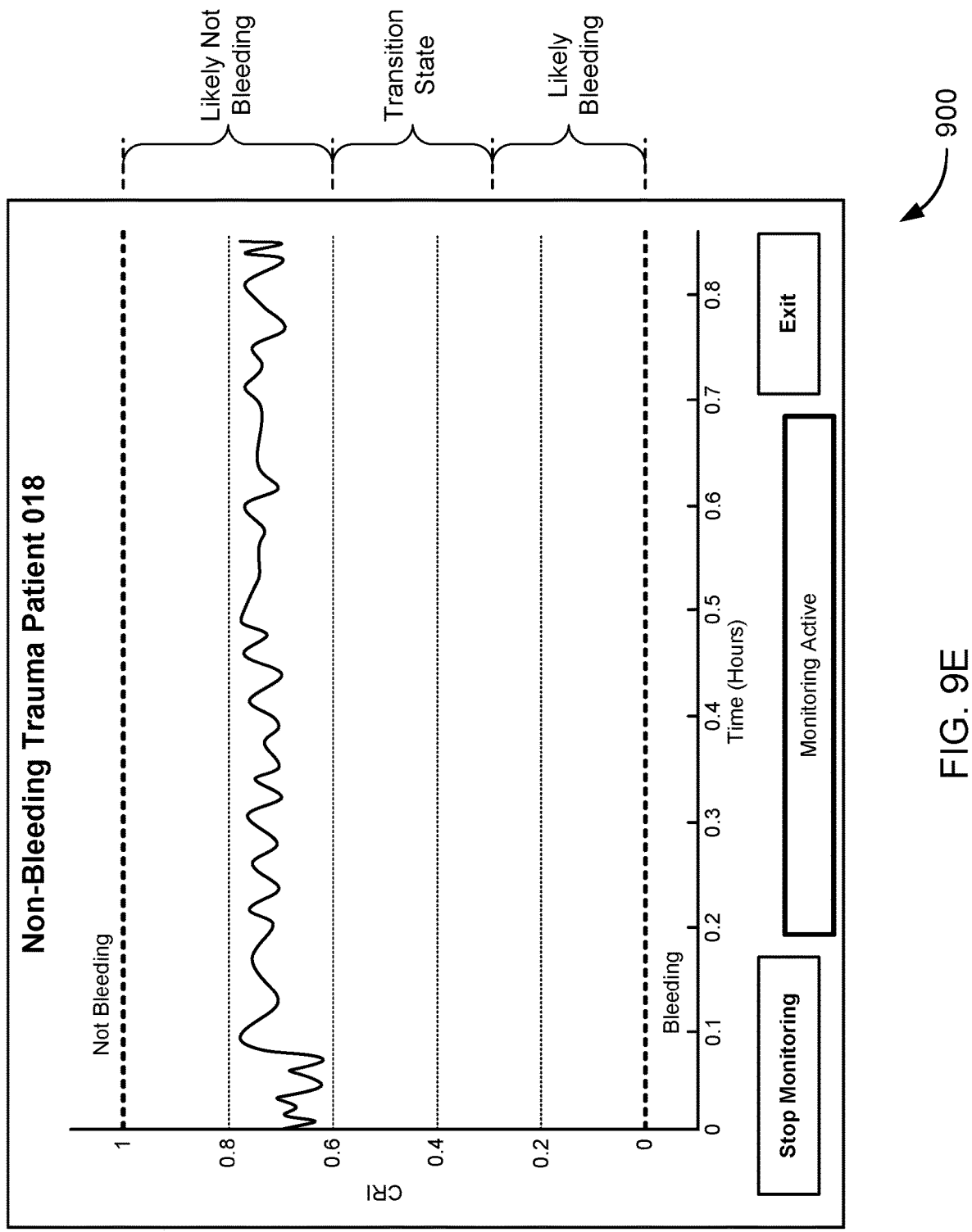

FIGS. 9C-9E illustrate line tracings of actual CRI curves for three representative patients among the non-bleeding group. The average CRI value for the non-bleeding patients before infusing of intravenous fluid ("IVF") is 0.56±0.17. FIG. 9C depicts the CRI curves for non-bleeding trauma patient 003, who had a CRI of >0.3 before infusion of IVF, and with IVF containing 2 L of saline solution. There was no sustained drop in CRI in this patient during or after infusion of IVF. FIG. 9D depicts the CRI curves for non-bleeding trauma patient 042, who had a CRI of 0.4 before infusion of IVF, and with IVF containing 1 L of saline solution. There was no wound exploration and no sustained drop in CRI in this patient during or after infusion of IVF. FIG. 9E depicts the CRI curves for non-bleeding trauma patient 018, who had a CRI of 0.65 before infusion of IVF, and with IVF containing 2 L of saline solution, 1 L of lactated ringer's ("LR") solution, and 2 packets of packed red blood cells ("PRBC"). There was no sustained drop in CRI in this patient during or after infusion of IVF. As shown in FIGS. 9C-9E, CRI is high or generally increasing during and after fluid resuscitation for each patient in the non-bleeding group.

Figure 9F:
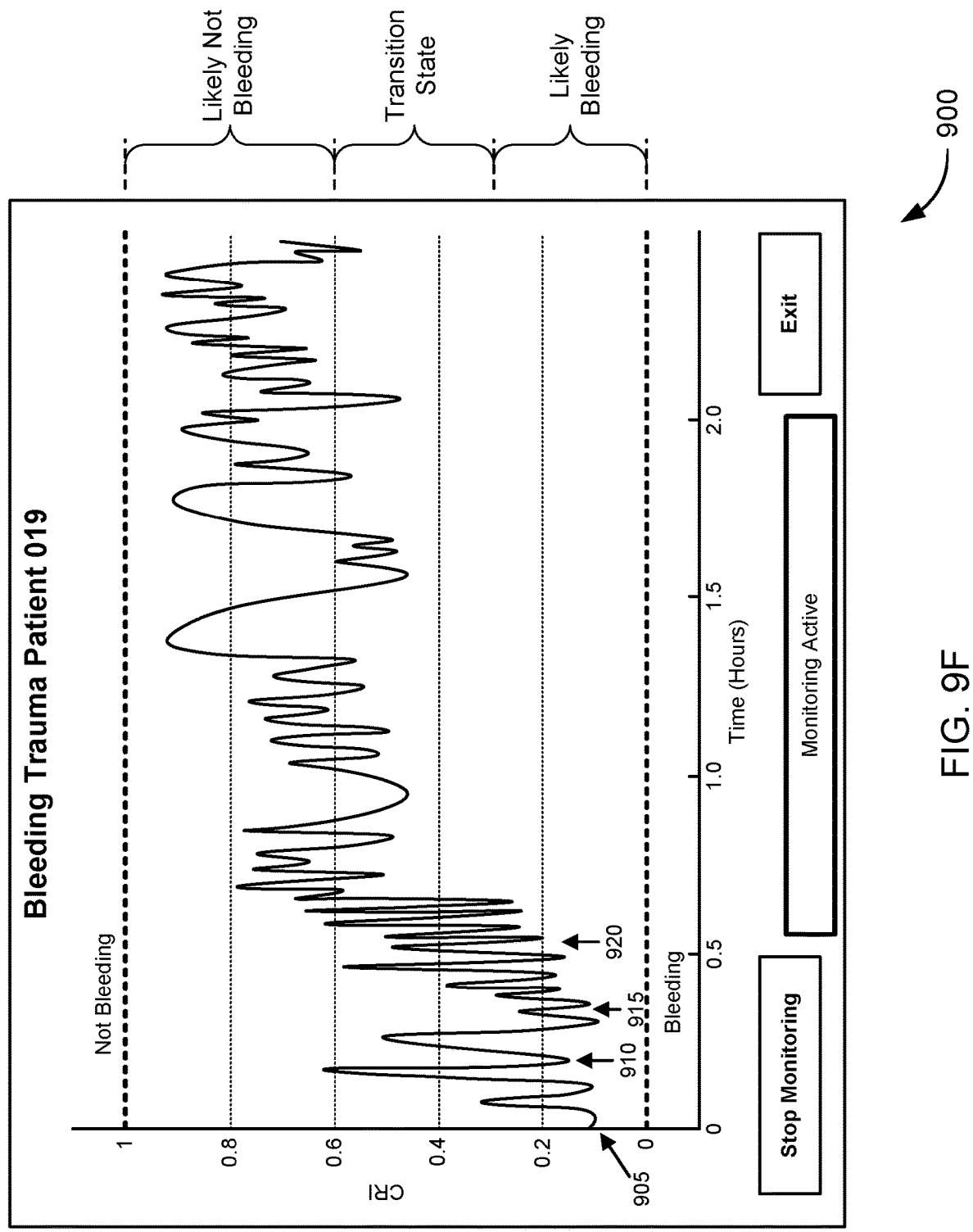
Figure 9G:
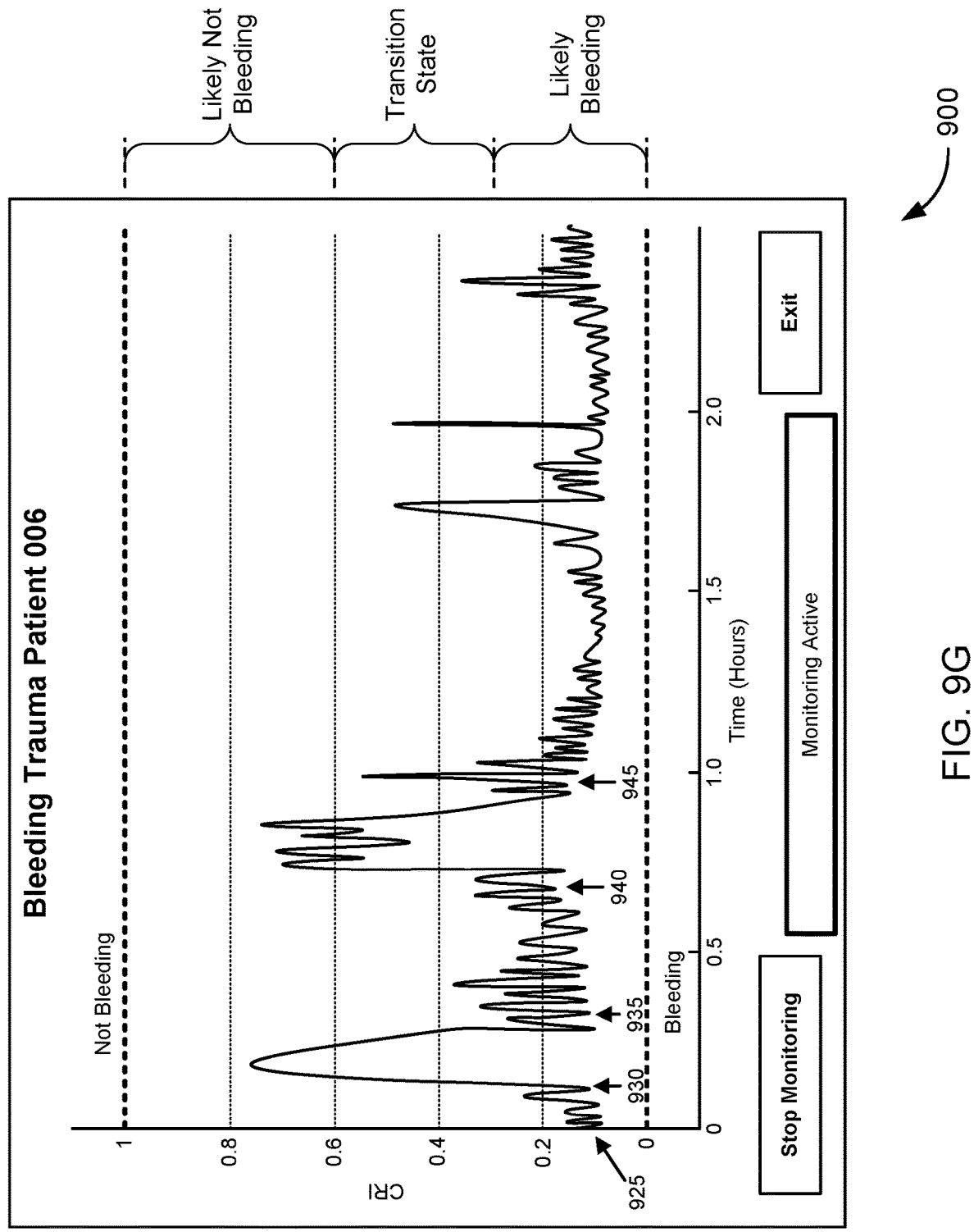
Figure 9H:
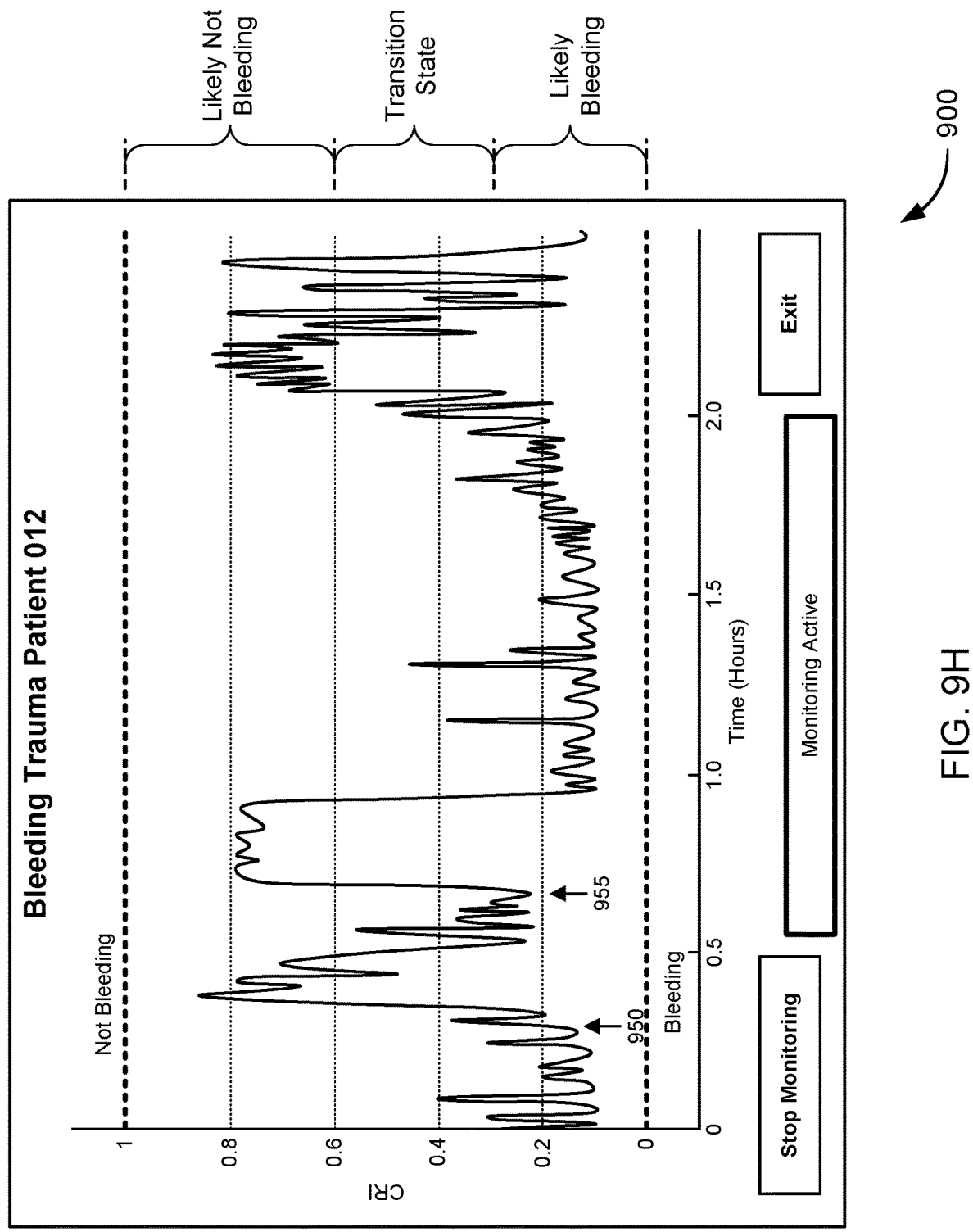

FIGS. 9F-9H illustrate line tracings of actual CRI curves for three representative patients among the bleeding group. The average CRI value for the non-bleeding patients before infusing of intravenous fluid ("IVF") is 0.17±0.07. FIG. 9F depicts the CRI curves for bleeding trauma patient 019, who had a CRI of 0.15 before infusion of IVF (at time 905), and with an infusion of a first IVF (at time 910), the first IVF containing 7 L of saline solution, 3 packets of PRBC, 1 packet of platelets ("PLTs"), and 3 packets of fresh frozen plasma ("FFP"). The CRI dropped after initial increase (as shown at time 915). At time 920, a second IVF was infused, the second IVF containing 4 L of saline solution, 3 packets of PRBC, and 3 packets of fresh frozen plasma ("FFP"). FIG. 9G depicts the CRI curves for bleeding trauma patient 006, who had a CRI of 0.15 before infusion of IVF (at time 925), and with an infusion of a first IVF (at time 930), the first IVF containing 2 L of saline solution. The CRI dropped after initial increase (as shown at time 935). At time 940, a second IVF was infused, the second IVF containing 1 L of saline solution. Again, the CRI dropped after initial increase (as shown at time 945). FIG. 9H depicts the CRI curves for bleeding trauma patient 012, who had a CRI of 0.15 before infusion of IVF, with infusions of a first IVF (at time 950) and a second IVF (at time 955), the first IVF containing 1 L of saline solution and the second IVF containing 2.25 L of saline solution. As shown in FIGS. 9F-9H, CRI drops after an initial increase (during and after fluid resuscitation) for each patient in the bleeding group.

In a different exemplary clinical study, another 50 patients were enrolled, of which 3 had incomplete data, 3 had indeterminate bleeding, 12 were actively bleeding, and 32 were not bleeding. For simplicity of comparison, the 3 patients who had incomplete data and the 3 patients who had indeterminate bleeding were excluded from further analysis. The mean initial CRI of bleeding patients was significantly lower compared to the non-bleeding patients (CRI of 0.17, 95% CI of 0.13-0.22 versus CRI of 0.56, 95% CI of 0.49-0.62, p<0.001). Using a cut-off of 0.21 had a sensitivity of 0.97 and specificity of 0.83 for identifying bleeding patients. CRI had a higher sensitivity than heart rate (9%), systolic blood pressure (36%), base deficit (29%), hemoglobin (50%), and hematocrit (50%). During ongoing bleeding, CRI on average decreased following fluid resuscitation, while on average increased for patients that did not have ongoing bleeding. As described below, the novel CRI computational algorithm that recognizes subtle changes in PPG waveforms can quickly and non-invasively discern which patients are actively bleeding and continuing to bleed with high sensitivity and specificity in acutely injured patients.

Figure 10:
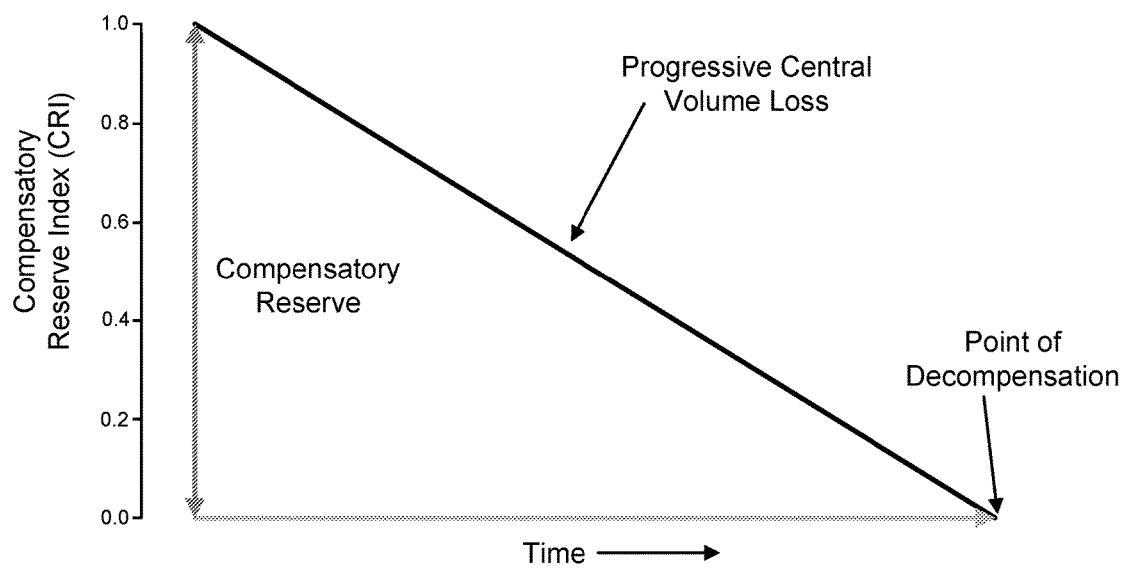
FIG. 10 is a schematic diagram illustrating Compensatory Reserve ("CR"), in accordance with various embodiments.
Figure 11:
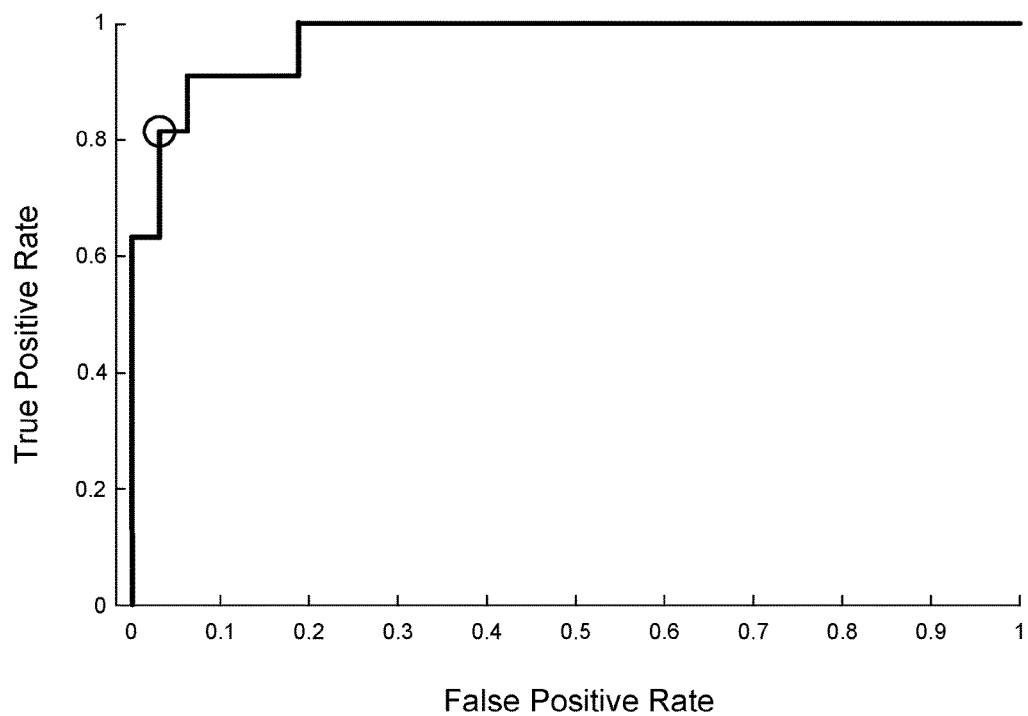
FIG. 11 is a graphical diagram illustrating receiver operating characteristic ("ROC") area under the curve ("AUC") for CRI and classification of actively bleeding versus not actively bleeding, in accordance with various embodiments.
Figure 12:
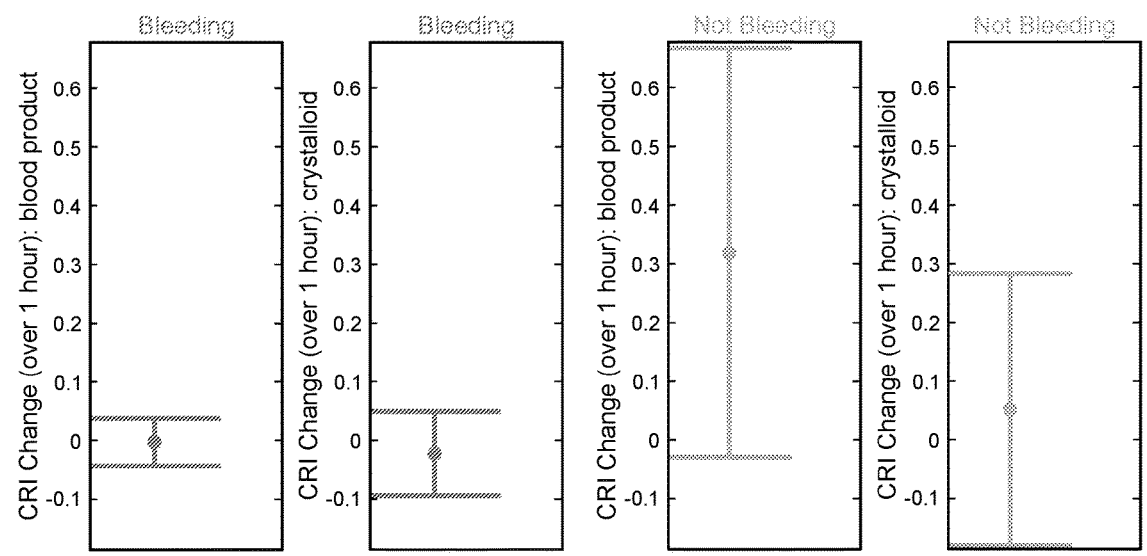
FIG. 12 is a set of graphical diagrams illustrating CRI response in bleeding patients and in non-bleeding patients one hour after infusion of 1 liter of crystalloid or 1 unit of blood product, in accordance with various embodiments.
Figure 13A:
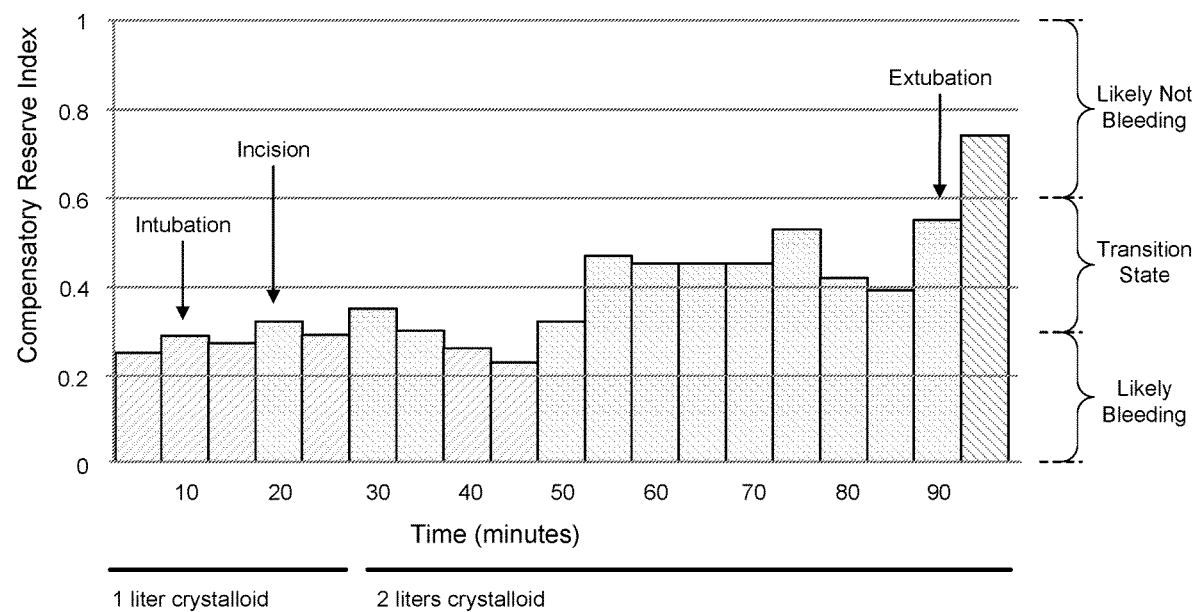
FIGS. 13A and 13B are graphical diagrams illustrating CRI changes over time for two example gunshot patients in response to varying resuscitation techniques.
Figure 13B:
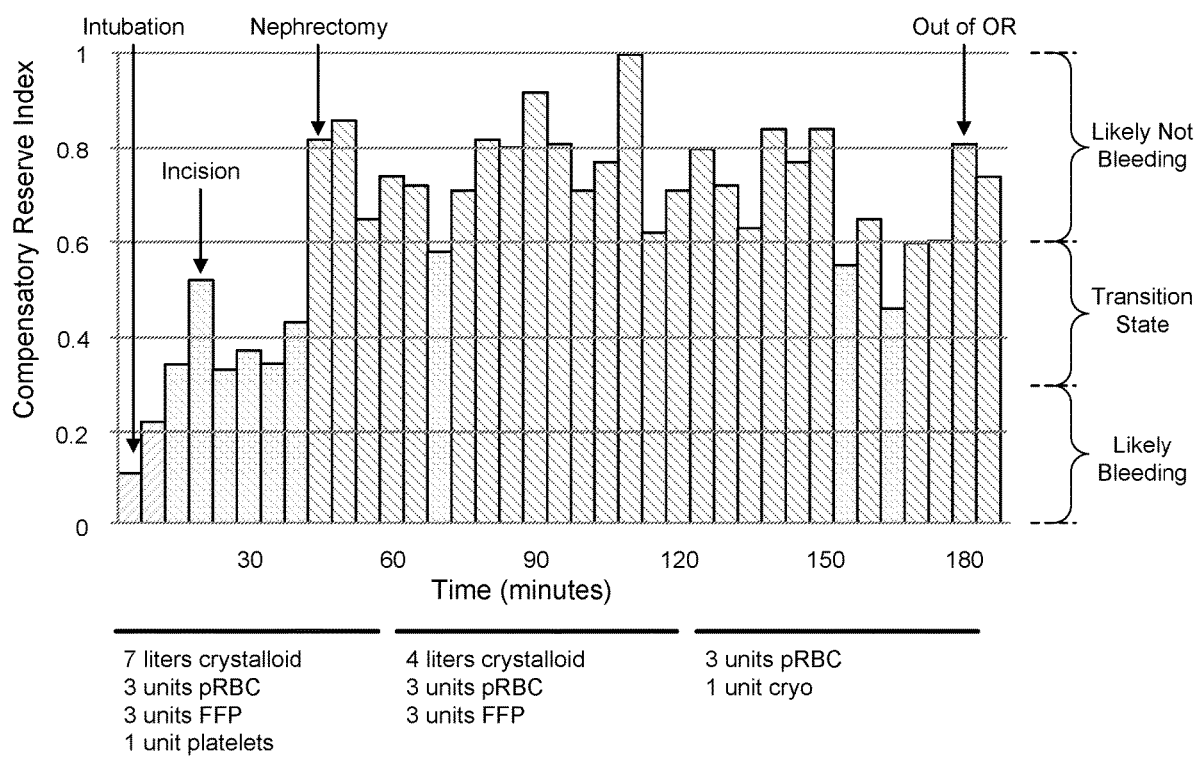

FIGS. 10-13B are results obtained from this different clinical study that evaluated CRI as a basis for rapid detection of bleeding in patients following injuries. FIG. 10 is a schematic diagram illustrating Compensatory Reserve ("CR"), while FIG. 11 is a graphical diagram illustrating receiver operating characteristic ("ROC") area under the curve ("AUC") for CRI and classification of actively bleeding versus not actively bleeding, and FIG. 12 is a set of graphical diagrams illustrating CRI response in bleeding patients and in non-bleeding patients one hour after infusion of 1 liter of crystalloid or 1 unit of blood product. FIGS. 13A and 13B (collectively, "FIG. 13") are graphical diagrams illustrating CRI changes over time for two gunshot patients in response to varying resuscitation techniques. Specifically, FIG. 13A is a graphical diagram illustrating CRI change over time for a patient with a negative laparotomy after a gunshot wound to the abdomen, while FIG. 13B is a graphical diagram illustrating CRI change over time for a patient with substantial blood loss and solid organ injury after a gunshot wound to the abdomen.

One of the most difficult tasks in clinical medicine is the assessment of intravascular volume status. This assessment is usually made by evaluating the patient's traditional vital signs, including heart rate ("HR"), blood pressure ("BP"), respiratory rate ("RR"), and oxygen saturation ("SpO2"), along with physical examination and laboratory studies. Unfortunately, traditional vital signs are notoriously unreliable due to the body's many compensatory mechanisms, which serve to maintain these vital signs during loss of up to 30-40% of total blood volume. As a result, unrecognized volume loss during the compensatory phase of hemorrhage can quickly lead to poor tissue perfusion, progressive acidosis and sudden, unexpected hemodynamic decompensation.

Individual-specific changes in vital sign waveforms are introduced by the body's many compensatory mechanisms. These mechanisms work together during the early stages of hemorrhage to maintain hemodynamic stability, but unfortunately, cannot be seen or trended by physicians. The total volume of blood loss an individual can tolerate before collapse varies depending on each person's unique ability to compensate. The CRI algorithm is designed to estimate an individual's current proportion of total tolerable volume loss, as defined by the following quantity:

$$CRI(t) = 1 - \frac{BLV(t)}{BLV_{HDD}}. \qquad \text{(Eq. 73)}$$

BLV represents the current blood loss volume of the subject and $BLV_{HDD}$ is the blood loss volume at which the subject will experience hemodynamic decompensation (defined in LBNP experiments as a systolic blood pressure<80 mmHg, loss of vision, or discomfort resulting in subject termination). CRI estimates this value by analyzing waveform features within a sliding 30-heartbeat window, and compares them to a library of waveform features originally obtained in the above LBNP experiments. By matching waveform features in the current subject to subjects from the LBNP experiments, CRI is able to determine when a patient will experience hemodynamic collapse in near real-time. With beat-to-beat re-calculation of CRI, this value can be trended over time. CRI values range from 1 to 0, and can be thought of as a percentage (100%-0%) of physiologic reserve remaining, where "1" represents supine normovolemia and "0" implies hemodynamic decompensation (as shown in FIG. 10). Values between "1" and "0" indicate the proportion of reserve available to compensate for further volume loss.

The CRI algorithm had subsequently been validated in healthy volunteers donating one unit of blood, and undergoing stepwise removal and replacement of up to 1.3 liters of blood. In these previous studies, the inventors had shown that CRI could quickly, reliably, and non-invasively detect relatively small to moderate volumes of blood loss in healthy adults, whereas other vital sign parameters, including HR, systolic BP ("SBP"), cardiac output, and stroke volume were unable to reliably detect the same volumes of blood loss. Further, when withdrawn blood was re-infused in study subjects, CRI increased and returned to baseline. These results prompted a prospective clinical trial to examine performance of the CRI algorithm in traumatically injured adolescent and adult patients. The goal was to determine whether or not the CRI algorithm could reliably detect acute blood loss and continued blood loss in the setting of trauma. Doing so would validate that the CRI algorithm effectively monitors volume loss in patient populations subject to sympathetic stimuli including those experiencing injury and pain. The following describes the results of the study to validate the CRI algorithm in detecting blood loss due to injury.

In this study, continuous non-invasive PPG waveform data were collected from 50 acutely injured, possibly bleeding patients. Investigators were present in the Denver Health Emergency Department Thursday-Sunday from 7 PM to 5 AM to enroll consecutive eligible patients from Oct. 17, 2013 to Feb. 2, 2014. Eligible patients were 15-89 years of age admitted to the emergency department with evidence of blunt or penetrating trauma, and remained eligible if treated in the operating room or surgical intensive care unit. All enrolled patients were categorized as either an "alert" or "activation" according to established Denver Health Emergency Department criteria (as shown in Table 1 below).

TABLE 1

Definitions of "alerts" and "activations" at Denver Health Medical Center during the study period.

Glasgow coma scale <8 with presumed thoracic, abdominal or pelvic injury, and/or respiratory compromise
Obstruction and/or intubation with presumed thoracic, abdominal or pelvic injury
Blunt trauma with SBP <90 mmHg
Mechanically unstable pelvic injury
Penetrating injury to the neck and/or torso with SBP <90 mmHg
Gunshot wound(s) to the torso
Stab wound(s) to the torso
Amputation(s) proximal to the wrist or ankle
Transfer from another facility, receiving blood to maintain vital signs
The emergency department attending physician or chief surgical resident suspects need for urgent operative intervention Patients were considered ineligible if they were pregnant, objected to participation at any time, were or became incarcerated, or were transferred from the emergency department to the ward. Once a patient was determined eligible, an adhesive pulse-oximeter finger sensor (Nonin Medical, Inc., Plymouth, Minn.) was placed on the patient's index, middle, or ring finger, on the side opposite the blood pressure cuff. The finger sensor was attached to a DataOx™ monitor (Flashback Technologies Inc., Boulder, Colo.). These small, lightweight data collection devices are composed of a Nonin OEM III pulse oximeter, processor, memory, Bluetooth radio and battery. DataOx™ devices continuously recorded and time stamped each patient's PPG waveforms. Due to the limited number of devices, patients were enrolled each night until all devices were in use; at that point no more patients could be enrolled until the next evening.

Data collection was carried out over a 24-hour period, unless the patient was incarcerated or transferred out of the emergency department to the ward, at which point it was stopped. Demographic, clinical, and treatment information were prospectively collected in parallel with waveform data collection. Once waveform data collection was complete for each patient, the waveform data were off-loaded from each DataOx™ for later analysis. Recordings were retrospectively analyzed to generate CRI estimates using the CipherOx CRI™ system (V2.0.2, Flashback Technologies, Boulder Colo.). Demographic, clinical, and treatment information were entered into a RedCap database by hour of treatment. All data were available for each patient except where noted otherwise.

For data analysis purposes, patients were categorized into three groups based on their estimated blood loss ("EBL"): (1) active bleeding, defined as EBL>500 mL (known femur or pelvic fracture, known solid organ injury>grade 3, and/or intraoperative EBL of >500 mL); (2) indeterminate bleeding (known fractures other than femur or pelvis, grade 1-2 solid organ injuries, intraoperative EBL<500 mL); or (3) not actively bleeding (no evidence of bleeding, or minor bleeding<100 mL). Values between bleeding and non-bleeding patients were compared using two-tailed Student's t-test and Chi square analysis. Receiver operating characteristic ("ROC") area under the curve analysis was performed with identification of cut-off values that maximized the sensitivity and specificity for the identification of bleeding.

As indicated above, there were 50 patients prospectively enrolled, 3 who were excluded from data analysis due to incomplete data collection/device malfunction. Of the remaining 47 patients, there were 12 patients who were categorized as actively bleeding (estimated blood loss>500 mL), 3 who were indeterminate for bleeding (estimated blood loss between 100 mL and 500 mL), and 32 who were not actively bleeding (estimated blood loss<100 mL). For simplicity of comparison, the 3 patients who were classified as indeterminate were also excluded from further analysis. All further analysis is on the 44 patients who were classified as either bleeding or not bleeding. Demographics and clinical characteristics of these patients are detailed in Table 2 below.

TABLE 2

Demographics and clinical characteristics. Significant values are bolded with an asterisk.

|  | All patients (n = 44) | Actively bleeding (n = 12) | Not Actively Bleeding (n = 32) | P-value |
| --- | --- | --- | --- | --- |
| Age (avg years ± SD) | 33.6 (11.4) | 27.5 (7.0) | 35.9 (12.0) | 0.03* |
| Gender (% Male) | 39 (88.6) | 12 (100) | 27 (84.4) | 0.15 |
| Race (%) | | | | |
| Caucasian | 17 (38.6) | 4 (33.3) | 12 (37.5) | 0.80 |
| Hispanic | 19 (43.2) | 7 (58.3) | 12 (37.5) | 0.21 |
| African American | 7 (15.9) | 1 (8.3) | 6 (18.8) | 0.40 |
| Other | 1 (2.3) | 0 (0) | 1 (3.1) | 0.53 |
| Mechanism | | | | |
| Penetrating | 22 (50) | 6 (50) | 16 (50) | 1.0 |
| Blunt | 22 (50) | 6 (50) | 16 (50) | 1.0 |

TABLE 2-continued

Demographics and clinical characteristics. Significant values are bolded with an asterisk.

| | All patients (n = 44) | Actively bleeding (n = 12) | Not Actively Bleeding (n = 32) | P-value |
|---|---|---|---|---|
| ISS (avg ± SD) | 13 (13) | 27 (13) | 7.1 (8.6) | 0.60 |
| ETOH+ | 12 (27.3) | 4 (33.3) | 8 (25) | 0.58 |
| Urine toxicology positive adrenergic agonist | 5 (11.4) | 2 (16.7) | 3 (9.4) | 0.50 |
| Gunshot wound (%) | 12 (27.3) | 4 (33.3) | 8 (25) | 0.58 |
| Stab wound (%) | 10 (22.7) | 2 (16.7) | 8 (25) | 0.56 |
| Long bone/pelvic fractures (%) | 4 (9.1) | 4 (33.3) | 0 (0) | 0.001* |
| Intracranial injuries (%) | 4 (9.1) | 2 (16.7) | 2 (6.3) | 0.28 |
| Positive FAST exam (%) | 6 (13.6) | 5 (41.7) | 1 (3.1) | 0.001* |
| Surgical treatment in first 24 hours (%) | 16 (36.4) | 11 (91.7) | 5 (15.6) | <0.001* |
| Admitted to ICU in first 24 hours (%) | 19 (43.2) | 12 (100) | 5 (15.6) | <0.001* |
| Need for mechanical ventilation (%) | 14 (31.8) | | | |
| ICU length of stay (median, range in days) | 0, 0-15 | | | |
| Hospital length of stay (median, range in days) | 2, 0-53 | | | |
| Survival at 24 hours (%) | 43 (97.7) | 12 (100) | 31 (96.9) | 0.54 |
| Survival to discharge (%) | 42 (95.5) | | | |

Actively bleeding patients tended to be younger than non-bleeding patients (27.5±7 years versus 35.9±12 years, p=0.03), had more long bone and pelvic fractures (33.3% versus 0%, p=0.001), more often had a positive focused assessment with sonography in trauma ("FAST") examination (41.7% versus 3.1%, p=0.001), more often had emergent operative intervention (91.7% versus 15.6%, p<0.001), more often required mechanical ventilation (75% versus 15.6%, p<0.001), more often were admitted to the intensive care unit (100% versus 15.6%, p<0.001), and had longer length of stay in the intensive care unit (median length of stay 5.5 days versus 0 days, p<0.001). Actively bleeding patients were also more likely to receive blood products in the first hour of treatment (25% versus 3.1%, p=0.03), and received a larger volume of crystalloid resuscitation (2.3 L versus 1.3 L, p=0.007) (as shown in Table 3 below).

TABLE 3

Fluid administration in the first hour of treatment. Significant values are bolded with an asterisk.

| | All patients | Actively bleeding | Not Actively Bleeding | P-value |
|---|---|---|---|---|
| Received blood products (%) | 4 (9.1) | 3 (25) | 1 (3.1) | 0.03* |
| Crystalloid (L) | 1.6 (1.1) | 2.3 (1.6) | 1.3 (0.5) | 0.007* |

The average initial CRI was calculated over the first 5 minutes of data collection and was compared to the pre-hospital HR and SBP (since these values are used to triage patients), the initial HR and SBP in the trauma bay, the initial shock index ("SI"), and labs obtained within the first hour of admission including base deficit, lactate, hemoglobin, and hematocrit (as shown in Table 4 below).

TABLE 4

Initial measures of volume status. Laboratory values were obtained within the first hour of treatment. Significant values are bolded with an asterisk. HR = heart rate, SBP = systolic blood pressure, CRI = compensatory reserve index.

| | All patients | Actively bleeding | Not Actively Bleeding | P-value |
|---|---|---|---|---|
| Pre-hospital HR (avg ± SD) | 99 (21) | 102 (28) | 98 (18) | 0.60 |
| Pre-hospital SBP (avg ± SD) | 124 (34) | 101 (23) | 134 (33) | 0.005* |
| Initial HR (avg ± SD | 100 (21) | 98 (27) | 102 (18) | 0.60 |
| Initial SBP (avg ± SD) | 128 (32) | 99 (24) | 137 (29) | <0.001* |
| Initial Shock Index (avg ± SD) | 0.83 (0.27) | 1.05 (0.34) | 0.77 (0.20) | 0.002 |
| Initial CRI (avg, SD) | 0.45 (0.23) | 0.17 (0.07) | 0.56 (0.18) | <0.001* |
| Initial Hemoglobin (g/dL) | 14.6 (1.9) | 13.2 (2.0) | 15.2 (1.6) | 0.002* |

TABLE 4-continued

Initial measures of volume status. Laboratory values were obtained within the first hour of treatment. Significant values are bolded with an asterisk. HR = heart rate, SBP = systolic blood pressure, CRI = compensatory reserve index.

|  | All patients | Actively bleeding | Not Actively Bleeding | P-value |
|---|---|---|---|---|
| Initial hematocrit (%) | 45.0 (5.5) | 41.9 (6.6) | 46.3 (4.6) | 0.02* |
| Initial Base deficit (mEq/L) | −8 (−5) | −10 (−5) | −6 (−4) | 0.11 |
| Initial Lactate | 5.2 (2.2) | 5.9 (2.4) | 4.1 (1.6) | 0.30 |

The average initial CRI for bleeding patients was 0.17 (95% CI 0.13-0.22), which was significantly lower compared to non-bleeding patients (for whom the average initial CRI was 0.56, 95% CI 0.49-0.62, p<0.001). The pre-hospital SBP, initial SBP, initial shock index, hemoglobin, and hematocrit were also significantly different between actively bleeding and non-bleeding patients (as shown in Table 4 above).

Receiver operating characteristic area under the curve ("ROC AUC") analysis was performed on each metric, using a cut-off value that maximized sensitivity and specificity for identifying actively bleeding patients. Using a threshold value of 0.21, the receiver operating characteristic area under the curve for CRI was 0.97, yielding a sensitivity of 0.83 and a specificity of 0.97 for identifying acutely bleeding patients (as shown in FIG. 11). Alternatively, a threshold value of 0.37 had a sensitivity of 1.00, but a specificity of 0.81. CRI had the highest AUC of all metrics examined (as shown in Table 5 below). Metrics including lactate and initial heart rate also had relatively high sensitivity but had lower specificity compared to CRI. Metrics including pre-hospital HR, pre-hospital SBP, initial SBP, initial SI, base deficit, hemoglobin, and hematocrit all had specificity>90%, but all had lower sensitivity compared to CRI.

TABLE 5

Receiver operating characteristic area under the curve ("ROC AUC") analysis for metrics of volume status. The threshold value is the optimal value for discriminating between bleeding and non-bleeding patients. HR = heart rate, SBP = systolic blood pressure, SI = shock index, CRI = compensatory reserve index.

| Metric | Threshold | Sensitivity | Specificity | ROC AUC |
|---|---|---|---|---|
| Pre-hospital HR | 122 | 0.09 | 0.92 | 0.64 |
| Pre-hospital SBP | 90 | 0.36 | 0.96 | 0.81 |
| Initial HR | 65 | 0.75 | 0.06 | 0.53 |
| Initial SBP | 96 | 0.63 | 0.97 | 0.86 |
| Initial SI | 1.37 | 0.27 | 1.00 | 0.74 |
| CRI | 0.21 | 0.83 | 0.97 | 0.97 |
| Base deficit | −12 | 0.29 | 1.00 | 0.72 |
| Lactate | 4.3 | 0.80 | 0.67 | 0.73 |
| Hemoglobin | 12.6 | 0.5 | 1.0 | 0.76 |
| Hematocrit | 37.8 | 0.5 | 1.0 | 0.69 |

To test the ability of CRI to identify ongoing blood loss under fluid administration, the rate of change of CRI over the hour following fluid delivery of crystalloid and blood products was calculated for bleeding and non-bleeding patients. In actively bleeding patients, CRI on average decreased the hour after administration of each liter of crystalloid (with CRI of −0.02, 95% CI—0.05-0.01), and with each unit of blood product (with CRI of −0.04, 95% CI—0.08--0.01). In non-bleeding patients, CRI on average increased the hour after each liter of crystalloid (with CRI of 0.05, 95% CI—0.05-0.14), and after each unit of blood product (with CRI of 0.003, 95% CI—0.26-0.26). There was no statistically significant difference in CRI between bleeding and non-bleeding patients the hour after infusion of 1 liter of crystalloid (p=0.60). This value did, however, approach significance for the change in CRI the hour after infusion of 1 unit of blood product (p=0.06). These data are graphically represented in FIG. 12, demonstrating that the average change in CRI after fluid and blood administration had a narrower range in bleeding patients compared to non-bleeding patients.

To examine these trends over longer periods of time, the inventors visually compared trends in CRI to fluid and blood product administration. In spite of multiple factors that can alter the patient's compensatory factors (including, but not limited to, basal tone, heart rate, sedation, pain, etc.), it graphically appeared that CRI accurately reflected the patient's clinical volume status. Some examples of this are shown in FIGS. 13A and 13B.

The patient, whose CRI was measured and shown in FIG. 13A, was taken to the operating room emergently for an anterior abdominal gunshot wound. After laparotomy, he was found to have no injuries and did not have more than minimal bleeding. CRI reflected his fluid responsiveness, increasing to normal values after 3 liters of crystalloid. The patient's low initial CRI was likely a reflection of ethanol intoxication and dehydration.

The patient, whose CRI was measured and shown in FIG. 13B, presented with a gunshot wound to the left upper quadrant of the abdomen, and was also emergently taken to the operating room. The patient was found to have large volume hemoperitoneum, a left kidney injury requiring nephrectomy, and several enterotomies requiring bowel resection. The estimated blood loss from this procedure was 5 liters. CRI increased significantly once the source of bleeding was identified and treated.

Humans have a number of survival compensatory mechanisms, which allow them to tolerate up to 30-40% of circulating blood volume loss before changes in traditional vital signs become frankly apparent. There is also substantial variation in the response to blood loss from patient to patient and from study to study, making it difficult to establish cut-off values. Traditional vital signs are also not specific to volume loss and can be abnormal for a variety of reasons. Thus, discrimination between bleeding and non-bleeding patients is difficult using these metrics alone. Physical exam findings, such as changes in skin turgor and capillary refill are late findings and offer little to no diagnostic value in the assessment of acutely injured adults. Laboratory values, such as hemoglobin, hematocrit, lactate, and base deficit, can also be used as surrogates to assess circulating blood volume. The accuracy of hemoglobin and hematocrit are limited in patients who have received significant crystalloid resuscitation. While techniques have been described to discriminate between true anemia and hemodilution, they require additional tests using specific equipment. Base deficit is a rapidly and widely available serum laboratory marker of systemic acidosis that increases with hypoxemia and/or shock. In trauma settings, the degree of base deficit correlates with blood transfusion requirement, risk of multi-organ failure, and mortality. Unfortunately, base deficit is non-specific and can rise due to any derangement causing metabolic acidosis, including, but not limited to, intravascular volume loss, or the like. Serum lactate has similarly been used as a marker of acute blood loss, but is also non-specific. Furthermore, intoxication and chronic alcohol abuse, which are relatively common amongst the traumatically injured, are known causes of lactic acidosis. These facts underscore the importance of identifying new physiological metrics that can reliably detect volume loss in traumatically injured patients.

In this clinical study, the inventors collected continuous PPG waveform data from trauma patients from the time of arrival through resuscitation and/or operative intervention, and used this data to calculate a novel metric of hemodynamic reserve called CRI. CRI was then compared to traditional vital signs and the laboratory measures of volume loss referenced above. The change in CRI after fluid and blood administration was also examined. Results from this study support the primary hypothesis that CRI provides increased sensitivity and excellent specificity for the detection of acute blood loss. CRI decreased despite fluid and blood administration in patients who were actively bleeding, and increased in those who were not. CRI also increased with appropriate volume resuscitation once the source of bleeding was identified and stopped. Consistent with our previous observations and the observations of others, traditional vital signs and laboratory studies had limited utility during initial evaluation. Our secondary hypothesis, that injury and pain do not alter the fundamental features of the waveforms that were used to build the CRI algorithm, is also supported by our results. These findings are important, because the physiological response of an injured patient who experiences blood loss could arguably differ from that of the research subjects on which the algorithms were built.

Many new and sophisticated parameters have recently been developed for the evaluation of fluid status and fluid responsiveness. Static parameters have not performed well, and while dynamic parameters are better at predicting fluid responsiveness, their clinical use has not been widely accepted possibly because of difficulty in application and/or interpretation. Parameters such as stroke volume variation ("SVV") and pulse pressure variation ("PPV") are limited to the evaluation of mechanically ventilated patients and often require an invasive monitoring device. Ideal parameters for monitoring fluid status and responsiveness to fluids are non-invasive and can function in spontaneously breathing patients. Another example of one such parameter is near-infrared spectroscopy ("NIRS"), which utilizes the near-infrared light spectrum to penetrate several centimeters into human tissue. NIRS demonstrates decreased muscle oxygenation in central hypovolemia and can discriminate between patients at various levels of shock, but may still be inferior to traditional SBP.

A number of metrics for monitoring volume loss using the PPG signal have been proposed. Its ability to demonstrate the interaction between cardiac pulsation, arterial/venous pressure and peripheral vascular tone has led many to attempt to characterize subtle changes in the circulation, which are not otherwise apparent. Most studies have focused on the beat-to-beat variation of PPG waveforms. Various types of analysis of PPG waveform variability can detect small volume blood loss in spontaneously breathing patients without appreciable changes in HR or BP. The pleth variability index ("PVI") has been shown to predict fluid responsiveness in mechanically ventilated adult patients. Unfortunately, PVI shows a considerable degree of inter-subject variability, limiting its use for distinguishing between hypovolemic and non-hypovolemic subjects based on a single measurement. Thus, like many other parameters used to detect hypovolemia, PVI must be trended over time to give meaningful information.

The inventors believe that measuring the magnitude of the reserve to compensate for blood loss using our algorithm was more sensitive than other metrics likely because it reflected the integrated capacity of regulatory mechanisms to maintain adequate perfusion and oxygen delivery to the tissue. By discovering associations and understanding patterns within vital sign waveforms, current and future analytical tools will have the potential to improve care, save lives and lower health care costs. These algorithms in turn will become the foundation for the next generation of algorithms, which will enable powerful compact models for estimation, prediction and control of medical care. This study does have limitations, including the lack of pre-hospital waveform data, small sample size, and estimation of blood loss volumes. In spite of these limitations, it did, however, demonstrate superior sensitivity when compared to traditional vital sign and laboratory values in predicting clinically significant blood loss. It also suggested that CRI could identify continued blood loss in the face of fluid resuscitation. These results support a growing body of literature suggesting that the CRI has promise as a clinically meaningful indicator of hemorrhage and a non-invasive method to monitor fluid resuscitation.

In yet another clinical trial, accurate guidance of resuscitation volume needs in trauma patients. As noted above, hemorrhage is the second leading cause of trauma-related death and the most common cause of preventable death on the battlefield. Accurate guidance for fluid resuscitation of injured warfighters is critical to improving patient outcomes. In this study, three new algorithms for guiding fluid resuscitation are evaluated. The first is estimating Fluid Volume Requirements ("FVR" or "FVR Algorithm"), which monitors the patient's photoplethysmogram ("PPG") signal as fluid is administered, and directly estimates amount of whole blood (in milliliters (mL)) needed. A simple monitor that can accurately estimate volume needs can prevent under resuscitation—which poses the risk of hypotension and end organ damage—and over-resuscitation—which may dislodge clots from vascular injuries, resulting in further blood loss, hemodilution, and/or possibly death. The second is Detection of Ongoing Fluid Loss ("DOFL"; "OFL"; "DOFL Algorithm"; or "OFL Algorithm"), which monitors patient's PPG signal and directly identifies whether the patient is experiencing ongoing blood loss. A simple monitor (e.g., standalone hand held monitor, or a monitor that is integrated into existing monitors, or the like) that can automatically and accurately detect ongoing bleeding can save lives and improve patient outcomes. The third is Rapid Estimation (or Determination) of Immediate Fluid Requirements ("RE-IFR"; "RDIFR"; "IFR"; "REIFR Algorithm"; "RDIFR Algorithm"; or "IFR Algorithm"), which monitors the patient's PPG signal and flags the need for additional fluid (this classification is made within one minute of the start of monitoring, and gives real-time indication of over- and under-resuscitation). A monitor that can quickly detect when a patient does not immediately require fluids can prevent over-resuscitation, which can save lives and improve patient outcomes, as aggressive fluid resuscitation may dislodge clots from vascular injuries, resulting in further blood loss, hemodilution, and/or possibly death.

In this study, 42 healthy volunteers (ages 19 to 36, 18 females and 24 males) underwent stepwise removal and replacement of approximately 20% of total blood volume (15 mL/Kg male; 13 mL/Kg female) while in the supine position at rest. A large bore IV was placed for blood removal and replacement. The blood was removed in 2-6 steps (with total blood removal of 578 mL to 1470 mL). Resuscitation was immediately given if the subject experienced symptoms due to blood loss, defined as a systolic blood pressure<80 mmHg or MAP 30% below baseline. After blood removal was complete, the removed volume was reinfused. Subjects were monitored continuously with the Nonin 9560 fingertip pulse oximeter. PPG signals were recorded and synchronized with blood draws and reinfusion. The FVR algorithm was applied to 5-minute moving time windows during the resuscitation (blood reinfusion) part of the study, and provided real-time estimates of additional volume required (in mL) to fully replace the fluid removed. Ongoing fluid loss was the blood draw period in the study. The FVR monitor receives as inputs CRI estimates and fluid administration history for a patient, and outputs the real-time estimates of patient fluid requirements (in mL). The DOFL or OFL algorithm was applied to 5-minute moving time windows during the study and gave real-time classification of ongoing bleeding or non-bleeding. The OFL monitor receives as input CRI estimates for a patient, and outputs an indication of whether the patient is bleeding or not bleeding (in some cases, in a real-time manner, or after every heartbeat, or after a predetermined interval, or the like). Finally, the subject was classified as needing fluid once 5% volume loss was achieved. The REIFR or IFR Algorithm was applied to 1-minute moving time windows and gave real-time classification of (yes/no determinations of) needing fluids. The IFR monitor receives as input CRI estimates for a patient, and outputs an indication of whether the patient needs more fluids or does not need any more fluids (in some cases, in a real-time manner, or after every heartbeat, or after a predetermined interval, or the like).

Regarding the results, the FVR Algorithm achieved a RMS error of <50 mL in estimated blood volume requirements. FIGS. 14A and 14B illustrate the correspondence between Fluid Volume Requirements ("FVR") estimation and actual volume requirements for two patients in the clinical trial. Both the DOFL and REIFR Algorithms achieved ROC area under the curve of better than 0.9 (sensitivity and specificity of >0.9) in identifying ongoing bleeding and flagging when no additional fluids were needed. In sum, the three algorithms for monitoring fluid resuscitation were evaluated on subjects undergoing 20% blood volume loss. These algorithms showed accurate results in estimation of blood volume requirements, classifying ongoing bleeding, and classifying when no additional whole blood was needed. These algorithms can be implemented on standard medical monitors ranging from the Nonin 9550 used by medics, to monitors used in hospitals.

Exemplary System and Hardware Implementation

FIG. 15 is a block diagram illustrating an exemplary computer or system hardware architecture, in accordance with various embodiments. FIG. 15 provides a schematic illustration of one embodiment of a computer system 1500 that can perform the methods provided by various other embodiments, as described herein, and/or can function as a monitoring computer, a CRI monitor, a processing unit of a sensor device, and/or the like, as described above. It should be noted that FIG. 15 is meant only to provide a generalized illustration of various components, of which one or more (or none) of each may be utilized as appropriate. FIG. 15, therefore, broadly illustrates how individual system elements may be implemented in a relatively separated or relatively more integrated manner.

The computer or hardware system 1500 is shown comprising hardware elements that can be electrically coupled via a bus 1505 (or may otherwise be in communication, as appropriate). The hardware elements may include one or more processors 1510, including, without limitation, one or more general-purpose processors and/or one or more special-purpose processors (such as digital signal processing chips, graphics acceleration processors, and/or the like); one or more input devices 1515, which can include, without limitation, a mouse, a keyboard and/or the like; and one or more output devices 1520, which can include, without limitation, a display device, a printer, and/or the like.

The computer or hardware system 1500 may further include (and/or be in communication with) one or more storage devices 1525, which can comprise, without limitation, local and/or network accessible storage, and/or can include, without limitation, a disk drive, a drive array, an optical storage device, solid-state storage device such as a random access memory ("RAM") and/or a read-only memory ("ROM"), which can be programmable, flash-updateable, and/or the like. Such storage devices may be configured to implement any appropriate data stores, including, without limitation, various file systems, database structures, and/or the like.

The computer or hardware system 1500 might also include a communications subsystem 1530, which can include, without limitation, a modem, a network card (wireless or wired), an infra-red communication device, a wireless communication device and/or chipset (such as a Bluetooth™ device, an 802.11 device, a WiFi device, a WiMax device, a WWAN device, cellular communication facilities, etc.), and/or the like. The communications subsystem 1530 may permit data to be exchanged with a network (such as the network described below, to name one example), with other computer or hardware systems, and/or with any other devices described herein. In many embodiments, the computer or hardware system 1500 will further comprise a working memory 1535, which can include a RAM or ROM device, as described above.

The computer or hardware system 1500 also may comprise software elements, shown as being currently located within the working memory 1535, including an operating system 1540, device drivers, executable libraries, and/or other code, such as one or more application programs 1545, which may comprise computer programs provided by various embodiments (including, without limitation, hypervisors, VMs, and the like), and/or may be designed to implement methods, and/or configure systems, provided by other embodiments, as described herein. Merely by way of example, one or more procedures described with respect to the method(s) discussed above might be implemented as code and/or instructions executable by a computer (and/or a processor within a computer); in an aspect, then, such code and/or instructions can be used to configure and/or adapt a general purpose computer (or other device) to perform one or more operations in accordance with the described methods.

A set of these instructions and/or code might be encoded and/or stored on a non-transitory computer readable storage medium, such as the storage device(s) 1525 described above. In some cases, the storage medium might be incorporated within a computer system, such as the system 1500. In other embodiments, the storage medium might be separate from a computer system (i.e., a removable medium, such as a compact disc, etc.), and/or provided in an installation package, such that the storage medium can be used to program, configure, and/or adapt a general purpose computer with the instructions/code stored thereon. These instructions might take the form of executable code, which is executable by the computer or hardware system 1500 and/or might take the form of source and/or installable code, which, upon compilation and/or installation on the computer or hardware system 1500 (e.g., using any of a variety of generally available compilers, installation programs, compression/decompression utilities, etc.) then takes the form of executable code.

It will be apparent to those skilled in the art that substantial variations may be made in accordance with specific requirements. For example, customized hardware (such as programmable logic controllers, field-programmable gate arrays, application-specific integrated circuits, and/or the like) might also be used, and/or particular elements might be implemented in hardware, software (including portable software, such as applets, etc.), or both. Further, connection to other computing devices such as network input/output devices may be employed.

As mentioned above, in one aspect, some embodiments may employ a computer or hardware system (such as the computer or hardware system 1500) to perform methods in accordance with various embodiments of the invention. According to a set of embodiments, some or all of the procedures of such methods are performed by the computer or hardware system 1500 in response to processor 1510 executing one or more sequences of one or more instructions (which might be incorporated into the operating system 1540 and/or other code, such as an application program 1545) contained in the working memory 1535. Such instructions may be read into the working memory 1535 from another computer readable medium, such as one or more of the storage device(s) 1525. Merely by way of example, execution of the sequences of instructions contained in the working memory 1535 might cause the processor(s) 1510 to perform one or more procedures of the methods described herein.

The terms "machine readable medium" and "computer readable medium," as used herein, refer to any medium that participates in providing data that causes a machine to operate in a specific fashion. In an embodiment implemented using the computer or hardware system 1500, various computer readable media might be involved in providing instructions/code to processor(s) 1510 for execution and/or might be used to store and/or carry such instructions/code (e.g., as signals). In many implementations, a computer readable medium is a non-transitory, physical, and/or tangible storage medium. In some embodiments, a computer readable medium may take many forms, including, but not limited to, non-volatile media, volatile media, or the like. Non-volatile media includes, for example, optical and/or magnetic disks, such as the storage device(s) 1525. Volatile media includes, without limitation, dynamic memory, such as the working memory 1535. In some alternative embodiments, a computer readable medium may take the form of transmission media, which includes, without limitation, coaxial cables, copper wire and fiber optics, including the wires that comprise the bus 1505, as well as the various components of the communication subsystem 1530 (and/or the media by which the communications subsystem 1530 provides communication with other devices). In an alternative set of embodiments, transmission media can also take the form of waves (including, without limitation, radio, acoustic and/or light waves, such as those generated during radio-wave and infra-red data communications).

Common forms of physical and/or tangible computer readable media include, for example, a floppy disk, a flexible disk, a hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read instructions and/or code.

Various forms of computer readable media may be involved in carrying one or more sequences of one or more instructions to the processor(s) 1510 for execution. Merely by way of example, the instructions may initially be carried on a magnetic disk and/or optical disc of a remote computer. A remote computer might load the instructions into its dynamic memory and send the instructions as signals over a transmission medium to be received and/or executed by the computer or hardware system 1500. These signals, which might be in the form of electromagnetic signals, acoustic signals, optical signals, and/or the like, are all examples of carrier waves on which instructions can be encoded, in accordance with various embodiments of the invention.

The communications subsystem 1530 (and/or components thereof) generally will receive the signals, and the bus 1505 then might carry the signals (and/or the data, instructions, etc. carried by the signals) to the working memory 1535, from which the processor(s) 1505 retrieves and executes the instructions. The instructions received by the working memory 1535 may optionally be stored on a storage device 1525 either before or after execution by the processor(s) 1510.

CONCLUSION

This document discloses novel tools and techniques for blood loss in patients (e.g., before, during, and/or after fluid resuscitation), compensatory reserve, and similar physiological states. While certain features and aspects have been described with respect to exemplary embodiments, one skilled in the art will recognize that numerous modifications are possible. For example, the methods and processes described herein may be implemented using hardware components, software components, and/or any combination thereof. Further, while various methods and processes described herein may be described with respect to particular structural and/or functional components for ease of description, methods provided by various embodiments are not limited to any particular structural and/or functional architecture but instead can be implemented on any suitable hardware, firmware and/or software configuration. Similarly, while certain functionality is ascribed to certain system components, unless the context dictates otherwise, this functionality can be distributed among various other system components in accordance with the several embodiments.

Moreover, while the procedures of the methods and processes described herein are described in a particular order for ease of description, unless the context dictates otherwise, various procedures may be reordered, added, and/or omitted in accordance with various embodiments. Moreover, the procedures described with respect to one method or process may be incorporated within other described methods or processes; likewise, system components described according to a particular structural architecture and/or with respect to one system may be organized in alternative structural architectures and/or incorporated within other described systems. Hence, while various embodiments are described with—or without—certain features for ease of description and to illustrate exemplary aspects of those embodiments, the various components and/or features described herein with respect to a particular embodiment can be substituted, added and/or subtracted from among other described embodiments, unless the context dictates otherwise. Consequently, although several exemplary embodiments are described above, it will be appreciated that the invention is intended to cover all modifications and equivalents within the scope of the following claims.

What is claimed is:

1. A system, comprising:
one or more sensors configured to obtain physiological data from a patient, wherein the physiological data is cardiovascular data of the patient; and
a computer system in communication with the one or more sensors, the computer system comprising:
one or more processors; and
a non-transitory computer readable medium in communication with the one or more processors, the computer readable medium having encoded thereon a set of instructions executable by the one or more processors to cause the computer system to:
receive the physiological data from the one or more sensors before, during, and after resuscitation following injury;
compare the physiological data received from the one or more sensors against a pre-existing model, the pre-existing model comprising a plurality of waveforms of reference data, each waveform of the plurality of waveforms corresponding to a respective value of compensatory reserve index ("CRI") determined by the following formula:

$$CRI(t) = 1 - \frac{BLV(t)}{BLV_{HDD}}$$

wherein CRI(t) is the compensatory reserve at time t, BLV(t) is an intravascular volume loss of a test subject at time t, and $BLV_{HDD}$ is an intravascular volume loss at a point of hemodynamic decompensation of the test subject,
wherein the physiological data includes waveform data of the patient, wherein waveform data of the patient includes one or more patient waveforms, wherein comparing the physiological data to the pre-existing model comprises comparing the waveform data of the patient with the plurality of waveforms of reference data;
determine a similarity, for each of the one or more patient waveforms of the waveform data of the patient, between a respective patient waveform of the one or more patient waveforms and each of one or more waveforms of the plurality of waveforms of reference data individually;
determine one or more values of CRI based on the respective similarities of each of the one or more patient waveforms of the waveform data of the patient, wherein each of the one or more patient waveforms was obtained from the patient at a respective time;
estimate a probability that the patient is bleeding, based at least in part on the one more values of CRI; and
control a therapeutic device based on the probability that the patient is bleeding, wherein controlling the therapeutic device includes adjusting a flow rate of an intravenous drip.

2. A method, comprising:
monitoring, with one or more sensors, physiological data of a patient before, during, and after resuscitation following injury, wherein the physiological data is cardiovascular data of the patient;
obtaining, with the computer system, the physiological data from the one or more sensors;
comparing, with the computer system, the physiological data received from the one or more sensors against a pre-existing model, the pre-existing model comprising a plurality of waveforms of reference data, each waveform of the plurality of waveforms corresponding to a respective value of compensatory reserve index ("CRI") determined by the following formula:

$$CRI(t) = 1 - \frac{BLV(t)}{BLV_{HDD}}$$

wherein CRI(t) is the compensatory reserve at time t, BLV(t) is an intravascular volume loss of a test subject at time t, and $BLV_{HDD}$ is an intravascular volume loss at a point of hemodynamic decompensation of the test subject,
wherein the physiological data includes waveform data of the patient, wherein waveform data of the patient includes one or more patient waveforms, wherein comparing the physiological data to the pre-existing model comprises comparing the waveform data of the patient with the plurality of waveforms of reference data;
determining a similarity, for each of the one or more patient waveforms of the waveform data of the patient, between a respective patient waveform of the one or more patient waveforms and each of one or more waveforms of the plurality of waveforms of reference data individually;
determining one or more values of CRI based on the respective similarities of each of the one or more patient waveforms of the waveform data of the patient, wherein each of the one or more patient waveforms was obtained from the patient at a respective time;
estimating, with the computer system, a probability that the patient is bleeding, based at least in part on the one or more values of CRI; and
controlling a therapeutic device based on the probability that the patient is bleeding, wherein controlling the therapeutic device includes adjusting a flow rate of an intravenous drip.

3. The method of claim 2, wherein resuscitation comprises at least one of infusing crystalloid in the patient, infusing blood products in the patient, or infusing intravenous fluid in the patient.

4. The method of claim 3, wherein the intravenous fluid comprises one or more of saline solution or lactated ringer's ("LR") solution.

5. The method of claim 3, wherein the blood products comprise one or more of infusion of packed red blood cells ("PRBC") in the patient, infusion of fresh frozen plasma ("FFP") in the patient, infusion of platelets ("PLTs") in the patient, or infusion of cryoprecipitated antihaemophilic factor ("cryo") in the patient.

6. The method of claim 2, wherein one or more of monitoring the physiological data, determining one or more values of CRI, estimating the probability that the patient is bleeding, or displaying the indication of at least one of an assessment, prediction, or estimate of the probability that the patient is bleeding are performed in real-time.

7. The method of claim 2, wherein the one or more values of CRI are estimated based on physiological data that are at least one of received before, received during, or received after a fluid resuscitation procedure.

8. The method of claim 2, wherein the one or more values of CRI comprise a plurality of values of CRI, and wherein estimating a probability that the patient is bleeding comprises estimating, with the computer system, a probability that the patient is bleeding based at least in part on an average value of CRI of the plurality of values of CRI.

9. The method of claim 2, wherein the one or more values of CRI comprise a plurality of values of CRI, and wherein estimating a probability that the patient is bleeding comprises estimating, with the computer system, a probability that the patient is bleeding based at least in part on a standard deviation of at least some of the plurality of values of CRI.

10. The method of claim 2, wherein the one or more values of CRI comprise a plurality of values of CRI, and wherein estimating a probability that the patient is bleeding comprises estimating, with the computer system, a probability that the patient is bleeding based at least in part on a skewness of at least some of the plurality of values of CRI.

11. The method of claim 2, wherein the one or more values of CRI comprise a plurality of values of CRI, and wherein estimating a probability that the patient is bleeding comprises estimating, with the computer system, a probability that the patient is bleeding based at least in part on a rate of change of at least some of the plurality of values of CRI.

12. The method of claim 2, wherein the one or more values of CRI comprise a plurality of values of CRI, and wherein estimating a probability that the patient is bleeding comprises estimating, with the computer system, a probability that the patient is bleeding based at least in part on a second derivative of at least some of the plurality of values of CRI over the respective plurality of times, wherein the plurality of values of CRI varies as a function of time.

13. The method of claim 2, wherein the one or more values of CRI comprises a plurality of values of CRI, and wherein and wherein estimating a probability that the patient is bleeding comprises estimating, with the computer system, a probability that the patient is bleeding based at least in part on a difference between at least a first and a second value of CRI of the plurality of values of CRI.

14. The method of claim 2, wherein the indication is a value between 0 and 1.

15. The method of claim 14, wherein a value of 1 indicates that the patient is not bleeding, and wherein a value of 0 indicates that the patient is bleeding.

16. The method of claim 2, wherein the plurality of waveforms of reference data are generated by exposing one or more test subjects to a state of hemodynamic decompensation or near hemodynamic decompensation, or a series of states progressing towards hemodynamic decompensation, and collecting physiological data of the one or more test subjects.

17. The method of claim 2, wherein determining a similarity further comprises:
producing, for each respective patient waveform of the one or more patient waveforms, a respective similarity coefficient expressing a similarity between the respective patient waveform and each of the one or more waveforms of the plurality of waveforms of reference data individually;
normalizing, with the computer system, the respective similarity coefficients of the respective patient waveform for each of the one or more waveforms of the plurality of waveforms of reference data; and
summing each respective value of CRI, corresponding to each of the one or more waveforms of the plurality of waveforms of reference data, respectively weighted by the normalized similarity coefficient for each of the one or more waveforms of the plurality of waveforms of reference data, for the respective patient waveform; and
determining, for the respective patient waveform, an estimated value of CRI of the patient, based on the sum of the values of CRI as weighted by the normalized similarity coefficients.

18. The method of claim 2, wherein estimating a probability that the patient is bleeding is based at least in part on a fixed time history of monitoring the physiological data of the patient.

19. The method of claim 2, wherein estimating a probability that the patient is bleeding is based at least in part on a dynamic time history of monitoring the physiological data of the patient.

20. The method of claim 2, wherein at least one of the one or more sensors each comprises at least one of a blood pressure sensor, an intracranial pressure monitor, a central venous pressure monitoring catheter, an arterial catheter, a cardiac monitor, a transcranial Doppler sensor, a transthoracic impedance plethysmograph, a pulse oximeter, a near infrared spectrometer, a ventilator, an accelerometer, or an electronic stethoscope.

21. The method of claim 2, wherein the physiological data comprises blood pressure waveform data.

22. The method of claim 2, wherein the physiological data comprises plethysmograph waveform data.

23. The method of claim 2, wherein the physiological data comprises photoplethysmograph ("PPG") waveform data.

24. The method of claim 2, wherein the plurality of waveforms of reference data are generated by inducing a test subject to enter one or more physiological states, and obtaining physiological data from the test subject while the test subject is in a respective physiological state of the one or more physiological states.

25. The method of claim 24, further comprising:
inducing a physiological state of reduced circulatory system volume in the test subject.

26. The method of claim 25, wherein inducing the physiological state comprises subjecting the test subject to lower body negative pressure ("LBNP").

27. The method of claim 25, wherein inducing the physiological state comprises subjecting the test subject to dehydration.

28. The method of claim 24, wherein the one or more physiological states comprise a state of cardiovascular collapse or near-cardiovascular collapse.

29. The method of claim 24, wherein the one or more physiological states comprise a state of euvolemia.

30. The method of claim 24, wherein the one or more physiological states comprise a state of hypervolemia.

31. The method of claim 24, wherein the one or more physiological states comprise a state of dehydration.

32. The method of claim 24, further comprising correlating the physiological data of the test subject to the respective physiological state, wherein correlating the physiological data with the respective physiological state of the test subject further comprises:

- identifying, with the computer system, a most predictive set of signals $S_k$ out of a set of signals $s_1, s_2, \ldots, s_D$ for each of one or more outcomes $o_k$, wherein the most-predictive set of signals $S_k$ corresponds to a first data set representing a first physiological parameter of the physiological data, and wherein each of the one or more outcomes $o_k$ represents a physiological state measurement of the one or more physiological states respectively;
- autonomously learning, with the computer system, a set of probabilistic predictive models $ô_k = M_k(S_k)$, where $ô_k$ is a prediction of outcome $o_k$ derived from a model $M_k$ that uses as inputs values obtained from the set of signals $S_k$; and
- repeating, with the computer system, the operation of autonomously learning incrementally from data that contains examples of values of signals $s_1, s_2, \ldots, s_D$ and corresponding outcomes $o_1, o_2, \ldots, o_K$.

33. An apparatus, comprising:

a non-transitory computer readable medium having encoded thereon a set of instructions executable by one or more computers to cause the apparatus to:

- receive physiological data from one or more sensors before, during, and after resuscitation following injury, wherein the physiological data is cardiovascular data of the patient;
- compare the physiological data received from the one or more sensors against a pre-existing model, the pre-existing model comprising a plurality of waveforms of reference data, each waveform of the plurality of waveforms corresponding to a respective value of compensatory reserve index ("CRI") determined by the following formula:

$$CRI(t) = 1 - \frac{BLV(t)}{BLV_{HDD}}$$

wherein CRI(t) is the compensatory reserve at time t, BLV(t) is an intravascular volume loss of a test subject at time t, and $BLV_{HDD}$ is an intravascular volume loss at a point of hemodynamic decompensation of the test subject, wherein the physiological data includes waveform data of the patient, wherein waveform data of the patient includes one or more patient waveforms, wherein comparing the physiological data to the pre-existing model comprises comparing the waveform data of the patient with the plurality of waveforms of reference data;

determine a similarity, for each of the one or more patient waveforms of the waveform data of the patient, between a respective patient waveform of the one or more patient waveforms and each of one or more waveforms of the plurality of waveforms of reference data individually;

determine one or more values of CRI based on the respective similarities of each of the one or more patient waveforms of the waveform data of the patient, wherein each of the one or more patient waveforms was obtained from the patient at a respective time;

estimate a probability that the patient is bleeding, based at least in part on the one more values of CRI; and control a therapeutic device based on the probability that the patient is bleeding, wherein controlling the therapeutic device includes adjusting a flow rate of an intravenous drip.

\* \* \* \* \*